US011938265B2

(12) United States Patent
Engelhard et al.

(10) Patent No.: US 11,938,265 B2
(45) Date of Patent: *Mar. 26, 2024

(54) DEVICES, SYSTEMS, AND METHODS FOR ADHERENCE MONITORING AND PATIENT INTERACTION

(71) Applicant: Gecko Health Innovations, Inc., Cambridge, MA (US)

(72) Inventors: Yechiel Engelhard, Boston, MA (US); Mark Maalouf, Cambridge, MA (US); Michael Chiu, Somerville, MA (US)

(73) Assignee: Gecko Health Innovations, Inc., Cambridge, MA (US)

( * ) Notice: Subject to any disclaimer, the term of this patent is extended or adjusted under 35 U.S.C. 154(b) by 164 days.

This patent is subject to a terminal disclaimer.

(21) Appl. No.: 17/572,103

(22) Filed: Jan. 10, 2022

(65) Prior Publication Data

US 2022/0143335 A1    May 12, 2022

Related U.S. Application Data

(63) Continuation of application No. 14/375,696, filed as application No. PCT/US2013/047507 on Jun. 25, 2013, now Pat. No. 11,253,661.

(Continued)

(51) Int. Cl.
*G16H 20/13* (2018.01)
*A61M 15/00* (2006.01)
(Continued)

(52) U.S. Cl.
CPC ...... *A61M 15/008* (2014.02); *A61M 15/0093* (2014.02); *G16H 20/13* (2018.01);
(Continued)

(58) Field of Classification Search
CPC ........ G16H 10/00; G16H 10/20; G16H 10/40; G16H 15/00; G16H 20/00; G16H 20/10;
(Continued)

(56) References Cited

U.S. PATENT DOCUMENTS

| 4,817,822 A | 4/1989 | Rand et al. |
| 5,042,467 A | 8/1991 | Foley et al. |

(Continued)

FOREIGN PATENT DOCUMENTS

| CN | 202289119 U | 7/2012 |
| CN | 204864412 U | 12/2015 |

(Continued)

OTHER PUBLICATIONS

Tsai et al. 2010, "iMAT: Intelligent medication administration tools," The 12th IEEE International Conference on e-Health Networking, Applications and Services, Lyon, France, 2010, pp. 308-315, doi: 10.1109/HEALTH.2010.5556551.*

(Continued)

*Primary Examiner* — Robert W Morgan
*Assistant Examiner* — Charles P Coleman
(74) *Attorney, Agent, or Firm* — Flaster Greenberg P.C.

(57) ABSTRACT

Devices, systems, and methods are provided for adherence monitoring and patient interaction. In general, the devices, systems, and methods can facilitate a patient's adherence to a medication schedule and can facilitate monitoring and tracking of the patient's adherence to the medication schedule. In one embodiment, a medical accessory such as a cap is provided that can be configured to attach to existing medication dispensers, such as asthma inhalers, or to be integrated into a custom-made medication dispenser. The accessory can be configured to provide a notification to the patient when medication is due. The accessory can be configured to detect usage of the dispenser. The accessory (Continued)

can be configured to provide data regarding dispensing of the medication to an external device. The data can be analyzed and provided for visualization on a user interface.

20 Claims, 21 Drawing Sheets

Related U.S. Application Data

(60) Provisional application No. 61/664,008, filed on Jun. 25, 2012.

(51) Int. Cl.
*G16H 40/63* (2018.01)
*G16H 40/67* (2018.01)
*A61B 5/00* (2006.01)
*A61B 5/11* (2006.01)

(52) U.S. Cl.
CPC ............ *G16H 40/63* (2018.01); *G16H 40/67* (2018.01); *A61B 5/1112* (2013.01); *A61B 5/4833* (2013.01); *A61M 15/009* (2013.01); *A61M 2205/18* (2013.01); *A61M 2205/3317* (2013.01); *A61M 2205/332* (2013.01); *A61M 2205/3324* (2013.01); *A61M 2205/3368* (2013.01); *A61M 2205/3375* (2013.01); *A61M 2205/3553* (2013.01); *A61M 2205/3584* (2013.01); *A61M 2205/3592* (2013.01); *A61M 2205/52* (2013.01); *A61M 2205/581* (2013.01); *A61M 2205/582* (2013.01); *A61M 2205/584* (2013.01); *A61M 2205/587* (2013.01); *A61M 2205/8212* (2013.01)

(58) Field of Classification Search
CPC ........ G16H 20/13; G16H 20/17; G16H 30/00; G16H 40/00; G16H 50/00; G16H 70/00; G16H 40/67; G16H 40/63; G16H 80/00; G06Q 50/22–24; A61M 15/008; A61M 15/0093; A61M 15/009; A61M 2205/18; A61M 2205/3317; A61M 2205/332; A61M 2205/3324; A61M 2205/3368; A61M 2205/3375; A61M 2205/3553; A61M 2205/3584; A61M 2205/3592; A61M 2205/52; A61M 2205/581; A61M 2205/582; A61M 2205/584; A61M 2205/8212; A61B 5/1112; A61B 5/4833
USPC .................................................. 705/2, 3, 20
See application file for complete search history.

(56) References Cited

U.S. PATENT DOCUMENTS

| | | | |
|---|---|---|---|
| 5,200,891 A | 4/1993 | Edl et al. | |
| 5,284,133 A | 2/1994 | Marshak et al. | |
| 5,331,953 A | 7/1994 | Fagerstroem et al. | |
| 5,333,106 A | 7/1994 | Lanpher et al. | |
| 5,338,157 A | 8/1994 | Blomquist | |
| 5,363,842 A | 11/1994 | Mishelevich et al. | |
| 5,505,192 A | 4/1996 | Samiotes et al. | |
| 5,536,249 A * | 7/1996 | Castellano | A61M 5/1723 128/DIG. 1 |
| 5,544,647 A | 8/1996 | Jewett et al. | |
| 5,544,661 A | 8/1996 | Davis et al. | |
| 5,602,802 A | 2/1997 | Leigh-Spencer et al. | |
| 5,622,163 A | 4/1997 | Jewett et al. | |
| 5,642,731 A | 7/1997 | Kehr et al. | |
| 5,752,235 A | 5/1998 | Edl et al. | |
| 5,768,382 A | 6/1998 | Walker et al. | |
| 5,779,364 A | 7/1998 | Cannelongo et al. | |
| 5,809,997 A | 9/1998 | Wolf et al. | |
| 5,828,751 A | 10/1998 | Walker et al. | |
| 5,839,429 A | 11/1998 | Marnfeldt et al. | |
| 5,842,468 A | 12/1998 | Denyer et al. | |
| 5,887,586 A | 3/1999 | Dahlbaeck et al. | |
| 5,970,143 A | 10/1999 | Walker et al. | |
| 5,976,082 A | 11/1999 | Wong et al. | |
| 6,018,289 A | 1/2000 | Sekura et al. | |
| 6,039,688 A | 3/2000 | Douglas et al. | |
| 6,084,504 A | 7/2000 | Kort et al. | |
| 6,102,855 A | 8/2000 | Chapman et al. | |
| 6,148,815 A * | 11/2000 | Wolf | A61M 15/008 128/200.14 |
| 6,168,568 B1 | 1/2001 | Gavriely et al. | |
| 6,190,326 B1 | 2/2001 | McKinnon et al. | |
| 6,198,383 B1 | 3/2001 | Sekura et al. | |
| 6,202,642 B1 | 3/2001 | McKinnon et al. | |
| 6,261,238 B1 | 7/2001 | Gavriely et al. | |
| 6,285,731 B1 | 9/2001 | Marnfeldt et al. | |
| 6,375,623 B1 | 4/2002 | Gavriely et al. | |
| 6,383,142 B1 | 5/2002 | Gavriely et al. | |
| 6,390,088 B1 | 5/2002 | Noehl et al. | |
| 6,424,599 B1 | 7/2002 | Ditzig et al. | |
| 6,540,672 B1 | 4/2003 | Rokkjaer et al. | |
| 6,561,022 B1 | 5/2003 | Doyle et al. | |
| 6,579,231 B1 | 6/2003 | Phipps et al. | |
| 6,581,357 B1 | 6/2003 | Lindenberger | |
| 6,604,650 B2 | 8/2003 | Sagar | |
| 6,612,985 B2 | 9/2003 | Eiffert et al. | |
| 6,637,430 B1 | 10/2003 | Voges et al. | |
| 6,652,455 B1 | 11/2003 | Kocher et al. | |
| 6,691,058 B2 | 2/2004 | Blakley et al. | |
| 6,697,649 B1 | 2/2004 | Bennett et al. | |
| 6,707,763 B2 | 3/2004 | Osberg et al. | |
| 6,729,327 B2 | 5/2004 | McFarland et al. | |
| 6,743,202 B2 | 6/2004 | Hirschman et al. | |
| 6,747,556 B2 | 6/2004 | Medema et al. | |
| 6,751,730 B1 | 6/2004 | Walker et al. | |
| 6,804,558 B2 | 10/2004 | Haller et al. | |
| 6,850,555 B1 | 2/2005 | Barclay et al. | |
| 6,904,907 B2 | 6/2005 | Speldrich et al. | |
| 6,937,150 B2 | 8/2005 | Medema et al. | |
| 6,958,691 B1 * | 10/2005 | Anderson | A61B 5/0002 128/200.14 |
| 6,978,780 B1 | 12/2005 | Marnfeldt et al. | |
| 6,990,975 B1 | 1/2006 | Jones et al. | |
| 7,016,744 B2 | 3/2006 | Richard et al. | |
| 7,024,331 B2 | 4/2006 | Jones et al. | |
| 7,072,738 B2 | 7/2006 | Robertson et al. | |
| 7,081,807 B2 | 7/2006 | Lai | |
| 7,133,329 B2 | 11/2006 | Alvarez-Icaza et al. | |
| 7,138,906 B2 | 11/2006 | Rosche et al. | |
| 7,139,701 B2 | 11/2006 | Harton et al. | |
| 7,151,456 B2 | 12/2006 | Godfrey et al. | |
| 7,170,823 B2 | 1/2007 | Joergensen et al. | |
| 7,191,777 B2 | 3/2007 | Brand et al. | |
| 7,198,172 B2 | 4/2007 | Lintell et al. | |
| 7,201,721 B2 | 4/2007 | Wilkinson et al. | |
| 7,205,775 B2 | 4/2007 | Kreit et al. | |
| 7,228,228 B2 | 6/2007 | Bartlett et al. | |
| 7,233,228 B2 | 6/2007 | Lintell et al. | |
| 7,249,687 B2 | 7/2007 | Anderson | |
| 7,295,890 B2 | 11/2007 | Jean-Pierre et al. | |
| 7,330,101 B2 | 2/2008 | Sekura et al. | |
| 7,343,914 B2 | 3/2008 | Abrams et al. | |
| 7,347,200 B2 | 3/2008 | Jones et al. | |
| 7,347,824 B2 | 3/2008 | Wilkinson et al. | |
| 7,366,675 B1 | 4/2008 | Walker et al. | |
| 7,383,837 B2 | 6/2008 | Robertson et al. | |
| 7,395,214 B2 | 7/2008 | Shillingburg | |
| 7,397,730 B2 | 7/2008 | Bjorlig et al. | |
| 7,424,888 B2 | 9/2008 | Lintell et al. | |
| 7,450,974 B2 | 11/2008 | Bennett et al. | |
| 7,454,267 B2 | 11/2008 | Robertson et al. | |
| 7,458,373 B2 | 12/2008 | Grollimund et al. | |
| 7,461,655 B2 | 12/2008 | Childers et al. | |
| 7,481,213 B2 | 1/2009 | Childers et al. | |
| 7,495,546 B2 | 2/2009 | Lintell | |
| 7,515,507 B2 | 4/2009 | Nanda et al. | |

(56) References Cited

U.S. PATENT DOCUMENTS

| | | | |
|---|---|---|---|
| 7,537,005 B2 | 5/2009 | Dave |
| 7,553,234 B2 | 6/2009 | Walker et al. |
| 7,554,434 B1 | 6/2009 | Gifford et al. |
| 7,639,120 B2 | 12/2009 | Sekura et al. |
| 7,675,424 B2 | 3/2010 | Debord et al. |
| 7,680,629 B2 | 3/2010 | Chang et al. |
| 7,708,697 B2 | 5/2010 | Wilkinson et al. |
| 7,766,012 B2 | 8/2010 | Scheuch et al. |
| 7,772,981 B1 | 8/2010 | Lambert et al. |
| 7,796,676 B2 | 9/2010 | Barclay et al. |
| 7,810,745 B2 | 10/2010 | Oomura et al. |
| 7,819,116 B2 | 10/2010 | Brand et al. |
| 7,821,404 B2 | 10/2010 | Bean et al. |
| 7,837,648 B2 | 11/2010 | Blair et al. |
| 7,844,361 B2 | 11/2010 | Jean-Pierre et al. |
| 7,850,618 B2 | 12/2010 | Wilkinson et al. |
| RE42,052 E | 1/2011 | Donaldson et al. |
| 7,868,609 B2 | 1/2011 | Zhitomirskiy et al. |
| 7,944,342 B2 | 5/2011 | Sekura et al. |
| 7,945,461 B2 | 5/2011 | Sekura et al. |
| 7,996,106 B2 | 8/2011 | Ervin et al. |
| 8,032,397 B2 | 10/2011 | Lawless et al. |
| 8,055,509 B1 | 11/2011 | Walker et al. |
| 8,066,432 B2 | 11/2011 | Guo et al. |
| 8,069,056 B2 | 11/2011 | Walker et al. |
| 8,091,545 B2 | 1/2012 | Schechter et al. |
| 8,092,224 B2 | 1/2012 | Bean et al. |
| 8,129,985 B2 | 3/2012 | Jones et al. |
| 8,138,939 B2 | 3/2012 | Manning et al. |
| 8,149,111 B2 | 4/2012 | Monroe et al. |
| 8,215,299 B2 | 7/2012 | Wu et al. |
| 8,225,781 B2 | 7/2012 | Ooida et al. |
| 8,231,573 B2 | 7/2012 | Edwards et al. |
| 8,240,301 B2 | 8/2012 | Spaargaren et al. |
| 8,241,223 B2 | 8/2012 | Gavriely et al. |
| 8,262,394 B2 | 9/2012 | Bean et al. |
| 8,269,613 B2 | 9/2012 | Lazar et al. |
| 8,279,076 B2 | 10/2012 | Johnson |
| 8,284,068 B2 | 10/2012 | Johnson et al. |
| 8,286,821 B2 | 10/2012 | Mejia et al. |
| 8,290,792 B2 | 10/2012 | Sekura et al. |
| 8,311,770 B2 | 11/2012 | Park et al. |
| 8,319,613 B2 | 11/2012 | Lazar et al. |
| 8,342,172 B2 | 1/2013 | Levy et al. |
| 8,353,752 B2 | 1/2013 | Walker et al. |
| 8,386,042 B2 | 2/2013 | Yudovsky et al. |
| 8,424,517 B2 | 4/2013 | Sutherland et al. |
| 8,446,799 B2 | 5/2013 | Burke et al. |
| 8,448,873 B2 | 5/2013 | Downey et al. |
| 8,456,287 B2 | 6/2013 | Gifford et al. |
| 8,464,707 B2 | 6/2013 | Jongejan et al. |
| 8,485,982 B2 | 7/2013 | Gavish et al. |
| 8,488,505 B2 | 7/2013 | Pyles et al. |
| 8,502,692 B2 | 8/2013 | Johnson |
| 8,517,016 B2 | 8/2013 | Caro et al. |
| 8,528,544 B2 | 9/2013 | Kobayashi et al. |
| 8,534,220 B1 | 9/2013 | Olson et al. |
| 8,538,707 B2 | 9/2013 | Polidoro et al. |
| 8,539,945 B2 | 9/2013 | Solomon et al. |
| 8,544,286 B2 | 10/2013 | Janssen et al. |
| 8,547,239 B2 | 10/2013 | Peatfield et al. |
| 8,549,310 B2 | 10/2013 | Walker et al. |
| 8,550,069 B2 | 10/2013 | Alelov |
| 8,560,271 B2 | 10/2013 | Koehler et al. |
| 8,573,203 B2 | 11/2013 | Addington et al. |
| 8,615,413 B2 | 12/2013 | McKee et al. |
| 8,666,539 B2 | 3/2014 | Ervin et al. |
| 8,710,827 B2 | 4/2014 | Zhitomirskiy et al. |
| 8,714,150 B2 | 5/2014 | Alelov |
| 8,714,983 B2 | 5/2014 | Kil et al. |
| 8,725,529 B2 | 5/2014 | Hyde et al. |
| 8,727,180 B2 | 5/2014 | Way et al. |
| 8,738,395 B2 | 5/2014 | Hyde et al. |
| 8,750,693 B2 | 6/2014 | Sharma et al. |
| 8,754,769 B2 | 6/2014 | Stein et al. |
| 8,771,205 B2 | 7/2014 | Gavriely et al. |
| 8,797,167 B2 | 8/2014 | Hyde et al. |
| 8,807,131 B1 | 8/2014 | Chan et al. |
| 8,823,510 B2 | 9/2014 | Downey et al. |
| 8,830,076 B2 | 9/2014 | Smith et al. |
| 8,838,738 B2 | 9/2014 | Lee et al. |
| 8,844,766 B2 | 9/2014 | Zaima et al. |
| 8,854,225 B2 | 10/2014 | Johnson |
| 8,857,617 B2 | 10/2014 | Gosselin et al. |
| 8,869,793 B1 | 10/2014 | Spandorfer et al. |
| 8,896,428 B2 | 11/2014 | Shalala et al. |
| 8,909,487 B2 | 12/2014 | Polidoro et al. |
| 8,922,367 B2 | 12/2014 | Denny et al. |
| 8,960,189 B2 | 2/2015 | Morrison |
| 8,976,036 B2 | 3/2015 | Johnson |
| 8,997,735 B2 | 4/2015 | Zierenberg et al. |
| 9,007,875 B2 | 4/2015 | Nurse et al. |
| 9,014,427 B2 | 4/2015 | Bear et al. |
| 9,027,795 B2 | 5/2015 | Ahlgren et al. |
| 9,046,403 B2 | 6/2015 | Ziemba et al. |
| 9,056,174 B2 | 6/2015 | Bradshaw et al. |
| 9,058,410 B2 | 6/2015 | McKee et al. |
| 9,072,654 B2 | 7/2015 | Pentz |
| 9,081,885 B2 | 7/2015 | Bangera et al. |
| 9,084,566 B2 | 7/2015 | Zdeblick |
| 9,125,798 B2 | 9/2015 | Stein et al. |
| 9,145,000 B2 | 9/2015 | Lakin et al. |
| 9,168,343 B2 | 10/2015 | Scarrott et al. |
| 9,174,009 B2 | 11/2015 | Peatfield et al. |
| 9,188,579 B2 | 11/2015 | Shen et al. |
| 9,216,267 B2 | 12/2015 | Spandorfer et al. |
| 9,235,689 B2 | 1/2016 | Ervin et al. |
| 9,235,690 B2 | 1/2016 | Jain et al. |
| 9,242,056 B2 | 1/2016 | Andersen et al. |
| 9,272,531 B2 | 3/2016 | Starkey et al. |
| 9,278,177 B2 | 3/2016 | Edwards et al. |
| 9,283,027 B2 | 3/2016 | Green et al. |
| 9,295,793 B2 | 3/2016 | O'Hara et al. |
| 9,308,151 B2 | 4/2016 | Soon-Shiong et al. |
| 9,308,334 B2 | 4/2016 | Smetham et al. |
| 9,311,452 B2 | 4/2016 | Dickie et al. |
| 9,314,292 B2 | 4/2016 | Trees et al. |
| 9,317,663 B2 | 4/2016 | Dickie et al. |
| 9,339,188 B2 | 5/2016 | Proud |
| 9,339,616 B2 | 5/2016 | Denny et al. |
| 9,352,107 B2 | 5/2016 | Von Hollen et al. |
| 9,358,183 B2 | 6/2016 | Stein et al. |
| 9,361,431 B2 | 6/2016 | Fauci et al. |
| 9,361,772 B2 | 6/2016 | Johnson |
| 9,361,780 B2 | 6/2016 | Tomasi et al. |
| 9,364,619 B2 | 6/2016 | Polidoro et al. |
| 9,392,939 B2 | 7/2016 | Proud |
| 9,398,854 B2 | 7/2016 | Proud |
| 9,427,534 B2 | 8/2016 | Bruin et al. |
| 9,460,265 B2 | 10/2016 | Burrows et al. |
| 9,463,291 B2 | 10/2016 | Imran |
| 9,468,729 B2 | 10/2016 | Sutherland et al. |
| 9,501,626 B2 | 11/2016 | Nathan et al. |
| 9,542,826 B2 | 1/2017 | Edwards et al. |
| 9,550,031 B2 | 1/2017 | Van Sickle et al. |
| 9,694,147 B2 | 7/2017 | Peatfield et al. |
| 9,736,642 B2 | 8/2017 | Ostrander et al. |
| 9,839,398 B2 | 12/2017 | Yamamori et al. |
| 9,911,308 B2 | 3/2018 | Edwards et al. |
| 9,956,360 B2 | 5/2018 | Germinario et al. |
| 9,962,507 B2 | 5/2018 | Germinario et al. |
| 9,962,508 B2 | 5/2018 | Bruin et al. |
| 10,016,134 B2 | 7/2018 | Hansen et al. |
| 10,046,121 B2 | 8/2018 | Kolb et al. |
| 10,155,094 B2 | 12/2018 | Wachtel et al. |
| 10,300,227 B2 | 5/2019 | Sutherland |
| 10,556,070 B2 | 2/2020 | Van Sickle et al. |
| 2001/0028308 A1* | 10/2001 | De La Huerga .. A61M 5/16827 221/9 |
| 2002/0073196 A1 | 6/2002 | Westervelt et al. |
| 2002/0185128 A1 | 12/2002 | Theobald et al. |
| 2003/0098022 A1 | 5/2003 | Nakao et al. |
| 2003/0099158 A1* | 5/2003 | De la Huerga ....... A61J 1/1437 368/10 |

(56) References Cited

U.S. PATENT DOCUMENTS

| | | |
|---|---|---|
| 2003/0192535 A1 | 10/2003 | Christrup et al. |
| 2003/0234198 A1 | 12/2003 | Weinstein et al. |
| 2004/0089299 A1 | 5/2004 | Bonney et al. |
| 2004/0117062 A1 | 6/2004 | Bonney et al. |
| 2004/0148199 A1 | 7/2004 | Dixon et al. |
| 2004/0199056 A1 | 10/2004 | Husemann et al. |
| 2005/0021286 A1 | 1/2005 | Kunce et al. |
| 2005/0028815 A1 | 2/2005 | Deaton et al. |
| 2005/0086256 A1 | 4/2005 | Owens et al. |
| 2005/0119604 A1 | 6/2005 | Bonney et al. |
| 2005/0150488 A1 | 7/2005 | Dave et al. |
| 2005/0161467 A1 | 7/2005 | Jones et al. |
| 2005/0172958 A1 | 8/2005 | Singer et al. |
| 2005/0247312 A1 | 11/2005 | Davies et al. |
| 2005/0251289 A1 | 11/2005 | Bonney et al. |
| 2006/0089545 A1 | 4/2006 | Ratjen et al. |
| 2006/0231109 A1 | 10/2006 | Howell et al. |
| 2006/0237001 A1 | 10/2006 | Stangl et al. |
| 2006/0237002 A1 | 10/2006 | Bonney et al. |
| 2006/0241510 A1 | 10/2006 | Halperin et al. |
| 2007/0023034 A1 | 2/2007 | Jongejan et al. |
| 2007/0118054 A1 | 5/2007 | Pinhas et al. |
| 2007/0186923 A1 | 8/2007 | Poutiatine et al. |
| 2007/0271298 A1 | 11/2007 | Juang et al. |
| 2008/0114490 A1 | 5/2008 | Jean-Peirre |
| 2008/0125724 A1 | 5/2008 | Monroe et al. |
| 2008/0173301 A1 | 7/2008 | Deaton et al. |
| 2008/0201169 A1 | 8/2008 | Galasso et al. |
| 2008/0230057 A1* | 9/2008 | Sutherland .......... A61M 15/009 128/202.13 |
| 2008/0269625 A1 | 10/2008 | Halperin et al. |
| 2008/0281636 A1 | 11/2008 | Jung et al. |
| 2009/0128330 A1 | 5/2009 | Monroe et al. |
| 2009/0194104 A1 | 8/2009 | Van et al. |
| 2009/0221308 A1 | 9/2009 | Lerner et al. |
| 2009/0308387 A1 | 12/2009 | Andersen et al. |
| 2009/0314292 A1 | 12/2009 | Overfield et al. |
| 2009/0326861 A1 | 12/2009 | Langford et al. |
| 2010/0164716 A1 | 7/2010 | Estevez et al. |
| 2010/0192948 A1 | 8/2010 | Sutherland et al. |
| 2010/0242960 A1 | 9/2010 | Zangerle et al. |
| 2010/0250280 A1 | 9/2010 | Sutherland et al. |
| 2010/0252036 A1 | 10/2010 | Sutherland et al. |
| 2011/0253139 A1 | 10/2011 | Guthrie et al. |
| 2011/0282693 A1 | 11/2011 | Craft |
| 2012/0123842 A1 | 5/2012 | Patel et al. |
| 2012/0173319 A1 | 7/2012 | Ferrara et al. |
| 2012/0232983 A1 | 9/2012 | Bertha et al. |
| 2012/0245960 A1 | 9/2012 | Bartholomew et al. |
| 2013/0053719 A1* | 2/2013 | Wekell .............. A61M 15/008 600/538 |
| 2013/0096843 A1 | 4/2013 | Yuen et al. |
| 2013/0137998 A1 | 5/2013 | Lange et al. |
| 2013/0144178 A1 | 6/2013 | Halperin et al. |
| 2013/0151196 A1 | 6/2013 | Yuen et al. |
| 2013/0245502 A1 | 9/2013 | Lange et al. |
| 2013/0269685 A1 | 10/2013 | Jung et al. |
| 2013/0269694 A1 | 10/2013 | Patton et al. |
| 2013/0304502 A1 | 11/2013 | Cederlund et al. |
| 2013/0325396 A1 | 12/2013 | Yuen et al. |
| 2013/0325399 A1 | 12/2013 | Yuen et al. |
| 2013/0325404 A1 | 12/2013 | Yuen et al. |
| 2014/0000598 A1 | 1/2014 | Sutherland et al. |
| 2014/0012099 A1 | 1/2014 | Halperin et al. |
| 2014/0039839 A1 | 2/2014 | Yuen et al. |
| 2014/0039840 A1 | 2/2014 | Yuen et al. |
| 2014/0039841 A1 | 2/2014 | Yuen et al. |
| 2014/0039842 A1 | 2/2014 | Yuen et al. |
| 2014/0052790 A1 | 2/2014 | Yuen et al. |
| 2014/0065219 A1 | 3/2014 | Bosch et al. |
| 2014/0106324 A1 | 4/2014 | Adams et al. |
| 2014/0155841 A1 | 6/2014 | Dossin et al. |
| 2014/0182584 A1 | 7/2014 | Sutherland et al. |
| 2014/0207204 A1 | 7/2014 | Halperin et al. |
| 2014/0213925 A1 | 7/2014 | Chan et al. |
| 2015/0193597 A1 | 7/2015 | Cederlund |
| 2015/0283341 A1 | 10/2015 | Adams et al. |
| 2016/0042154 A1 | 2/2016 | Goldberg et al. |
| 2016/0082208 A1 | 3/2016 | Ballam et al. |
| 2016/0103966 A1 | 4/2016 | Mirza et al. |
| 2016/0128389 A1 | 5/2016 | Lamb et al. |
| 2016/0166766 A1 | 6/2016 | Schuster et al. |
| 2016/0228657 A1 | 8/2016 | Sutherland |
| 2016/0256639 A1 | 9/2016 | Van Sickle et al. |
| 2016/0314256 A1 | 10/2016 | Su et al. |
| 2017/0079557 A1 | 3/2017 | Lauk |
| 2017/0109493 A1 | 4/2017 | Hogg et al. |
| 2017/0140125 A1 | 5/2017 | Hogg et al. |
| 2017/0164892 A1 | 6/2017 | Sezan et al. |
| 2017/0173279 A1 | 6/2017 | Sutherland et al. |
| 2017/0246406 A1 | 8/2017 | Sutherland |
| 2017/0258993 A1 | 9/2017 | Pizzochero et al. |
| 2017/0262613 A1 | 9/2017 | Ljungberg |
| 2017/0270260 A1* | 9/2017 | Shetty .................... G16H 40/67 |
| 2017/0325734 A1 | 11/2017 | Sutherland et al. |
| 2017/0363673 A1 | 12/2017 | Mukherjee |
| 2018/0011988 A1 | 1/2018 | Ziegler et al. |
| 2018/0052964 A1 | 2/2018 | Adelson |
| 2018/0085540 A1 | 3/2018 | Dantsker et al. |
| 2018/0125365 A1 | 5/2018 | Hunter et al. |
| 2018/0161530 A1 | 6/2018 | Ganton et al. |
| 2021/0074402 A1 | 3/2021 | Levin |

FOREIGN PATENT DOCUMENTS

| | | |
|---|---|---|
| CN | 205073444 U | 3/2016 |
| CN | 205073448 U | 3/2016 |
| EP | 1135056 B1 | 8/2006 |
| EP | 1688746 A2 | 8/2006 |
| EP | 1736133 A2 | 12/2006 |
| EP | 1970087 A2 | 9/2008 |
| EP | 1992381 A1 | 11/2008 |
| EP | 1423046 B1 | 1/2010 |
| EP | 2186471 A1 | 5/2010 |
| EP | 2384782 A1 | 11/2011 |
| EP | 3228345 A1 | 10/2017 |
| FR | 2987997 A1 | 9/2013 |
| WO | 9522365 A1 | 8/1995 |
| WO | 9838909 A1 | 9/1998 |
| WO | 9953982 A1 | 10/1999 |
| WO | 9963901 A1 | 12/1999 |
| WO | 0002779 A1 | 1/2000 |
| WO | 0032088 A1 | 6/2000 |
| WO | 0124690 A2 | 4/2001 |
| WO | 0126020 A1 | 4/2001 |
| WO | 0200280 A2 | 1/2002 |
| WO | 02053022 A2 | 7/2002 |
| WO | 03063754 A1 | 8/2003 |
| WO | 03073977 A2 | 9/2003 |
| WO | 2004084116 A1 | 9/2004 |
| WO | 2005028008 A1 | 3/2005 |
| WO | 2006068623 A1 | 6/2006 |
| WO | 2009003989 A1 | 1/2009 |
| WO | 2010098927 A1 | 9/2010 |
| WO | 2011135353 A1 | 11/2011 |
| WO | 2012095829 A2 | 7/2012 |
| WO | 2012110700 A1 | 8/2012 |
| WO | 2013126897 A1 | 8/2013 |
| WO | 2015002492 A1 | 1/2015 |
| WO | 2016043601 A1 | 3/2016 |
| WO | 2017005605 A1 | 1/2017 |
| WO | 2017051389 A1 | 3/2017 |
| WO | 2017129521 A1 | 8/2017 |
| WO | 2017141194 A1 | 8/2017 |
| WO | 2017176693 A1 | 10/2017 |
| WO | 2017176704 A1 | 10/2017 |
| WO | 2017180980 A1 | 10/2017 |
| WO | 2017189712 A1 | 11/2017 |
| WO | 2018128976 A1 | 7/2018 |

(56) References Cited

FOREIGN PATENT DOCUMENTS

| WO | 2018134552 A1 | 7/2018 |
|---|---|---|
| WO | 2018134553 A1 | 7/2018 |

OTHER PUBLICATIONS

Varshney 2011, "Wireless Medication Management System: Design and performance evaluation," 2011 Wireless Telecommunications Symposium (WTS), New York, NY, USA, 2011, pp. 1-8, doi: 10.1109/WTS.2011.5960858.*

Bateman, et al., "Can Guideline-Defined Asthma Control be Achieved? The Gaining Optimal Asthma Control Study", Am. J. Respir. Crit. Care Med., vol. 170, No. 8, Jan. 1, 2004 00:00:00.0, pp. 836-844.

Doser, "Doser™ Product Description", Available at https://www.doser.com/dWhat.html, retrieved on Jun. 22, 2017, Jan. 1, 1999 00:00:00.0, 2 pages.

Frey, et al., "Complexity of Chronic Asthma and Chronic Obstructive Pulmonary Disease: Implications for Risk Assessment, and Disease Progression and Control", Lancet, vol. 372, No. 9643, Jan. 1, 2008 00:00:00.0, pp. 1088-1099.

Isonea, "Technology", Available at https://web.archive.org/web/20131012033714/http:/isoneamed.com/products/productstechnolog, Jan. 1, 2011 00:00:00.0, 3 pages.

Miller, "Attacking Asthma with Advanced Telehealth Monitoring", AT&T, http://www.research.att.com/articles/featured_stories/2012_12/201212_asthma_VOC_detector.html?fbid=5Z7y-IAVNCi, Dec. 17, 2012 00:00:00.0, 3 pages.

Moorman, et al., "National Surveillance for Asthma", Morbidity and Mortality Weekly Report. US, vol. 56, No. SS-8, Jan. 1, 2007 00:00:00.0, 57 pages.

Nathan, et al., "Development of the Asthma Control Test: A Survey for Assessing Asthma Control", J. Allergy Clin. Immunol, vol. 113, No. 1, Jan. 1, 2004 00:00:00.0, pp. 59-65.

National Heart, Lung, and Blood, "Expert Panel Report 3: Guidelines for the Diagnosis and Management of Asthma Full Report", Full Report, U.S, Aug. 28, 2007 00:00:00.0, 440 pages.

Nike, "Nike+ Fuelband", Available at https://web.archive.org/web/20130106020727/http://www.nike.com/us/en_us/lp/nikeplusfuelband, Jan. 1, 2012 00:00:00.0, 17 pages.

Propeller Health, "How It Works", Available at http://propellerhealth.com/solutions/, Jan. 1, 2013 00:00:00.0, 5 pages.

Propeller Health, "Patients", Available at http://propellerhealth.com/solutions/patients, Jan. 1, 2013 00:00:00.0, 5 pages.

Propeller Health, "Payers", Available at http://propellerhealth.com/solutions/payers, Jan. 1, 2013 00:00:00.0, 5 pages.

Propeller Health, "Providers", Available at http://propellerhealth.com/solutions/providers, Jan. 1, 2013 00:00:00.0, 4 pages.

Smartinhaler, "Smartinhaler Tracker", Available at https://web.archive.org/web/20130125222221/http:/www.smartinhaler.com/clinical/products/smartinhalertracker.aspx, Jan. 1, 2011 00:00:00.0, 1 page.

Tsai, P., et al., "Smart Medication Dispenser: Design, Architecture and Implementation", IEEE Systems Journal, vol. No. 5, No. 1, Mar. 2011, 99-110.

* cited by examiner

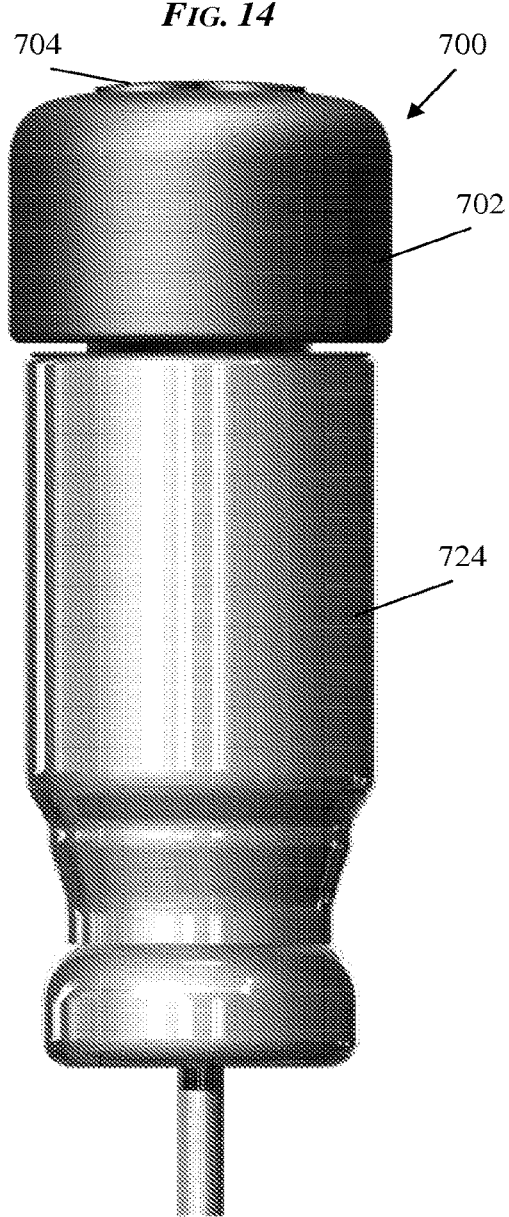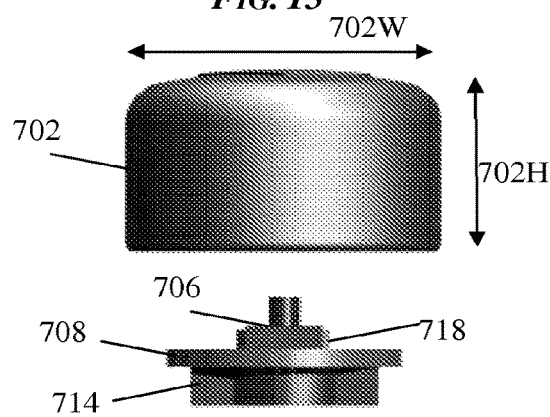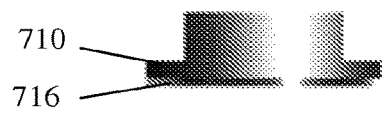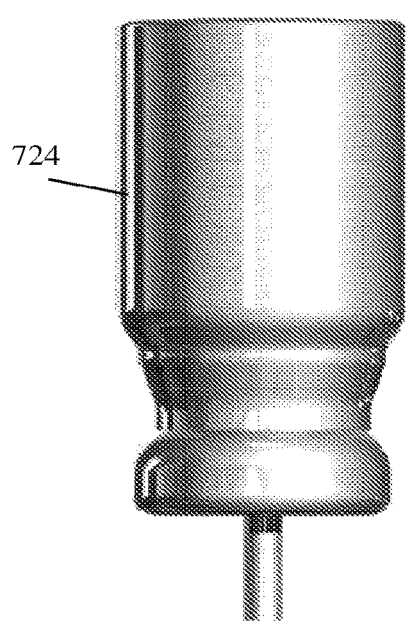

DEVICES, SYSTEMS, AND METHODS FOR ADHERENCE MONITORING AND PATIENT INTERACTION

CROSS REFERENCE TO RELATED APPLICATIONS

The present application is a continuation of U.S. patent application Ser. No. 14/375,696, filed Jul. 30, 2014, which claims priority to International Application No. PCT/US2013/047507 entitled "Devices Systems, And Methods for Adherence Monitoring and Patient Interaction", filed Jun. 25, 2013, and to U.S. Provisional Patent Application No. 61/664,008 entitled "System for Adherence Monitoring and Patient Interaction" filed on Jun. 25, 2012, which are hereby incorporated by reference in their entireties.

FIELD OF THE INVENTION

The present invention relates generally to devices, systems, and methods for adherence monitoring and patient interaction.

BACKGROUND OF THE INVENTION

Asthma is the most common chronic disease and is one of the leading causes of hospitalization for American children. Nearly ten million—or one in seven—kids in America are affected by asthma. Worrisome for children and parents alike, asthma is also a pressing public health issue, costing the U.S. over $15 billion annually. Asthma is also a serious concern for adults in the U.S. and for both adults and children outside the U.S. Additionally, air quality problems throughout the world, particularly in large, congested cities, can exacerbate asthma and other respiratory problems and can generally increase the prevalence of and the need for treating such respiratory health issues.

Inhaled maintenance medication, e.g., corticosteroids, can effectively control asthma symptoms. Such medication is typically prescribed for administration on a regular, usually daily, schedule. The closer a patient adheres to the medication schedule, the better the patient's condition can be managed, e.g., because adequate amounts of the medication can be consistently present in the patient's system to consistently control adverse effects of the asthma. Medications other than those for asthma treatment, such as for other respiratory conditions, for dermatological issues, for cardiac issues, etc., can also be prescribed for dosage on a regular schedule and can have their maximized effectiveness if taken on the regular schedule.

It can be difficult for patients to adhere to their medication treatment schedule for a variety of reasons, such as unfamiliarity with a new medication treatment schedule, being busy with an activity such as work, school, napping, or athletics, and simply forgetting to take the medication on schedule. It can be particularly difficult for children to remember to take their medication on schedule, particularly if any medication doses are required while a child is away from their parent or guardian, such as during school or while at summer camp. Non-adherence to a prescribed schedule of medication can cause any number of adverse effects, such as unnecessary exacerbations, repeating symptoms, required doses of emergency treatment medication, and/or hospital emergency room visits. Adhering to a medication schedule can thus help better maintain a patient's health, help reduce instances of emergency medication administration, and/or help reduce health care costs by requiring fewer emergency hospital visits or other medical practitioner consultations.

Accordingly, there remains a need for improved devices, systems, and methods for adherence monitoring and patient interaction.

SUMMARY OF THE INVENTION

In one embodiment, an apparatus is provided that includes a mechanical accessory attached to a medication dispenser containing a medication that is dispensable to a patient. The accessory can include a processor configured to cause the accessory to provide a notification to the patient when a dosage of the medication is due according to a predetermined medication schedule, a sensor configured to sense when the medication is dispensed to the patient, a memory, and a wireless communication mechanism. The sensing of the medication being dispensed can trigger the processor to store data in the memory regarding dispensing of the medication. The processor can be configured to cause the wireless communication mechanism to wirelessly transmit the stored data to an external device that is external to the accessory and the medication dispenser.

The stored data can include at least one of a date and time when the medication was dispensed, a time elapsed between consecutive dispensing of the medication, a time elapsed between dispensing of the medication and the transmitting to an external device, orientation of the medication dispenser when the medication was dispensed, a temperature of the medication when the medication was dispensed, movement of the medication dispenser when the medication was dispensed, and an amount of the medication dispensed.

The processor can be configured to cause the wireless communication mechanism to wirelessly transmit the stored data in response to a data request received from the external unit, and/or the processor can be configured to cause the wireless communication mechanism to automatically wirelessly transmit the stored data to the external unit in real time with the sensing of the medication being dispensed.

The notification can include at least one of an illuminated light, an audible sound, a vibration, a change in temperature of the accessory, a text message, an email message, and a phone call.

When the medication is not dispensed within a predetermined period of time after the notification is provided, the processor can be configured to cause a missed dosage notation to be saved in the memory. The wireless communication mechanism can be configured to wirelessly transmit the stored missed dosage notation to an external device.

When the medication is not dispensed within a predetermined period of time after the notification is provided, the processor can be configured to cause the accessory to provide an alarm. The alarm can include at least one of an illuminated light, an audible sound, a vibration, a change in temperature of the accessory, a text message, an email message, and a phone call.

The sensor can include at least one of a button configured to be manually depressed, a motion sensor configured to sense movement of the mechanical accessory, a pH sensor configured to sense a pH at a location where the medication is dispensed from the medication dispenser, a temperature sensor configured to sense a temperature of the medication dispenser, and an audio sensor configured to sense a sound of medication dispensing.

The accessory can vary in any number of ways. For example, the accessory can be configured to be removably and replaceably attached to the medication dispenser, or the accessory can be integrally attached to the medication dispenser. For another example, the medication dispenser can include a respiratory inhaler, and the accessory can include a cap removably and replaceably attached to a portion of the inhaler that is depressible by a user so as to dispense the medication such that depressing the cap causes the medication to be dispensed. For another example, the accessory can be removably and replaceably attached to the medication dispenser by at least one of press fit, a magnet, Velcro®, a guide track, a clip, and a strap. For yet another example, the accessory can be configured to be pressed so as to cause the medication to be dispensed. For another example, the accessory can include a power source configured to provide power for the sensor, for the storage of the data, and for the wireless transmission.

In another aspect, a system is provided that in one embodiment includes the provided apparatus and external device. The external device can be configured to generate a report based on the data received from the accessory regarding a plurality of times the medication is dispensed, and the external device can be configured to provide the report to a user. The user can include at least one of the patient, a family member of the patient, and a care provider for the patient.

The system can have any number of variations. For example, the report can include at least one of a summary of the patient's adherence to the predetermined medication schedule, a prediction of changes in the patient's health, a prediction of the patient's future adherence to the predetermined medication schedule, a log of the patient's missed dosages, a log indicating any times a second medication is dispensed off the predetermined medication schedule, a log of successful attempts of the wireless communication mechanism wirelessly communicating data to the external device, and a comparison of the patient's adherence to the predetermined medication schedule with a plurality of other patients' adherence with their respective predetermined medication schedules.

In another embodiment, an apparatus is provided that includes a mechanical accessory attached to a medication dispenser containing a medication that is dispensable to a patient. The accessory can include a sensor configured to sense when the medication is dispensed to the patient, a processor, a memory, and a power source. The sensing of the medication being dispensed can trigger the processor to store data in the memory regarding dispensing of the medication. The power source can have a first state in which the power source does not provide adequate power to the processor to allow data to be stored in the memory, and a second state in which the power source does provide adequate power to the processor to allow data to be stored in the memory. The power source can be configured to move from the first state to the second state in response to the sensor sensing the medication being dispensed, and the power source can be configured to move from the second state to the first state in response to storage of the data in the memory.

The accessory can be configured to be removably and replaceably attached to the medication dispenser, or the accessory can be integrally attached to the medication dispenser.

The accessory can include a timer configured to track passage of time and determine based on the tracked time when a dosage of the medication is due according to a predetermined medication schedule, and a notification mechanism configured to provide a notification to the patient when the dosage of the medication is due. The power source in the first state and in the second state can be configured to continuously provide power to the timer, and the power source can be configured to only provide power to the notification mechanism in the second state so as to allow the notification mechanism to provide the notification. The notification can include at least one of an illuminated light, an audible sound, a vibration, a change in temperature of the accessory, a text message, an email message, and a phone call.

The accessory can include a wireless communication mechanism configured to wirelessly transmit data stored in the memory to an external device that is external to the accessory and the medication dispenser. The power source in the first state can not provide adequate power to the wireless communication mechanism to allow the wireless communication mechanism to wirelessly transmit data. The power source in the second state can provide adequate power to the wireless communication mechanism to allow the wireless communication mechanism to wirelessly transmit data. The power source in the second state can be configured to provide all power for the wireless transmission by the wireless communication mechanism. The power source can be configured to move from the first state to a third state in response to a request for data from the external device. The power source in the third state can be configured to provide adequate power to the wireless communication mechanism to allow the wireless communication mechanism to wirelessly transmit data to the external device in response to the request for data. The power source can be configured to move from the third state to the first state in response to the wireless communication mechanism wirelessly transmitting data to the external device in response to the request for data.

The medication dispenser can include a respiratory inhaler, and the accessory can include a cap removably and replaceably attached to a portion of the inhaler that is depressible by a user so as to dispense the medication such that depressing the cap causes the medication to be dispensed.

In another aspect, a system is provided that includes the provided apparatus and external device. The accessory can include a wireless communication mechanism configured to wirelessly transmit data stored in the memory to an external device that is external to the accessory and the medication dispenser, and the external device can be configured to provide all power for the wireless transmission by the wireless communication mechanism. The system can have any number of variations.

In another embodiment, a system is provided that includes a mechanical accessory and a processor. The accessory can be attached to a medication dispenser containing a medication that is dispensable to a patient. The processor can be configured to cause the accessory to provide a notification to the patient when a dosage of the medication is due according to a predetermined medication schedule, log each instance of the medication being dispensed from the dispenser, determine the patient's compliance with the predetermined medication schedule based on the logged instances, and cause a report indicating the patient's compliance to be provided on a display screen.

The system can vary in any number of ways. For example, the accessory can be configured to be removably and replaceably attached to the medication dispenser, or the accessory can be integrally attached to the medication dispenser. For another example, the notification can include at least one of an illuminated light, an audible sound, a vibration, a change in temperature of the accessory, a text message, an email message, and a phone call. For another example, the report can indicate when the medication is not dispensed within a predetermined period of time after the notification is provided. The medication not being dispensed within the predetermined period of time can indicate a lack of compliance with the predetermined medication schedule. For yet another example, the report can indicate when the medication is dispensed at a date and time inconsistent with the predetermined medication schedule. For another example, the report can indicate at least one of a prediction of changes in the patient's health based on the patient's compliance, a prediction of the patient's future adherence to the predetermined medication schedule based on the patient's compliance, and a comparison of the patient's compliance with a plurality of other patients' compliance with their respective predetermined medication schedules. For still another example, the processor can be included in the accessory. For another example, the processor can be included in an external device external to the accessory and the medication dispenser. For another example, the processor can include a first processor included in the accessory and a second processor included in an external device external to the accessory and the medication dispenser. The first processor can be configured to cause the accessory to provide the notification to the patient and to log the instances, and the second processor can be configured to cause the report to be provided on the display screen. For yet another example, the medication dispenser can include a respiratory inhaler, and the accessory can include a cap removably and replaceably attached to a portion of the inhaler that is depressible by a user so as to dispense the medication such that depressing the cap causes the medication to be dispensed.

In another embodiment, a system is provided that includes a mechanical accessory and a processor. The accessory can be attached to a medication dispenser containing a medication that is dispensable to a patient. The processor can be configured to log a date and time for each instance of the medication being dispensed from the dispenser based on an actuation of the accessory, determine the patient's compliance with a predetermined medication schedule based on the logged dates and times, and cause a report indicating the patient's compliance to be provided on a display screen. The report can indicate a progress of the patient toward a goal level of compliance with the predetermined medication schedule.

The system can have any number of variations. For example, the accessory can be configured to be removably and replaceably attached to the medication dispenser, or the accessory can be integrally attached to the medication dispenser. For another example, the report can be customized for a user based on a category of the user, the category being one of the patient, a family member of the patient, and a care provider for the patient. For another example, the processor can be configured to trigger a reward for the patient when the patient reaches the goal level of compliance. The reward can include at least one of a virtual reward for the patient and a physical reward for the patient. For yet another example, the goal level of compliance can be based on a number of times the medication is dispensed within a predetermined amount of time after a dosage of medication is due as indicated by the predetermined medication schedule. For another example, the processor can be configured to cause the accessory to provide a notification to the patient when a dosage of the medication is due according to the predetermined medication schedule. The progress of the patient toward the goal level of compliance can be based on the medication being dispensed within a predetermined time period after the notification is provided. For another example, the processor can be included in the accessory. For yet another example, the processor can be included in an external device external to the accessory and the medication dispenser. For still another example, the processor can include a first processor included in the accessory and a second processor included in an external device external to the accessory and the medication dispenser. The first processor can be configured to log the date and time, and the second processor can be configured to cause the report to be provided on the display screen. For another example, the medication dispenser can include a respiratory inhaler, and the accessory comprises a cap removably and replaceably attached to a portion of the inhaler that is depressible by a user so as to dispense the medication such that depressing the cap causes the medication to be dispensed.

In another aspect, a method for providing and communicating data regarding medication administration is provided that in one embodiment includes causing a mechanical accessory to provide a notification to a patient when a dosage of medication is due according to a predetermined medication schedule. The accessory can include a sensor and a memory. The method can also include sensing with the sensor when the medication is dispensed to the patient. The sensing can trigger data to be stored in the memory regarding the dispensing of the medication. The method can also include wirelessly transmitting the stored data to an external device that is external to the accessory and the medication dispenser. The method can have any number of variations.

In another embodiment, a method for providing and communicating data regarding medication administration is provided that includes causing a mechanical accessory attached to a medication dispenser to provide a notification to a patient when a dosage of medication contained in the dispenser is due according to a predetermined medication schedule, logging each instance of the medication being dispensed from the dispenser, determining the patient's compliance with the predetermined medication schedule based on the logged instances, and causing a report indicating the patient's compliance to be provided on a display screen. The method can have any number of variations.

In another aspect, a method for managing power supplied to a mechanical accessory attached to a medication dispenser is provided that in one embodiment includes, in response to medication being dispensed from a medication dispenser having a mechanical accessory attached thereto, moving a power source of the accessory from a first state to a second state. The power source in the first state can not provide adequate power to a processor of the accessory to allow data to be stored in a memory of the accessory, and the power source in the second state can provide adequate power to the processor to allow data to be stored in the memory. The method can also include, with the power source in the second state, storing data in the memory regarding the dispensing of the medication, and, in response to storage of the data in the memory, moving the power source from the second state to the first state. The method can have any number of variations.

In another aspect, a method for managing data regarding medication administration is provided that in one embodiment includes logging a date and time for each instance of medication being dispensed from a medication dispenser to a patient based on an actuation of a mechanical accessory attached to the medication dispenser, determining the patient's compliance with a predetermined medication schedule based on the logged dates and times, and causing a report indicating the patient's compliance to be provided on a display screen. The report can indicate a progress of the patient toward a goal level of compliance with the predetermined medication schedule. The method can have any number of variations.

BRIEF DESCRIPTION OF THE DRAWINGS

The invention will be more fully understood from the following detailed description taken in conjunction with the accompanying drawings, in which:

FIG. 14 is a side view of a medication-containing canister of a medication dispenser, and an accessory removably and replaceably attached to the canister;

FIG. 15 shows another side view of the canister of FIG. 14 and a side expanded view of the accessory of FIG. 14;

DETAILED DESCRIPTION OF THE INVENTION

Figure 1:
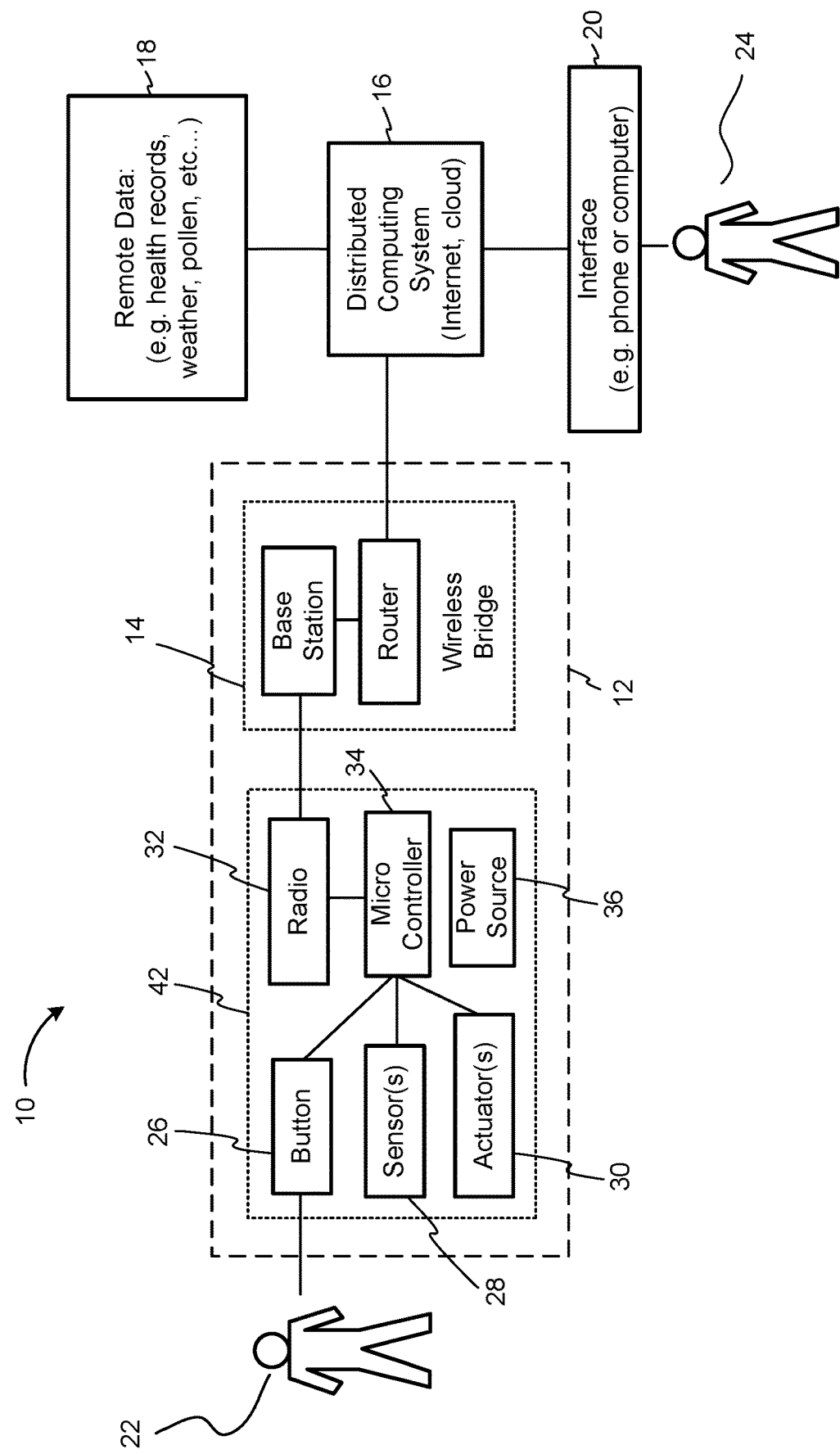
FIG. 1 is a schematic view of one embodiment of a medication administration, management, and review system.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will appreciate that an equivalent to such linear and circular dimensions can be easily determined for any geometric shape.

Various exemplary devices, systems, and methods are provided for adherence monitoring and patient interaction. In general, the devices, systems, and methods can facilitate a patient's adherence to a medication schedule and can facilitate monitoring and tracking of the patient's adherence to the medication schedule. The devices, systems, and methods can allow data regarding the patient's historical adherence to the medication schedule to be accessible via a computer system. A user such as the patient, the patient's family, the patient's care provider, a director of a clinical trial involving the patient, etc. can thus access the adherence data even when remotely located from the patient, which can facilitate evaluation and/or modification of the patient's treatment, facilitate evaluation and/or modification of the clinical trial involving the patient, and/or can facilitate incentivizing the patient to adhere to the medication schedule.

In one embodiment, a medical accessory such as a cap is provided that can be configured to attach to existing medication dispensers, such as asthma inhalers, or to be integrated into a custom-made medication dispenser. The cap can include a notification mechanism such as a light source (e.g., a light emitting diode (LED)) configured to light up when the next dose (also referred to herein as a "dosage") of medication is due, a speaker configured to provide an audible sound when the next dose of medication is due, a vibration mechanism configured to vibrate when the next dose of medication is due, and a temperature-changing element configured to increase or decrease in temperature when the next dose of medication is due. The cap can include an on-board timer configured to trigger the notification mechanism to provide a notification, e.g., light, sound, vibration, etc. The cap can also include a power source, e.g., a battery, configured to power the timer and the notification mechanism. The notification can help patients of any age more easily adhere to their medication schedule. Ailments such as asthma can therefore be better regulated through maintenance treatment, and patients can be less likely to need to resort to unscheduled, emergency treatments, such as use of a rescue inhaler. The cap can include a button configured to detect usage of the dispenser by being pressed down when medication is dispensed from the dispenser so as to "wake up" a processor coupled to the cap. In response to actuation of the button, the processor can be configured to record the date and time of the dispenser's usage in a storage unit, such as an on-board memory. The stored data can be transmitted to an external source, e.g., computer system, that can store the data in a network cloud, where the data can be accessed via a user interface, such as a web interface. The user interface can allow a user to view and/or analyze the patient's medication usage trends. The user interface can be customized for different patient age groups (e.g., children v. adults) and for different users (e.g., patients, parents, doctors, etc.), thereby allowing different users to view and analyze data most effective for their needs and goals, even when the user is remotely located from the patient. The user interface can include a customizable rewards system for patients, parents, and care providers based on adherence to a prescribed medication schedule, which can be particularly effective in encouraging children to regularly take their medication as directed.

The accessory can be, but is not limited to, use with asthma medication. The accessory can be configured to be used in any adherence/compliance application for medication, such as creams for dermatology patients, inhalers for non-asthma respiratory ailments, pill bottles, and medicament tubes.

FIG. 1 illustrates one exemplary embodiment of a system 10 configured to facilitate adherence monitoring and patient interaction. The system 10 can include a mechanical accessory 12 (also referred to herein as an "accessory"), a wireless bridge 14, a network 16 (also referred to herein as a "distributed computing system"), a memory 18, and an interface 20 (also referred to herein as a "computer system" and a "client station"). In general, the accessory 12 can be attached to a medication dispenser (not shown) configured to dispense a medication disposed therein. The medication dispenser can include any of a variety of dispensers, such as an asthma inhaler, an inhaler for a non-asthma respiratory ailment, a liquid or semi-liquid dispenser such as a medicament tube or pump such as for a topical cream or a topical gel, and a pill bottle. The accessory 12 can be configured to provide a notification to a patient 22 when medication from the dispenser is due according to a predetermined medication schedule. The accessory 12 can be configured to detect usage of the dispenser so as to determine when medication has been dispensed from the dispenser. The accessory 12 can be configured to provide data regarding dispensing of the medication to an external device, such as the interface 20. The data can be transmitted from the accessory 12 to the interface 20 using wireless communication, e.g., Bluetooth, WiFi, etc., over the network 16, e.g., the Internet, a cloud, a local area network (LAN), etc., via the wireless bridge 14. However, as will be appreciated by a person skilled in the art, the system 10 need not include the wireless bridge 14 if the accessory 12 is configured to communicate over the network 16 using a wired connection instead of a wireless connection. The data communicated to the interface 20 from the accessory 12 can optionally be supplemented with data stored in and transmitted from the memory 18, such as health record data for the patient 22 (e.g., complete electronic health record (EHR) of the patient 22, patient name, patient age, patient medical record number, other medications being taken by the patient 22, identities of care providers for the patient 22, medical diagnoses of the patient 22, data for the patient 22 previously transmitted by the accessory 12, geographic home of the patient 22, etc.) and environmental data (which can be helpful in analyzing data for asthma and other respiratory ailments) such as weather data, traffic data, dust data, and pollen data. Similarly, data transmitted to the memory 18 can be stored therein so as to be associated with a patient record already stored therein, e.g., data gathered by the accessory 12 being added to the patient's EHR stored in the memory 18. The interface 20 can be configured to analyze the data received from the accessory 12 and can be configured to provide the received data and/or results of the analysis on a user interface (not shown) for review by one or more users such as the patient 22 and a user 24 associated with the patient 22, such as a family member of the patient 22, a friend of the patient 22, or a medical care provider (doctor, nurse, clinical trial director, etc.) for the patient 22. In an exemplary embodiment, the user interface can be customized based on an identity of the user accessing the interface 20.

Figure 2:
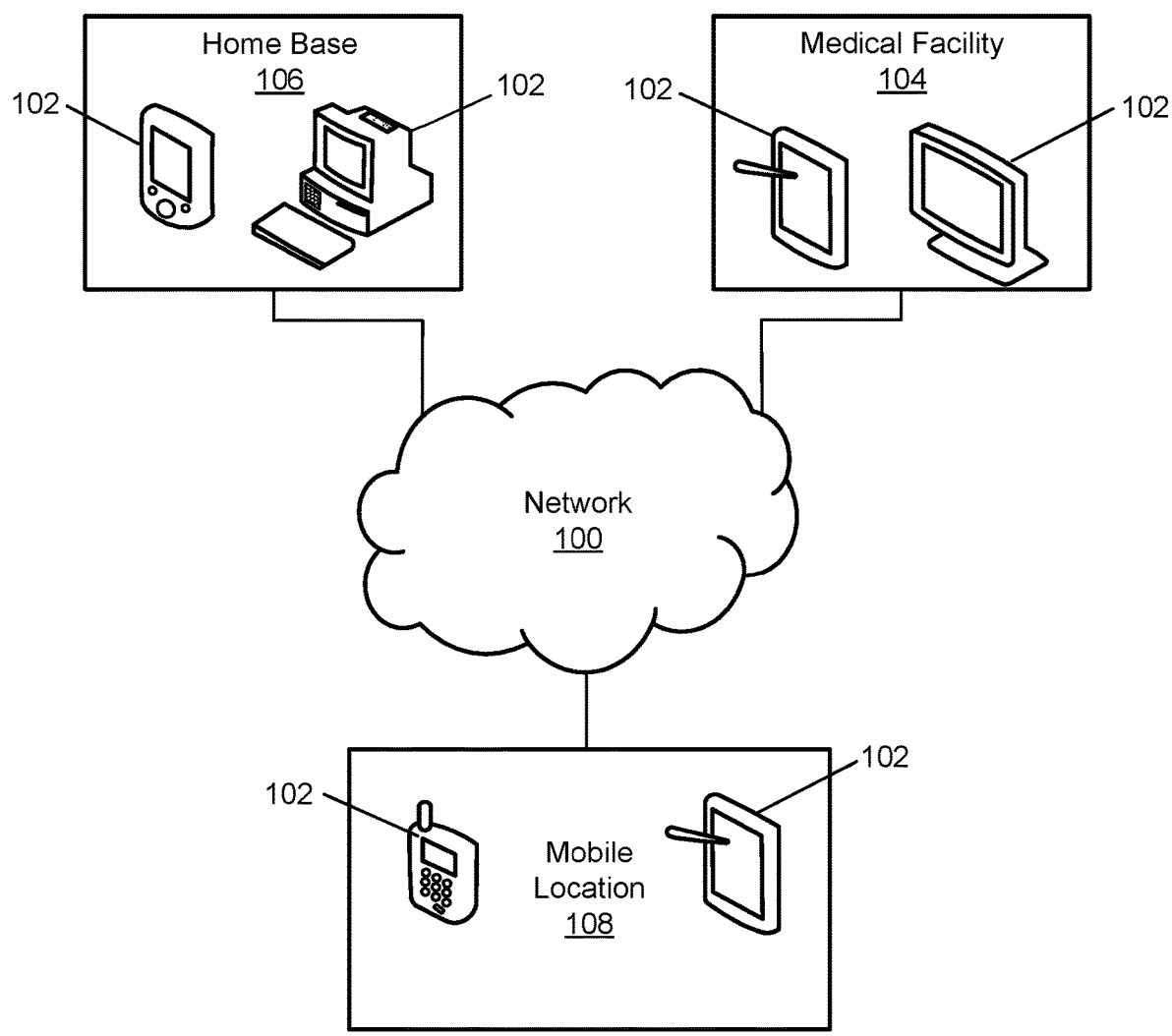
FIG. 2 is a schematic view of one embodiment of a network system including the system of FIG. 1.

Any of a variety of users can access, interact with, control, etc. a user interface from any of a variety of locations. For example, as shown in an embodiment illustrated in FIG. 2, the user interface can be accessible over a network 100 (e.g., over the Internet via cloud computing) from any number of client stations 102 in any number of locations such as a medical facility 104 (e.g., a hospital, an operating room (OR), a nurse's station, a medical device distribution facility, a medical device company, a hospital's sterilization, records, or billing departments, etc.), a home base 106 (e.g., a patient's home or office, a surgeon's home or office, etc.), a mobile location 108, and so forth. The client station(s) 102 can access the user interface through a wired and/or wireless connection to the network 100 such that the user interface is displayed on a display screen thereof, e.g., an LCD (liquid-crystal display), ePaper, a touch screen, etc. In an exemplary embodiment, at least some of the client station(s) 102 can access the user interface wirelessly, e.g., through WiFi connection(s), which can facilitate accessibility of the user interface from almost any location in the world. Data can be transmitted wirelessly using an existing protocol such as 802.11 or a proprietary protocol, e.g., a protocol that optimizes power, data, and range for a particular use more than an existing protocol. As shown in FIG. 2, the medical facility 104 includes client stations 102 in the form of a tablet and a computer touch screen, the home base 106 includes client stations 102 in the form of a mobile phone having a touch screen and a desktop computer, and the mobile location 108 includes client stations 102 in the form of a tablet and a mobile phone, but the medical facility 104, the home base 106, and the mobile location 108 can include any number and any type of client stations. In an exemplary embodiment, the user interface can be accessible by an interface via a web address and/or a client application (also referred to herein as an "app").

It will be appreciated that the user interface can be accessible using one or more security features such that the aspects of the user interface available to any particular user can be determined based on the identity of the user and/or the location from which the user is accessing the user interface. To that end, each user can have a unique username, password, and/or other security credentials to facilitate access to the user interface. The received security parameter information can be checked against a database of authorized users to determine whether the user is authorized and to what extent the user is permitted to interact with the user interface, view stored information, and so forth. Examples of users who can be permitted to access a user interface include patients, potential patients, significant others, friends, and family members of patients or potential patients, surgical technicians, imaging technicians (e.g., x-ray technicians, MRI technicians, etc.), surgeons, nurses, hospital administrators, surgical equipment manufacturer employees, insurance providers, and operating room directors.

The devices, systems, and methods disclosed herein can be implemented using one or more computer systems, which as mentioned above are also referred to herein as interfaces and client stations.

Figure 3:
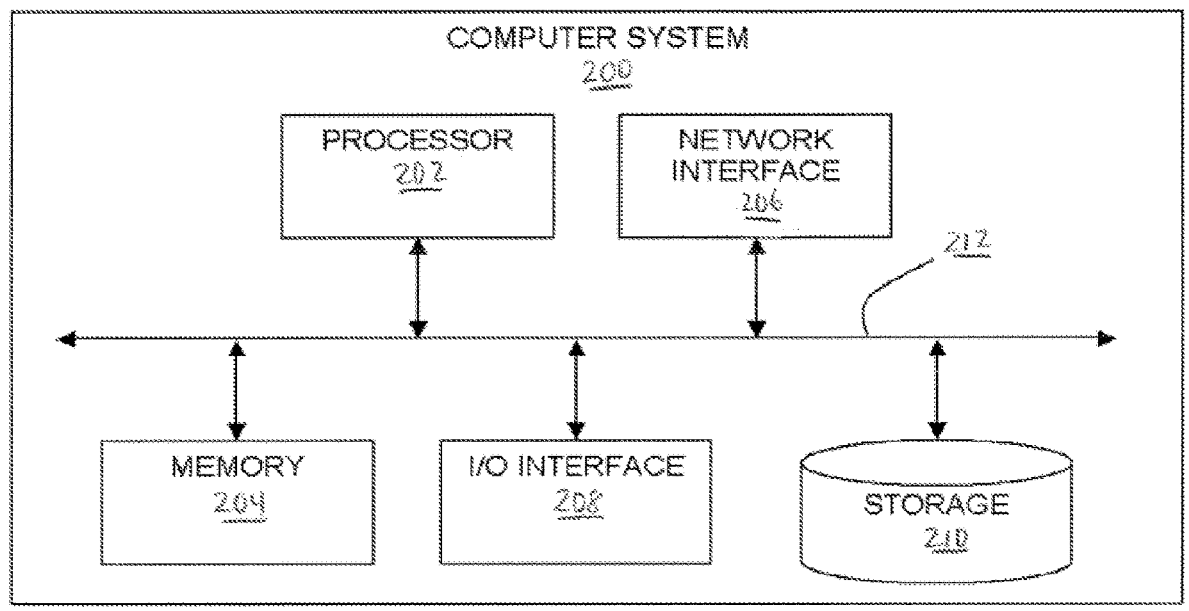
FIG. 3 is a schematic view of one embodiment of a computer system.

FIG. 3 illustrates one exemplary embodiment of a computer system 200. As shown in the illustrated embodiment, the computer system 200 can include one or more processors 202 which can control the operation of the computer system 200. The processor(s) 202 can include any type of microprocessor or central processing unit (CPU), including programmable general-purpose or special-purpose microprocessors and/or any one of a variety of proprietary or commercially available single or multi-processor systems. The computer system 200 can also include one or more memories 204, which can provide temporary storage for code to be executed by the processor(s) 202 or for data acquired from one or more users, storage devices, and/or databases. The memory 204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 200 can be coupled to a bus system 212. The illustrated bus system 212 is an abstraction that represents any one or more separate physical busses, communication lines/interfaces, and/or multi-drop or point-to-point connections, connected by appropriate bridges, adapters, and/or controllers. The computer system 200 can also include one or more network interface(s) 206, one or more input/output (I/O) interface(s) 208, and one or more storage device(s) 210.

The network interface(s) 206 can enable the computer system 200 to communicate with remote devices, e.g., other computer systems, over a network, and can be, for example, remote desktop connection interfaces, Ethernet adapters, and/or other local area network (LAN) adapters. The I/O interface(s) 208 can include one or more interface components to connect the computer system 200 with other electronic equipment. For example, the I/O interface(s) 208 can include high speed data ports, such as universal serial bus (USB) ports, 1394 ports, Wi-Fi, Bluetooth, etc. Additionally, the computer system 200 can be accessible to a user, and thus the I/O interface(s) 208 can include display screens, speakers, keyboards, pointing devices, and/or various other video, audio, or alphanumeric interfaces. The storage device(s) 210 can include any conventional unit or medium for storing data in a non-volatile and/or non-transient manner. The storage device(s) 210 can thus hold data and/or instructions in a persistent state, i.e., the value is retained despite interruption of power to the computer system 100. The storage device(s) 210 can include one or more hard disk drives, flash drives, USB drives, optical drives, various media cards, diskettes, compact discs, and/or any combination thereof and can be directly connected to the computer system 200 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 3 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 200 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing Hypertext Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 200 can also include a web server for generating and/or delivering the web pages to client computer systems.

In an exemplary embodiment, the computer system 200 can be provided as a single unit, e.g., as a single server, as a single tower, contained within a single housing, etc. The systems and methods disclosed herein can thus be provided as a singular unit configured to provide the various modules, display the various user interfaces, and capture the data described herein. The singular unit can be modular such that various aspects thereof can be swapped in and out as needed for, e.g., upgrade, replacement, maintenance, etc., without interrupting functionality of any other aspects of the system. The singular unit can thus also be scalable with the ability to be added to as additional modules and/or additional functionality of existing modules are desired and/or improved upon.

While some embodiments are described herein in the context of web pages, it will be appreciated that in other embodiments, one or more of the described functions can be performed without the use of web pages and/or by other than web browser software. A computer system can also include any of a variety of other software and/or hardware components, including for example, operating systems and database management systems. Although an exemplary computer system is depicted and described herein, it will be appreciated that this is for sake of generality and convenience. In other embodiments, the computer system may differ in architecture and operation from that shown and described here.

Referring again to the system 10 of FIG. 1, the accessory 12 can have a variety of sizes, shapes, and configurations. In general, the accessory 12 can be mechanical, e.g., a physical component including machinery and/or electrical elements. The accessory 12 can be configured to be removably and replaceably attached to the medication dispenser so as to allow the accessory 12 to be attached to the patient's existing medication dispenser and/or to be removed from an empty medication dispenser and attached to another medication dispenser. Examples of the accessory include a cap configured to attach to an end of a medication dispenser, a band or strap configured to wrap at least partially around a medication dispenser, and a box configured to attach to a surface of a medication dispenser. As mentioned above, the accessory 12 can instead be integrally attached to a medication dispenser, such as by being integrally formed therewith during manufacturing of the dispenser before a patient receives the dispenser.

The accessory 12 can include an activation member 26, a sensor 28, an actuator 30, a network interface 32, a processor 34, and a power source 36. Each of the activation member 26, the sensor 28, the actuator 30, the network interface 32, the processor 34, and the power source 36 can have a variety of sizes, shapes, and configurations.

The activation member 26 can be configured to be activated by a user when medication is dispensed from the dispenser. The activation member 26 can be configured to be automatically activated when the medication is dispensed. In other words, the medication being dispensed in its ordinary way can activate the activation member 26 such that a user of the dispenser need not perform any special action to activate the activation member 26. The activation member 26 can thus be integrated into the functionality of the dispenser, which can help the accessory 12 gather data regarding the medication, as discussed further below. For example, the activation member 26 can be positioned at an end of a respiratory inhaler that, even without the accessory 12 attached thereto, is configured to be pushed down by a user to release a metered-dose of respiratory medication from the inhaler. The activation member 26 can thus be configured to move when the medication is dispensed, thereby activating the activation member 26.

The activation member 26 can include a depressible member, as in the illustrated embodiment. The depressible member 26 includes a button, e.g., a push button, in the illustrated embodiment, but the depressible member 26 can be in another form, such as a depressible switch. Pushing the accessory 12, e.g., pushing on an inhaler to release medication therefrom, can automatically activate the activation member 26 as well as cause the medication to be released.

An example of the activation member 26 not as a depressible member includes a motion-sensitive member such as a motion sensor configured to sense movement of the accessory 12. For example, the motion-sensitive member can be positioned at an end of a respiratory inhaler (e.g., an asthma inhaler) that, even without the accessory 12 attached thereto, is configured to be pushed down by a user to release a metered-dose of respiratory medication from the inhaler, such that the motion-sensitive member can sense movement when the accessory 12 is pushed down. For another example, a first motion-sensitive member can be positioned on an exterior plastic container of a respiratory inhaler (e.g., an asthma inhaler), and a second motion-sensitive member can be positioned on a medication canister that is at least partially encased by the exterior plastic container. A difference in motion detected by the two motion-sensitive members can indicate that medication was dispensed.

Referring again to FIG. 1, when the activation member 26 is depressed by a user, thereby indicating that the medication is being dispensed, the activation member 26 can be configured to activate or "wake up" the processor 34. The activation member 26 can thus be configured to trigger data gathering by the processor 34, as discussed further below. The activation member 26 can be configured to or "wake up" the processor 34 in a variety of ways, as will be appreciated by a person skilled in the art, such as by causing a circuit to close when the activation member 26 is in a depressed position. The circuit can correspondingly be open when the activation member 26 is in a non-depressed position. The closing of the circuit can cause an activation signal to be transmitted to the processor 34 and/or for a circuit within the processor 34 to be closed. The activation signal can cause the processor 34 to perform one or more functions related to dispensing of the medication.

The pushing of the activation member 26 can be enough to cause the processor 34 to perform the function(s) related to dispensing of the medication. However, in some embodiments, the processor 34 can be configured to perform the function(s) related to dispensing of the medication in response to receipt of the activation signal only upon a secondary determination that medication was dispensed. In other words, the processor 34 can be configured to check for false positives. The sensor 28 can be configured to facilitate the secondary determination. The sensor 28 can help eliminate false positives when, for example, the dispenser is within a backpack or other bag and is jarred against a side of the bag so as to unintentionally, partially depress the activation member 26 and activate or "wake-up" the processor 34 even though medication was not actually dispensed.

The sensor 28 can have a variety of sizes, shapes, and configurations. The sensor 28 can be configured to sense at least one condition indicative of the medication being dispensed from the dispenser. The sensor 28 can be configured to transmit data regarding its sensed parameter(s) to the processor 34, which can be configured to analyze the received sensed data to help determine whether medication was dispensed from the dispenser. In general, the processor 34 can be configured to determine if the sensed parameter is above or below a predetermined threshold amount for the sensed parameter and conclude based on that determination whether the sensed parameter indicates that medication was dispensed.

The accessory 12 can include any number of sensors 28, e.g., zero, one, two, three, etc. If the accessory 12 includes a plurality of sensors 28, in an exemplary embodiment, each of the sensors 28 can be configured to sense a different parameter so as to provide a plurality of factors to aid in the processor's secondary determination of the medication being dispensed or not.

The sensor 28 can be configured to continuously sense data, or the sensor 28 can be configured to sporadically sense data based on activation of the activation member 26. The sensor 28 continuously sensing data can help ensure that the sensor 28 has adequate data available each time the processor 34 is activated by the activation member 26. Continually sensing data can help the processor 34 "learn" ambient conditions of the dispenser, the accessory 12, and/or the medication over time, which can help the processor 34 better distinguish false positives from actual instances of the medication being dispensed. The sensor 28 can be configured to sporadically sense data by being triggered by the processor 34 to begin sensing. The processor 34 can be configured to provide such a trigger when the processor 34 is activated by the activation member 26. Sporadically sensing data can consume less power than continuously sensing data, which can help prolong a life of the accessory 12.

Examples of the sensor 28 include a motion sensor, a pH sensor, a temperature sensor, an audio sensor, and a geographic location sensor. The motion sensor, e.g., an accelerometer, gyroscope, or a magnetic field sensor, can be configured to sense motion, e.g., movement, shock, vibration, orientation, etc., of the accessory 12. If the sensed motion is above a predetermined threshold amount of motion, the processor 34 can be configured to determine that medication was dispensed because the accessory 12 moved enough to cause the medication to be dispensed. The predetermined threshold amount of motion can vary based on the dispenser, as different dispensers can require a different amount of user-caused motion to dispense medication from the dispenser. If the motion sensor is configured to sense orientation, the processor 34 can be configured to determine whether the sensed orientation matches a predetermined orientation indicative of a medication-dispensing position of the dispenser. For example, respiratory inhalers are typically held in a same, upright position when medication is dispensed in order for the dispenser to be comfortably held by hand with the dispenser's output positioned adjacent the patient's mouth.

The pH sensor can be configured to sense a pH at a location where the medication is dispensed from the dispenser. For some types of medication, such as respiratory medications dispensed from an inhaler, the pH changes at an output of the dispenser because the medication has a different pH than ambient air ordinarily at the output. If the sensed pH is outside a predetermined temperature range, is above a predetermined threshold pH, and/or changes by more than a predetermined threshold amount, the processor 34 can be configured to determine that medication was dispensed because the pH changed enough to indicate that the medication was dispensed. The predetermined threshold pH and predetermined threshold amount can vary based on the medication, as different medications can have different pHs.

The temperature sensor can be configured to sense a change in temperature, such as a change in temperature of the dispenser. Some types of medication can cause the dispenser to temporarily change in temperature when the medication is dispensed from the dispenser. If the sensed temperature is outside a predetermined temperature range, is below a predetermined threshold temperature, and/or changes by more than a predetermined threshold amount, the processor 34 can be configured to determine that medication was dispensed because the temperature changed enough to indicate that the medication was dispensed. For example, at least some respiratory medications dispensed from an inhaler can cause the inhaler canister to temporarily decrease in temperature. The temperature sensor can thus facilitate determination that medication was dispensed from the canister. For another example, some medications can change temperature when damaged, e.g., decrease in temperature if left unrefrigerated beyond a certain amount of time. The temperature sensor can facilitate this determination of medication spoilage.

The audio sensor, e.g., a microphone, etc., can be configured to sense a sound of medication dispensing. Some types of medication can create a sound having a predictable profile when the medication is dispensed from the dispenser. If the sensed sound is within a certain decibel range and/or changes by more than a predetermined threshold amount, the processor 34 can be configured to determine that medication was dispensed because the sound matches a sound profile of the medication being dispensed. For example, at least some respiratory medications dispensed from an inhaler can cause a predictable misting sound at the dispenser's output that is not present unless the medication is being dispensed from the inhaler.

The geographic location sensor, e.g., a global positioning system (GPS) sensor, etc., can be configured to sense a geographic location of the patient. The accessory 12 can thus be configured to log a geographic location of the patient when medication is dispensed from the dispenser so as to help provide context for where a patient was when medication was taken. Such geographic data can help determine whether certain environments exacerbate a patient's condition, e.g., because more emergency doses of medication are taken when a patient is in a certain locale.

The actuator 30 can have a variety of sizes, shapes, and configurations. The actuator 30 can be configured to indicate to a user, e.g., to the patient 22, that a predetermined condition has occurred. The predetermined condition can reflect that action by the user is needed, such as the patient 22 taking a dose of the medication, the dispenser being replaced due to little medication remaining therein, or the dispenser being replaced due to no medication remaining therein. The predetermined condition can require no user action, such as a scheduled dose of the medication not being taken and data being transmitted from the accessory 12 to the wireless bridge 14. The processor 34 can be configured to actuate one or more of the actuators 30 in response to the processor 34 detecting occurrence of the predetermined condition, as discussed further below. Examples of the actuator 30 include a light (e.g., an LED, a fluorescent material, etc.) configured to illuminate, a speaker configured to output an audible sound, a vibration element configured to vibrate so as to cause palpable and/or audible vibration of the accessory 12 and/or the dispenser, a temperature-changing element configured to temporarily heat and/or cool so as to cause a palpable change in temperature of the accessory 12 and/or the dispenser, and a display screen configured to display text and/or images as a message to the user.

The accessory 12 can include any number of actuators 30, e.g., zero, one, two, three, etc. If the accessory 12 includes a plurality of actuators 30, in an exemplary embodiment, each of the actuators 30 can be configured to provide a different type of notification than at least one other of the actuators 30, e.g., a plurality of actuators 30 including at least one light and at least one speaker, so as to allow the accessory 12 to provide a plurality of different notifications when medication is due and/or to provide a different type of notification upon different types of predetermined conditions, a light of a first color and one vibration element for medication being due, a light of a second color for medication in the dispenser running low and a blinking light of the second color for medication in the dispenser being depleted, a blinking light when a medication dose is missed and a notification such as an email, text message, or phone call (which can be a live phone call or an automated phone call and can include leaving a voicemail or other recorded message) being sent to a location remote from the dispenser indicating that the medication dose was missed, etc.

The accessory 12 can be configured to cause a notification to be transmitted to a location remote from the dispenser instead of or in addition to a notification being provided via the actuator 30 at the dispenser. Providing a remote notification can facilitate supervision of the patient 22 and/or management of the patient's treatment plan. For example, if the patient 22 is a child, it can be beneficial to notify the user 24 associated with the patient upon occurrence of certain events to help make the user 24 aware of the patient's medication status so the user 24 can take any appropriate action in real time and/or at a later time. For example, if a dose of medication is due, the processor 34 can be configured to cause a first notification to be provided to the patient 22 via the actuator 30 at the dispenser and to cause a second notification to be provided to the user 24, who may be at a location remote from the patient 22. The user 24 can then decide whether to independently contact the patient 22 as a secondary reminder to take medication. For another example, if the processor 34 determines that medication was dispensed off the patient's predetermined medication schedule, the processor 34 can be configured to cause a notification such as an email, text message, or phone call to be provided to the user 24, who, given this atypical use of the medication, may be the patient's medical care provider or be able to contact the patient's medical care provider as the patient's parent or guardian. If multiple off-schedule medication doses are detected, the patient's medical care provider may choose to contact the patient 22 (or an adult contact for a child patient) to discuss possible changes to the patient's health and/or to the patient's treatment plan. For another example, if medication is not dispensed within a predetermined period of time after a notification is provided indicating that a scheduled dose of medication is due, the processor 34 can be configured to cause a missed dosage notation to be saved in the accessory's memory, and the wireless bridge 14 can be configured to wirelessly transmit the stored missed dosage notation to an external device such as the database 18. The missed dosage notation can be included as part of adherence data and/or incentives data provided on a user interface, discussed further below. An external device, e.g., the interface 20, can be configured to determine that a medication dose was missed without the processor 34 providing any notice thereof, such as by the external device being configured to detect that notice of an expected dose was not taken, e.g., notice of medication being dispensed at a scheduled date/time was not received at the external device from the accessory 20. For yet another example, if the processor 34 determines that the medication is running low, the processor 34 can be configured to cause a notification such as an email, text message, or phone call to be provided to the user 24, such as the patient's doctor or pharmacist, who can begin processing a new supply of medication for the patient 22 before the patient's current medication is depleted.

Figure 4:
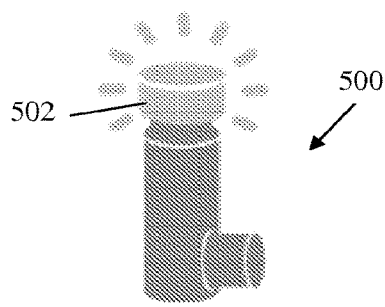
FIG. 4 is a perspective view of one embodiment of a medication dispenser having an accessory removably and replaceably attached thereto, the accessory being illuminated with a light of a first color to indicate a first condition.
Figure 5:
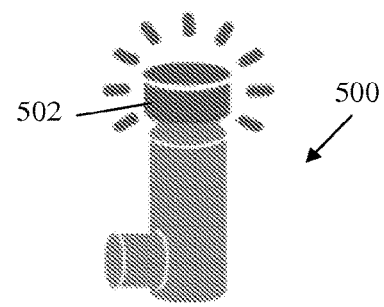
FIG. 5 is a perspective view of the medication dispenser and the accessory of FIG. 4, the accessory being illuminated with a light of a second color to indicate a second condition.

FIGS. 4 and 5 illustrate an embodiment of a medication dispenser 500 having an accessory 502 removably and replaceably attached thereto, the accessory 502 including two actuators (obscured in FIGS. 4 and 5) in the form of two differently colored lights. FIG. 4 shows the accessory 502 illuminated with one of the colored lights to indicate a first predetermined condition, and FIG. 5 shows the accessory 502 illuminated with the other of the colored lights to indicate a second, different predetermined condition. The actuators can remain illuminated for a predetermined amount of time, or one or both of the lights can remain illuminated until occurrence of an end event such as medication being dispensed from the dispenser or data transmission to the wireless bridge 14 ending. Although the lights in FIGS. 4 and 5 are configured to steadily illuminate, a light can be configured to flash instead of steadily illuminate.

The processor 34 can be configured to control one or more components of the accessory 12. The processor 34 can have a variety of sizes, shapes, and configurations, as discussed above. The processor 34 in the illustrated embodiment is shown as a microcontroller, but the processor 34 can include any of a variety of elements, as mentioned above. The processor 34 can, as will be appreciated by a person skilled in the art, include a timer configured to count time and/or a memory configured to store data. Alternatively, the timer and/or the memory can be included as part of the accessory 12 but be external components to the processor 34.

The processor 34 can be configured to cause gathered data to be stored in the memory and to cause stored data to be transmitted to an external device, e.g., wirelessly transmitted via the wireless bridge 14 across the network 16 to the interface 20 and/or the memory 18. The memory 18 in the illustrated embodiment includes a database, but as discussed above, the memory 18 can include any one or more memory technologies. The interface 20 in the illustrated embodiment includes a client station in the form of a distributed computer system (e.g., a phone, a computer, etc.), but the interface 20 can include any form of client station.

The processor 34 can be configured to transmit stored data to the interface 20 and/or the memory 18 on a predetermined transmission schedule, e.g., a schedule stored in the memory and time-tracked using the timer, in response to occurrence of a predetermined condition, and/or in response to a data request signal to the processor 34 from an external device. The processor 34 can be configured to delete transmitted data from the memory in response to the data having been transmitted, which can help free space for new data, the processor 34 can be configured to delete transmitted data on a regular deletion schedule (e.g., at the top of each hour, at the end of a day, at the end of a week, twice daily, etc.), or the processor 34 can be configured to delete transmitted data as needed for storage space. The processor 34 can be configured to maintain all data until the data is transmitted to an external device, which can help prevent data loss. The processor 34 can be configured to mark data stored in the memory as having been transmitted to an external device, which can facilitate clearing of the accessory's memory and/or help ensure that data is not unnecessarily repeatedly transmitted to an external device.

Various types of data can be received and stored by the processor 34. For example, data sensed by the sensor 28 can be received and stored. For another example, data regarding occurrences of predetermined conditions can be stored. Examples of predetermined conditions include medication being dispensed (e.g., as triggered by activation of the activation mechanism 26 and/or as confirmed by data from the sensor 28), low power source 36 power, power source 36 depletion, medication not being dispensed in accordance with a predetermined medication schedule, and device component failure. The processor 34 can therefore be configured to receive, store, and transmit a relatively complete picture of the patient's medication usage and of a functional status of the dispenser and a functional status of the accessory 12. Data transmitted by the processor 34 can be analyzed by and/or viewed on the interface 20, as discussed further below.

The processor 34 can be configured to maintain a running tally of a total amount of medication dispensed from the dispenser. In this way, the processor 34 can be configured to determine when the dispenser is running low on medication and/or when all medication has been dispensed from the dispenser. For example, some types of dispensers, such as respiratory inhalers, can be configured to dispense a predetermined amount of medication each time the medication is dispensed therefrom. The processor 34 can be configured to maintain the running tally of a total amount of medication dispensed from the dispenser by adding a predetermined value to the previously logged total amount each time medication is determined to have been dispensed from the dispenser. For another example, the accessory 12 can be configured to detect an amount of medication dispensed, e.g., by using the sensor 28, and to subtract the measured amount from a previously stored total amount of medication in the dispenser to arrive at a current total amount of medication in the dispenser.

The processor 34 can be configured to provide a warning to a user when the processor determines that the dispenser is running low on medication and/or when all medication has been dispensed from the dispenser. Providing warnings about low/no medication remaining can help the user effectively manage reordering and replacement of medication. The processor 34 can be configured to provide the warning by actuating the actuator 30.

The processor 34 can be configured to actuate the actuator 30 by transmitting a signal thereto. In response to the triggering signal from the processor 34, the actuator 30 can be configured to provide an audible and/or palpable signal to a user, e.g., to the patient 22, indicating one or more predetermined conditions. One example of the predetermined condition is the low medication warning mentioned above, and another example of the predetermined condition is the medication depleted warning also mentioned above.

Another example of the predetermined condition is a notification when a dosage of the medication is due. In other words, the accessory 12 can be configured to provide notice to a user, e.g., to the patient 22, that medication needs to be taken in order to adhere to a predetermined medication schedule. The accessory 12 providing the notification can allow the medication dispenser itself to play a role in a patient's medication regimen, which can help reduce the need for the patient, the patient's family, the patient's doctor, etc. to maintain and monitor an external notification system, such as watch alarms, alarms on a mobile device, phone calls to the patient, text messages to the patient's mobile phone, etc.

The processor 34 can be configured to determine that a dosage of medication is due in a variety of ways. A predetermined medication schedule for the patient 22 can be accessible to the processor 34, e.g., stored in a memory included in the accessory 12 or stored in an external memory accessible via the network 16, such as the memory 18. The predetermined medication schedule can, as will be appreciated by a person skilled in the art, be specific to the patient 22 as determined by the patient's doctor or other care provider, or the predetermined medication schedule can be dictated by a manufacturer of the medication. The accessory 12 can be configured to register itself, e.g., with the memory 18, when purchased and/or when attached to a medication dispenser so as allow the predetermined medication schedule to be transmitted to the accessory 12, e.g., from the memory 18. The processor 34 can be configured to determine when medication is due according to the predetermined medication schedule based on time counted by the timer. The accessory 12 can thus be configured as a self-contained monitoring unit able to notify the user that medication is due to be taken regardless of the accessory's location relative to the interface 20 and/or other external device. Alternatively, or in addition, an external device such as the interface 20 can be configured to determine when a dosage of the medication is due for the patient 22 in a similar way and transmit a signal to the accessory 12 via the network 16. The signal can cause the actuator 30 to be actuated. Allowing the external device to trigger the actuator 30 can provide backup functionality to the processor 34 and/or can help move processing resources off-board from the accessory 12, which can help reduce cost and/or help reduce a size of the accessory 12.

Another example of a predetermined condition is data being transmitted from the accessory 12 via the network interface 32. Providing notice to the user that data is being transmitted can help explain why the accessory 12 may be buzzing or otherwise making a noise not typically associated with the medication dispenser. Similarly, another predetermined condition is data being transmitted to the accessory 12 via the network interface 32, such as an update to the patient's predetermined medication schedule stored onboard the accessory 12.

As mentioned above, a predetermined condition can include the power source 36 running low, thereby indicating that the accessory 12 is due for removal from the dispenser and replacement with another accessory. Similarly, another predetermined condition is the power source 36 being depleted of available power.

As mentioned above, a predetermined condition can include failure of any component of the accessory 12, such as a failure of the sensor 28 or the actuator 30, thereby indicating that the accessory 12 should be removed from the dispenser and replaced with another accessory. The processor 34 can be configured to detect failure of a component of the accessory 12, such as by being programmed to regularly query component(s), as will be appreciated by a person skilled in the art, and, based on a response received from the queried component, including whether a response was received or not, determine whether the component is properly functioning.

The network interface 32 can be configured to facilitate electronic communication of the accessory 12 with one or more external devices such as the wireless bridge 14. The network interface 32 can have a variety of sizes, shapes, and configurations, as discussed above. Although the network interface 32 is illustrated as a radio and as being in electronic communication with the wireless bridge 14 in the illustrated embodiment, the network interface 32 can be a component other than a radio and can be configured to be in electronic communication with a wireless bridge and/or any number of other components to facilitate communication over the network 16. The network interface 32 can be configured to communicate using long-range, low frequency/low power/low bandwidth radio communication using a proprietary, an open source, or a mesh protocol.

The power source 36, e.g., one or more batteries, one or more solar panels, one or more piezo elements, one or more inductively charged power elements, etc., can have a variety of sizes, shapes, and configurations. The power source 36 can be configured to provide power to one or more of the accessory's components, e.g., to the sensor 28, the processor 34, the wireless bridge 14, the actuator 30, etc. In some embodiments, an accessory can lack a power source and instead be powered by an external power source, such as a power source wired to the accessory via wired connection or a power source configured to telemetrically provide power when moved into proximity of the accessory. In some embodiments, an accessory can include an on-board power source, as in the illustrated embodiment of FIG. 1, configured to provide power to only a portion of the accessory's on-board components, and the accessory can be configured to have another portion of the accessory's on-board components be powered by an external power source. Providing power with an external power source can help reduce a size of the accessory and/or free space for other components.

The power source 36 can be configured to move between a first state in which the power source 36 provides a first amount of power to components of the accessory 12 and a second state in which the power source provides a second, greater amount of power to the components of the accessory 12. The power source 36 can thus be configured to conserve power by being in the first state when the greater amount of power provided in the second state is not necessary for proper functioning of the accessory 12.

In an exemplary embodiment, the power source 36 in the first state can be configured to provide a non-zero amount of power to the processor 34 and in the second state can provide a greater amount of power to the processor 34. The non-zero amount of power can be an amount of power adequate to power the processor's timer, thereby allowing the timer to maintain accurate time so as to, e.g., allow notifications to be properly triggered for due medication doses, allow for a correct date/time to be logged upon detection of medication being dispensed from the dispenser, etc. If the timer is a separate component from the processor 34, the power source 34 in the first state can be configured to provide the non-zero amount of power to the timer instead of to the processor 34.

The non-zero amount of power can be less than a required amount of power to allow data to be stored in the accessory's memory, while the amount of power provided when the power source 36 in the second state can be enough to allow the processor 34 to store data in the memory. The power source 36 can thus conserve power by not providing power to the processor 34 for memory storage unless the processor 34 receives data to store in the memory. The power source 36 can be configured to move from the first state to the second state in response to the sensor 28 sensing the medication being dispensed, thereby allowing the processor 34 to have adequate power to receive and store the sensed data in the memory. The power source 36 can be configured to move from the second state to the first state in response to storage of the data in the memory, thereby allowing the power source 36 to return to the lower power supply state when the processor 34 no longer needs the higher amount of power to store data.

In the first state, the power source 36 can be configured to provide no power to components of the accessory 12 other than the processor 34 (or the timer), which can help conserve power. In the second state, the power source 36 can be configured to provide power to one or more components of the accessory 12 in addition to the processor 34 (or the timer), which can allow the processor's commands to be carried out, e.g., for the actuator 30 to be actuated, for the wireless bridge 14 to transmit data, etc. The power source 36 can thus be configured to continuously provide power to the processor 34 (or the timer) and only intermittently provide power to the accessory's other components. For example, the power source 36 can be configured to only provide power to the actuator 30 when the power source 36 is in the second state so as to allow the actuator 30 to provide a notification in response to a determination that a scheduled medication dose is due. For another example, the power source 36 in the first state can be configured to not provide adequate power to the wireless bridge 14 to allow the wireless bridge 14 to wirelessly transmit data, and the power source 36 in the second state can be configured to provide adequate power to the wireless bridge 14 to allow the wireless bridge 14 to wirelessly transmit data. The wireless bridge 14 can thus only receive power when data is available for transmission to an external device such as the database 18 or the interface 20. The power source 36 in the second state can be configured to provide all power for the wireless transmission by the wireless bridge 14. The power source 36 can be configured to move from the first state to a third state in response to a request for data from an external device such as the database 18 or the interface 20. The power source 36 in the third state can be configured to provide adequate power to the wireless bridge 14 to allow the wireless bridge 14 to wirelessly transmit data to the external device in response to the request for data, and the power source 36 can be configured to move from the third state to the first state in response to the wireless bridge 14 wirelessly transmitting data to the external device in response to the request for data. The wireless bridge 14 can thus only receive power when needed in order to fulfill an external request for data.

If the sensor 28 requires power to sense data and does not include its own onboard power, the power source 36 in the first state can be configured to provide a non-zero amount of power to the sensor 28 so as to allow the sensor 28 to continuously sense data to facilitate determination of medication being dispensed from the dispenser. In the second state, the power source 36 can continue to provide the non-zero amount of power to the sensor 28.

The accessory 12 can include a housing 42 configured to house the activation member 26, the sensor 28, the actuator 30, the network interface 32, the processor 34, the power source 36, and the wireless bridge 14. The accessory 12 as a singular unit including the housing 42 and all components housed therein can be configured to be removably and replaceably attached to the medication dispenser, thereby allowing simple attachment of a single piece to the medication dispenser to attach the accessory 12 thereto. The accessory 12 can thus lack any required user assembly and be easily attached to a medication dispenser by adults and by at least older children.

The housing 42 can have a variety of sizes, shapes, and configurations and can be formed from one or more materials. In an exemplary embodiment, the housing 42 can be formed from one or more polymers and can be non-toxic. The housing 42 can be rigid or, as in the illustrated embodiment, have some degree of flexibility, which can facilitate depression of the activation member 26, as discussed further below. The housing 42 can be transparent or translucent so as to allow a light to visibly shine therethrough, as also discussed further below. The housing 42 can be waterproof so as to help protect the various components housed therein from moisture damage. The housing 42 can be permanently closed or sealed (e.g., closed or sealed under conditions of ordinary end-user use) so as to help prevent tampering with and/or inadvertent damage to the various components housed therein. The housing 42, and hence the accessory 12, can be configured to be disposable, e.g., thrown out or recycled. An accessory can, in some embodiments, be non-removably attached to a medication dispenser, in which case the accessory can be configured to be disposed of with the medication dispenser.

The housing 42 is shown in the illustrated embodiment as housing all of the activation member 26, the sensor 28, the actuator 30, the network interface 32, the processor 34, the power source 36, and the wireless bridge 14, but one or more of these components can be disposed in at least one other housing configured to attach to the medication dispenser similar to that discussed herein regarding the housing 42. For example, the wireless bridge 14 can be housed in a second housing (not shown) of the accessory 12, which can help facilitate hardware and/or software repair and/or upgrades related to electronic communication that otherwise do not substantially affect operation of the accessory 12. The second housing can be made, configured, and used similar to that discussed herein regarding the housing 42.

The accessory 12 can be configured to be attached to the dispenser in a variety of ways. The accessory 12 can include an attachment mechanism configured to engage the dispenser and removably and replaceably attach the accessory 12 thereto. Examples of the attachment mechanism include a magnet configured to magnetically attach the accessory 12 to a magnet included in or a metallic material of the dispenser, Velcro®, a cavity formed in the accessory configured to fit around a portion of the dispenser in a press fit, a strap or band configured to be tied to secure the accessory 12 to the dispenser, a strap or band configured to elastically secure the accessory 12 to the dispenser similar to a rubber band, a clip configured to clip the accessory 12 to the dispenser, and a guide track configured to slidably receive a portion of the dispenser therein. The attachment mechanism as a magnet can be particularly effective for use with pressurized medication dispensers, such as respiratory inhalers, which are typically metallic containers. The attachment mechanism being attachable to the dispenser by press fit can help prevent mis-attachment of the accessory 12 to the dispenser because the cavity can be configured to be attachable to the dispenser in one location via the press fit, e.g., the cavity being configured to only accommodate one unique portion of the dispenser. The accessory 12 can be included as part of a kit including a plurality of differently sized and/or differently shaped members (e.g., flexible rings, rigid rings, etc.) configured to be selectively attached to the accessory 12 to facilitate press fit of the accessory 12 to a particular medication dispenser. For example, a one of the members having a size and shape corresponding to a circular size of an end of a respiratory inhaler can be inserted into a cavity of an accessory in the form of a cap so as to be seated in a groove formed therein. The member can be configured to form a press fit with the inhaler when the cap is attached thereto. The attachment mechanism being an adjustable member, such as a strap or band, can facilitate attachment of the accessory 12 to differently sized and/or irregularly shaped dispensers.

The attachment mechanism can allow the accessory 12 to be replaceably and removably attached to the dispenser without requiring any modification of the dispenser by the end-user or by a designer or manufacturer of the dispenser to accommodate the accessory 12. In this way, the accessory 12 can be used with nearly any medication dispenser regardless of whether or not the dispenser was made for use with the accessory 12. Examples of attachment mechanisms that can allow for such attachment include a magnet, a cavity, and a strap or band. Other attachment mechanisms, such as a magnet or Velcro®, may require a modification of the dispenser to allow attachment of the accessory 12 thereto, such as by attaching a magnet or Velcro® to the dispenser using a self-stick adhesive.

Figure 6:
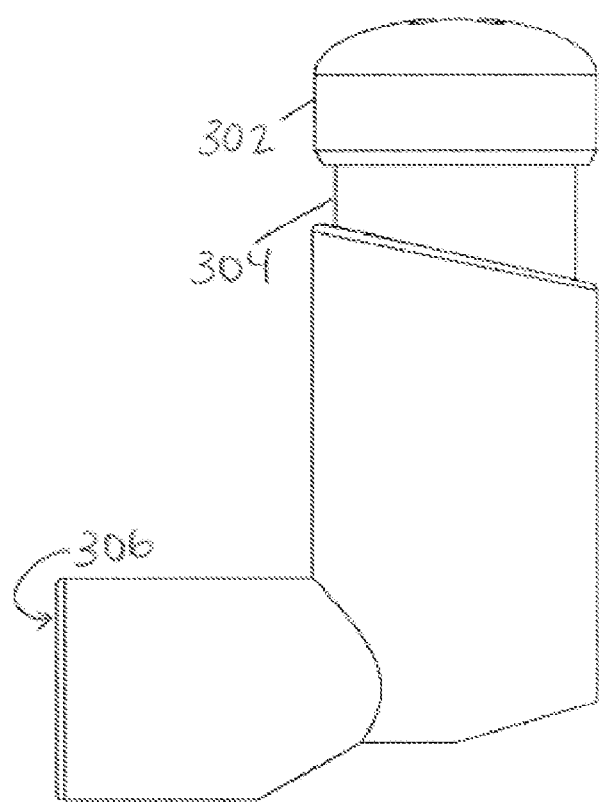
FIG. 6 is a side view of one embodiment of a medication dispenser having an accessory removably and replaceably attached thereto.
Figure 7:
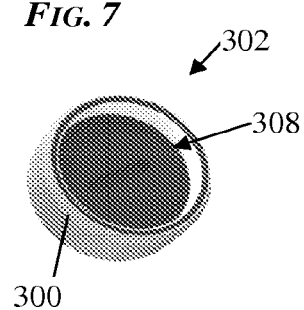
FIG. 7 is a perspective view of the accessory of FIG. 6.
Figure 8:
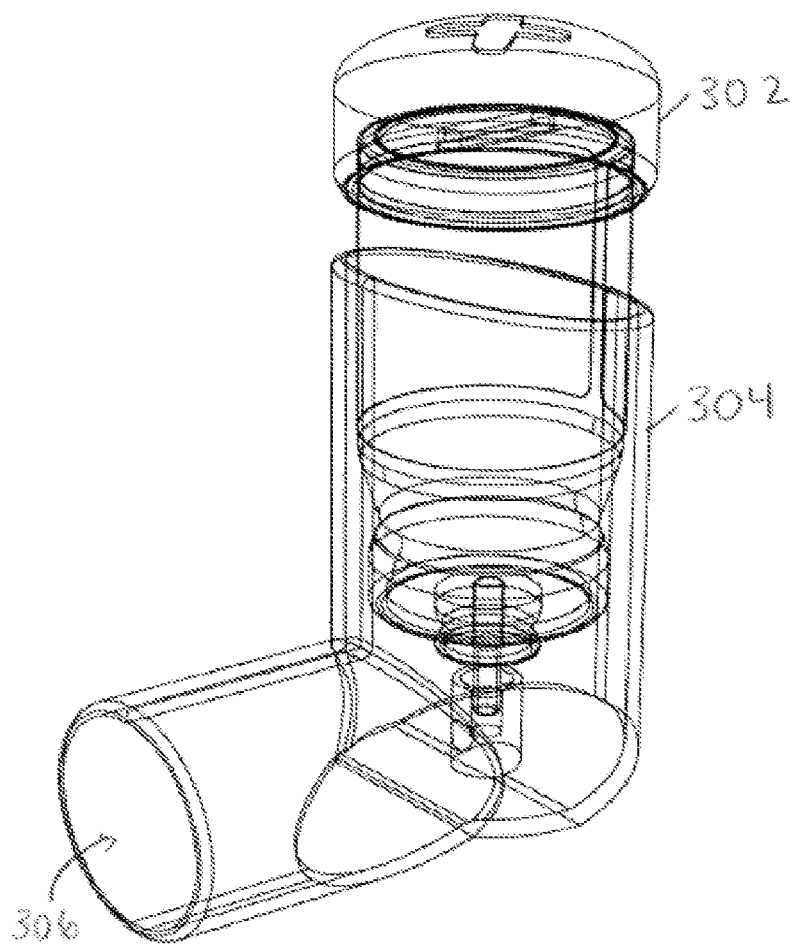
FIG. 8 is a transparent schematic view of the medication dispenser and the accessory of FIG. 6.

FIGS. 6-8 show one embodiment of a housing 300 of an accessory 302. The accessory 302 is shown in FIGS. 6 and 8 removably and replaceably attached to a medication dispenser 304 and is shown in FIG. 7 as a standalone element unattached to any medication dispenser. The medication dispenser 304 of FIGS. 6 and 8 is a respiratory inhaler containing a medication for treating a respiratory condition such as asthma, but as mentioned above, an accessory can be configured to attach to a variety of different types of medication dispensers containing different types of medications.

The housing 300 can be a cap, as in the illustrated embodiment of FIGS. 6-8, as well as the illustrated embodiment of FIGS. 4 and 5. The cap can be configured to removably and replaceably attach to a portion of the dispenser 304, such as to an end of the respiratory inhaler 304 configured to be pressed by a user to dispense medication from the dispenser. The accessory 302 can thus be configured to be depressed to cause medication to be dispensed from an output 306 of the dispenser 304 similar to how medication would be dispensed from the dispenser 304 without having the housing 300 attached thereto. The accessory 302 can thus be relatively seamlessly integrated into a patient's familiar use of the dispenser 304.

In the illustrated embodiment, the attachment mechanism of the accessory 302 includes a cavity 308 formed in the housing 300. The cavity 308 can be configured to receive a portion of the dispenser 304 therein, e.g., an end portion of the dispenser 304. In the illustrated embodiment, the cavity 308 is configured to only be attachable to that one portion of the dispenser 304, which as mentioned above, can help ensure that the accessory 302 is properly attached to and used with the dispenser 304 because there is only one option to the user in choosing where to attach the accessory 302 to the dispenser 304.

The housing 300 can include a symbol 310 thereon, e.g., printed thereon, formed therein as a depression (as in the illustrated embodiment), formed thereon as a protrusion, embedded therein, etc. The symbol 310 can include any one or more of numbers, alphabet characters, and geometric shapes, logos, and other symbols. Although only one symbol 310 is shown in the illustrated embodiment, a housing can include any number of symbols thereon. The symbol 310 can identify a manufacturer of the accessory 12, can identify a specific medication or type of medications for use with the accessory 12, and/or can be decorative (e.g., a patient's name, a patient's first initial, a cartoon character, etc.). In the illustrated embodiment, the symbol 310 includes a plus sign.

Figure 9:
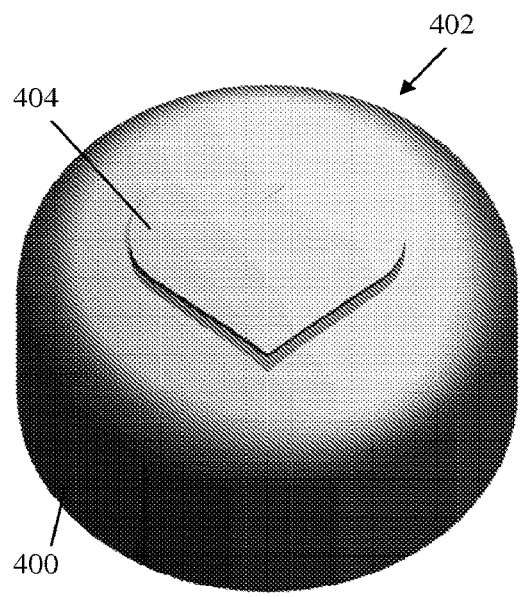
FIG. 9 is a perspective view of an embodiment of an accessory configured to be removably and replaceably attached to a medication dispenser.
Figure 10:
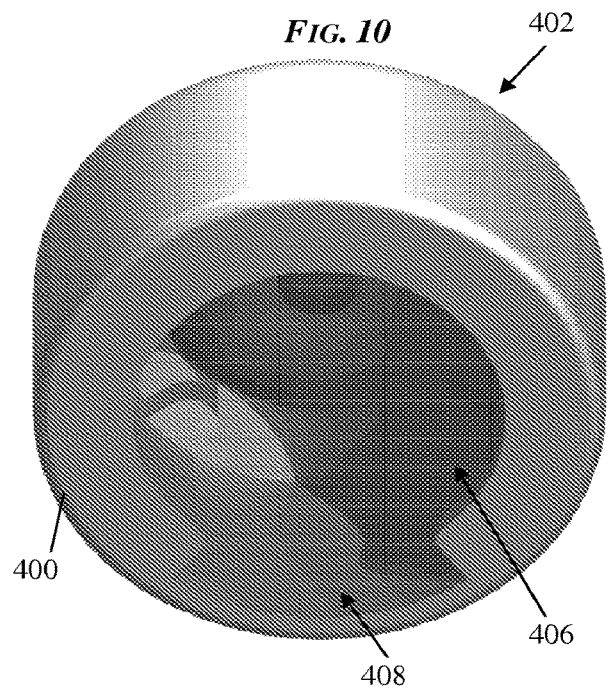
FIG. 10 is another perspective view of the accessory of FIG. 9.

FIGS. 9 and 10 illustrate another embodiment of an accessory 402 in the form of a cap that includes a housing 400 having a symbol 404 formed thereon, the symbol 404 being in the form of a heart-shaped protrusion. The housing 400 also includes a cavity 406 configured to seat a portion of a medication dispenser therein by press fit. As in this illustrated embodiment of the cavity 406, a cavity can be keyed to a medication dispenser, such as by including a keyhole 408 configured to engage a corresponding key of the dispenser so as to position the accessory 402 in a particular orientation relative to the dispenser when the accessory 402 is attached thereto. The keying can help ensure that the accessory 402 is properly attached to the dispenser. Although the accessory 402 in the illustrated embodiment includes the keyhole to engage a dispenser's key, an accessory can include a key configured to engage a keyhole of a dispenser.

Figure 11:
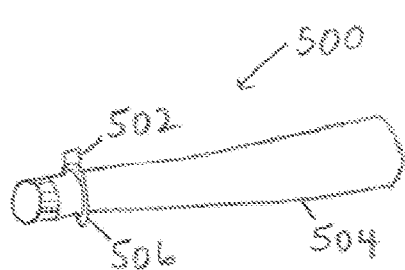
FIG. 11 is a perspective view of another embodiment of a medication dispenser having an accessory removably and replaceably attached thereto.

FIG. 11 illustrates an embodiment of an accessory 500 that includes a housing 502 configured to be attached to a medication dispenser 504 via an attachment mechanism 506 in the form of an elastic band or strap. The dispenser 504 in this illustrated embodiment includes a medicament tube configured to be squeezed to dispense medication therefrom.

Figure 12:
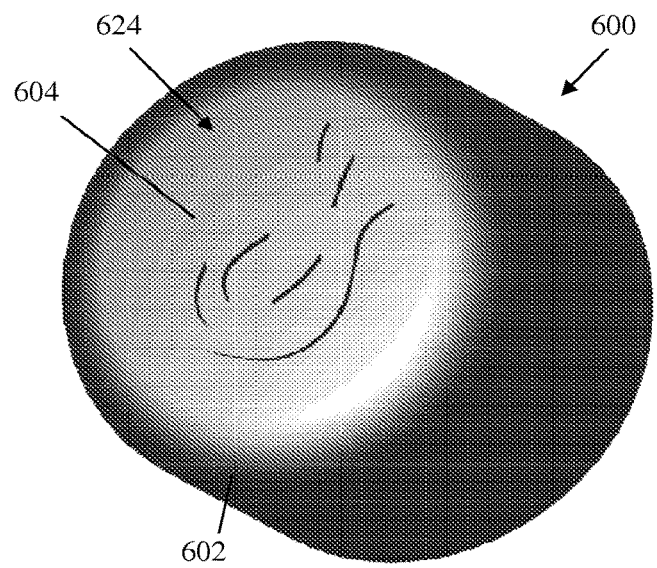
FIG. 12 is a perspective view of another embodiment of an accessory configured to be removably and replaceably attached to a medication dispenser.
Figure 13:
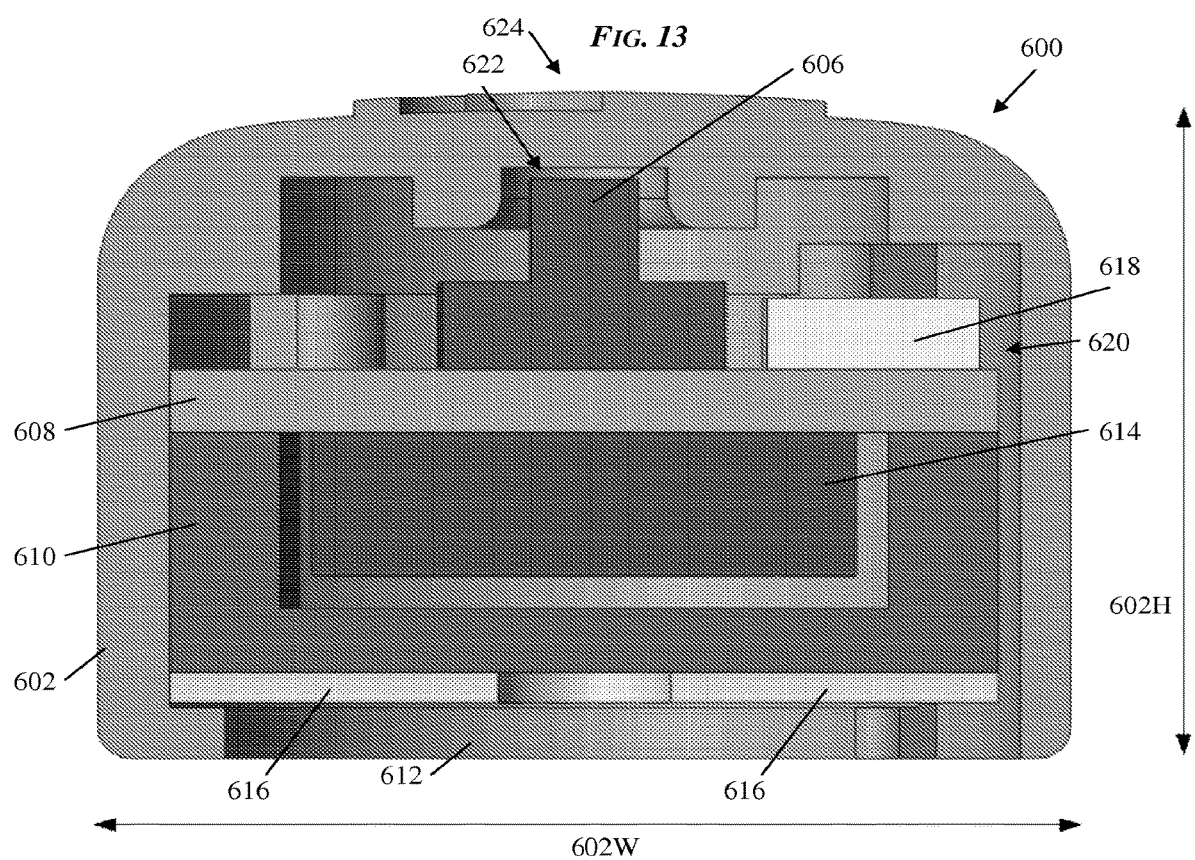
FIG. 13 is a side cross-sectional view of the accessory of FIG. 12.

FIGS. 12 and 13 illustrate another embodiment of an accessory 600 in the form of a cap that includes a housing 602 having a symbol 604 formed thereon, the symbol 604 being in the form of a flame-shaped protrusion. The housing 602 can have a variety of sizes. In the illustrated embodiment, the housing 602, and hence the accessory 600, has a height 602H of 0.66 in. and a width 602W of 0.88 in, which can facilitate attachment of the accessory 600 to an end of a standard sized respiratory inhaler.

As shown in FIG. 13, the accessory 600 can include an activation member 606 (in the form of a depressible button in this illustrated embodiment), a printed circuit board (PCB) 608, a support board 610 for the PCB 608, an attachment mechanism 612 (in the form of a magnet in this illustrated embodiment), a power source 614 (in the form of a coin cell battery in this illustrated embodiment), a washer 616 (a steel washer in this illustrated embodiment) configured to attract the magnet 612 and provide a buffer between the attachment mechanism 612 and the support board 610, a flexible flat cable (FFC) connector 618 configured to couple to a FFC (not shown), and a FFC slot 620 configured to seat the FFC. The PCB 608 can be the accessory's processor, or the PCB 608 can operate as the accessory's processor in cooperation with at least one off-board component, e.g., a CPU control store (CCS) module located outside the cap, as discussed further below. As will be appreciated by a person skilled in the art, a CCS module generally stores instructions or data structures, such as a microprogram or microcode, for a CPU or other processor. The PCB 608 can include a timer and/or a memory for the accessory 600.

The activation member 606 can be configured to move within the accessory 600 relative to the PCB 608 in response to a user, e.g., a patient, pushing or pressing on the housing 602, e.g., pushing or pressing on a proximal surface 624 of the housing 602. The user pushing or pressing the housing 602 can thus push or press the button 606, e.g., move the activation member 606 in a distal direction, so as to move the button from a non-depressed position to a depressed position. The activation member 606 moving relative to the PCB 608 can cause the activation member 606 to contact the PCB 608 so as to cause a circuit thereof to close. As discussed above, closing the circuit can cause the accessory's processor to be activated. The activation member 606 can be configured to automatically move from the depressed position to the non-depressed position in response to the user removing the pushing or pressing force on the housing 602.

The symbol 604 can be formed on the housing 602 adjacent to the activation member 606 disposed therein, e.g., positioned directly proximally above the activation member 606, which can facilitate user activation of the activation member. The symbol 604 can include instructional text such as "push here" or "press" to help a user properly use the accessory 600 and activate the activation member 606. Additionally or alternatively, written and/or audible instructions provided with the accessory 600 can instruct a user to push or press on the symbol 604 to dispense medication from the dispenser after the accessory 600 has been attached to the dispenser.

A void space 622 can exist between the button 606 and the housing 602 when the button 606 is in a non-depressed position, as in FIGS. 12 and 13. The void space 622 can provide some "give" space for movement of the button 606 within the housing 602, which can help prevent the button 606 from being accidentally depressed and thus help prevent the medication from being accidentally dispensed.

Figure 16:
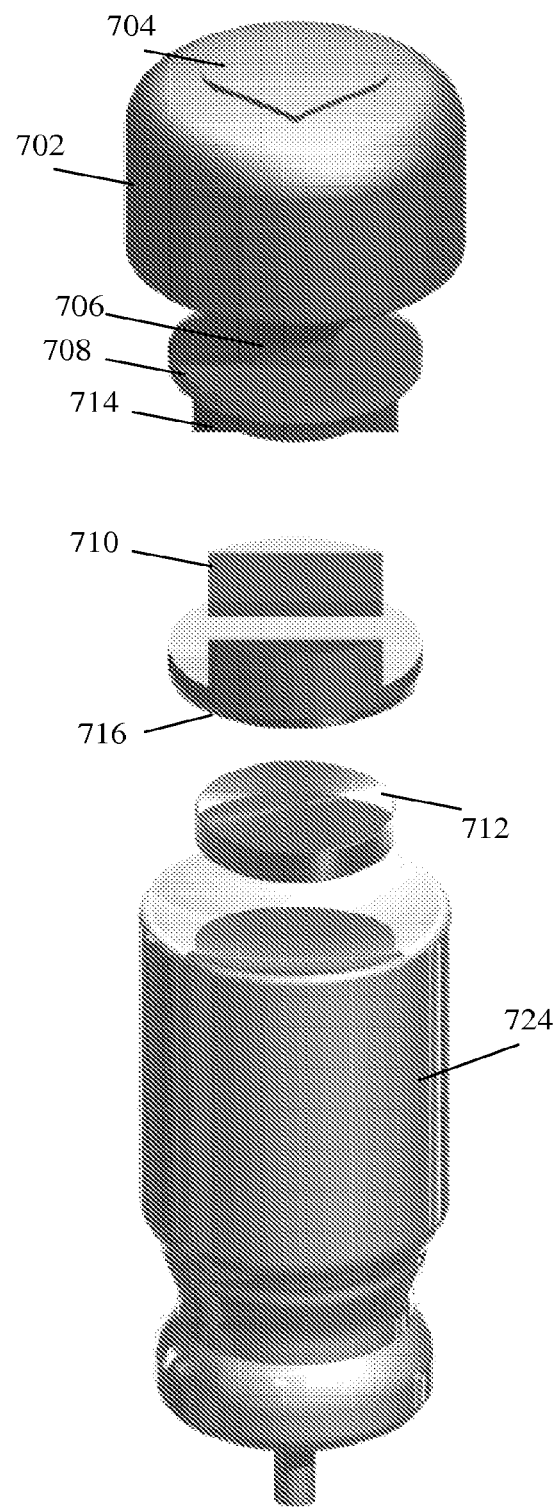
FIG. 16 is shows a perspective view of the canister of FIG. 14 and a perspective expanded view of the accessory of FIG. 14.
Figure 17:
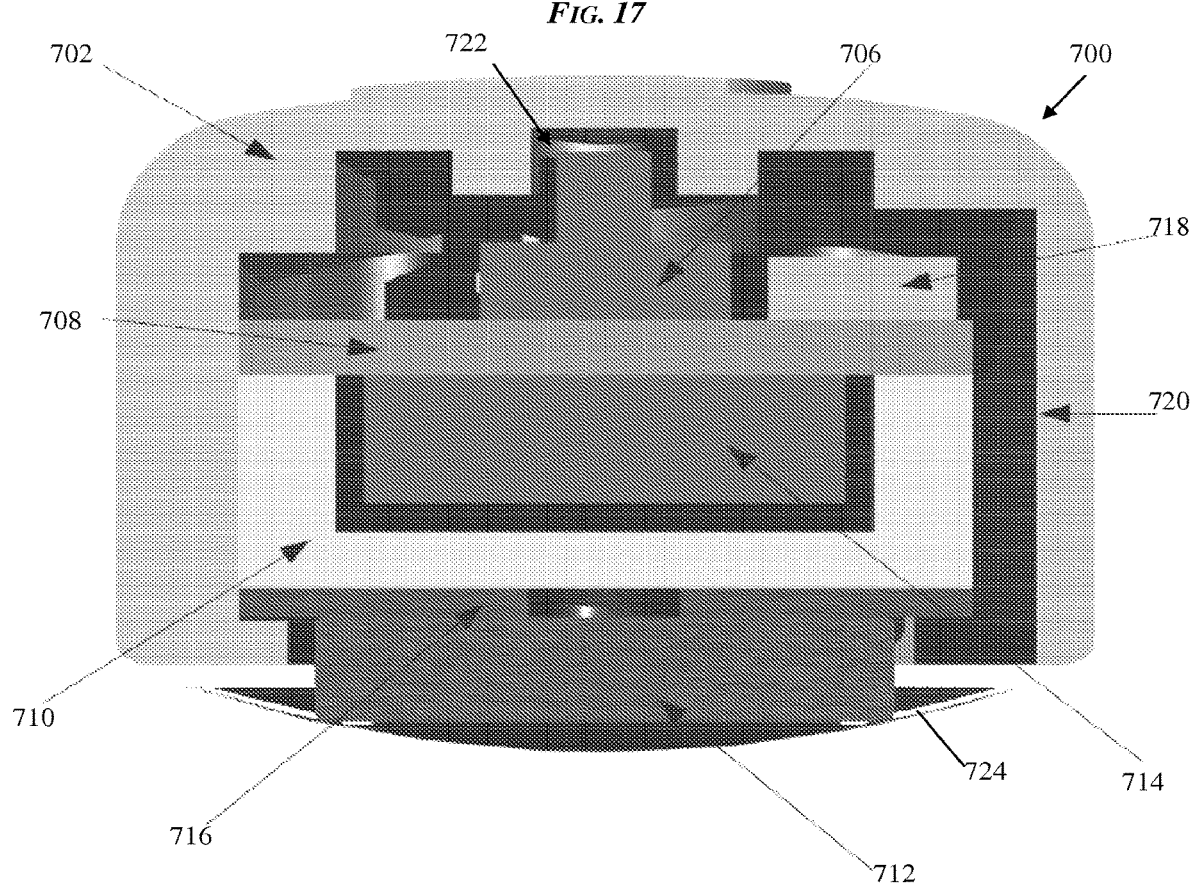
FIG. 17 is a side cross-sectional view of the accessory of FIG. 14 and a partial side view of the canister of FIG. 14.

FIGS. 14-17 illustrate another embodiment of a cap 700 that includes a housing 702 having a symbol 704 formed thereon, the symbol 704 being in the form of a heart-shaped protrusion. The cap 700 can be configured to removably and replaceably attached to a medication dispenser 724, as shown in FIGS. 14 and 17 in which the cap 700 is shown attached to the dispenser 724. The dispenser 724 in this illustrated embodiment includes a respiratory inhaler (only the medication-containing canister of which is shown in FIGS. 14-17), but as mentioned above, a cap can be configured to attach to other types of medication dispensers.

The housing 702 can have a variety of sizes. In the illustrated embodiment, the housing 702, and hence the cap 700, has a height 702H of 0.7 in. and a width 702W of 1 in, which can facilitate attachment of the cap 700 to an end of a standard sized respiratory inhaler.

As shown in FIGS. 15-17, the cap 700 can include an activation member 706 (in the form of a depressible button in this illustrated embodiment), a PCB 708, a support board 710 for the PCB 708, an attachment mechanism 712 (in the form of a magnet in this illustrated embodiment), a power source 714 (in the form of a coin cell battery in this illustrated embodiment), a washer 716 (a steel washer in this illustrated embodiment) configured to attract the magnet 712 and provide a buffer between the attachment mechanism 712 and the support board 710, a flexible flat cable (FFC) connector 718 configured to coupled to a FFC (not shown), and a FFC slot 720 configured to seat the FFC. A void space 722 can exist between the button 706 and the housing 702 when the button 706 is in a non-depressed position, as in FIGS. 14 and 17.

Referring again to FIG. 1, the wireless bridge 14 can have a variety of sizes, shapes, and configurations. The wireless bridge 14 can include a base station 38 and a router 40, as in the illustrated embodiment. A person skilled in the art will appreciate, however, that the wireless bridge 14 can include these and/or other components to facilitate electronic communication, similar to that discussed above regarding the network interface 32. The base station 38 and/or the router 40 can, as mentioned above, be included as part of the accessory 12 or can be remotely located therefrom, such as at the patient's home, the patient's school, the patient's work office, the patient's doctor's office, the patient's day care center, etc. The accessory 12 can be configured to communicate with only one base station 38, or with a plurality of pre-approved or pre-registered base stations 38, which can help ensure that data regarding the patient 22 is not transmitted to an unauthorized area.

Figure 18:
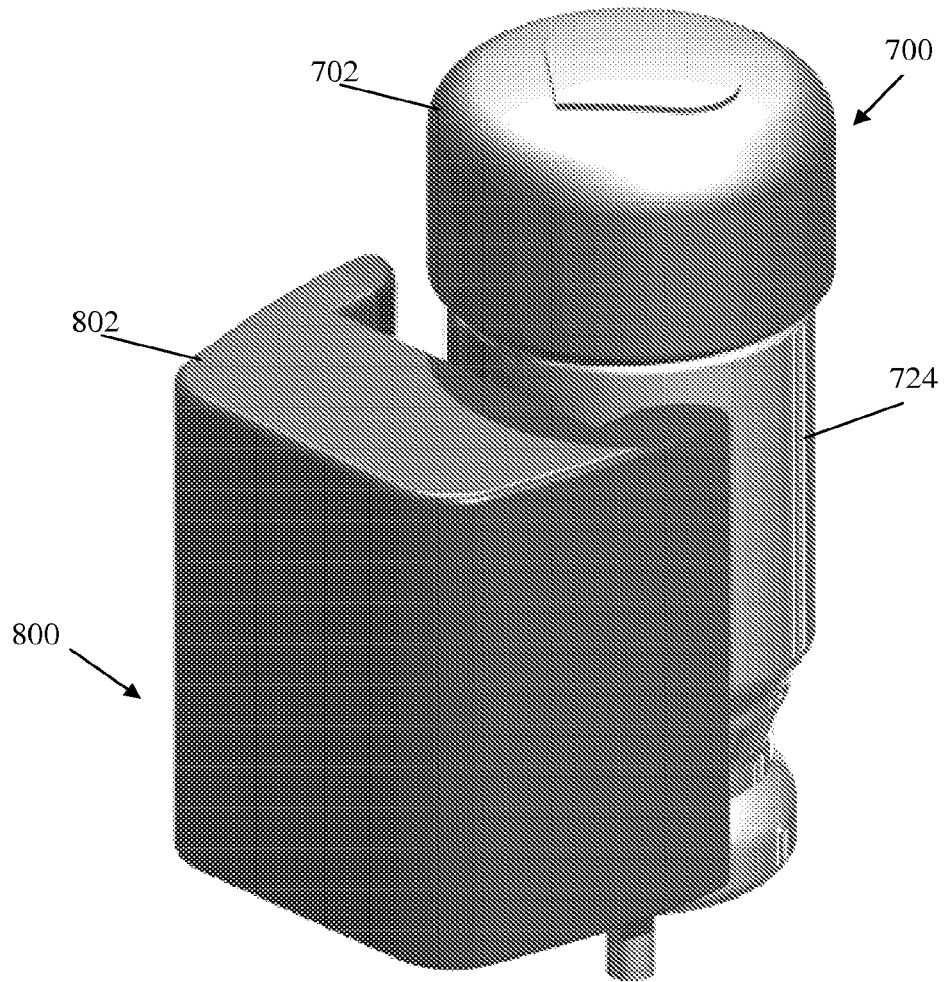
FIG. 18 is a perspective view of one embodiment of a wireless bridge removably and replaceably attachable to the canister and accessory of FIG. 14.
Figure 19:
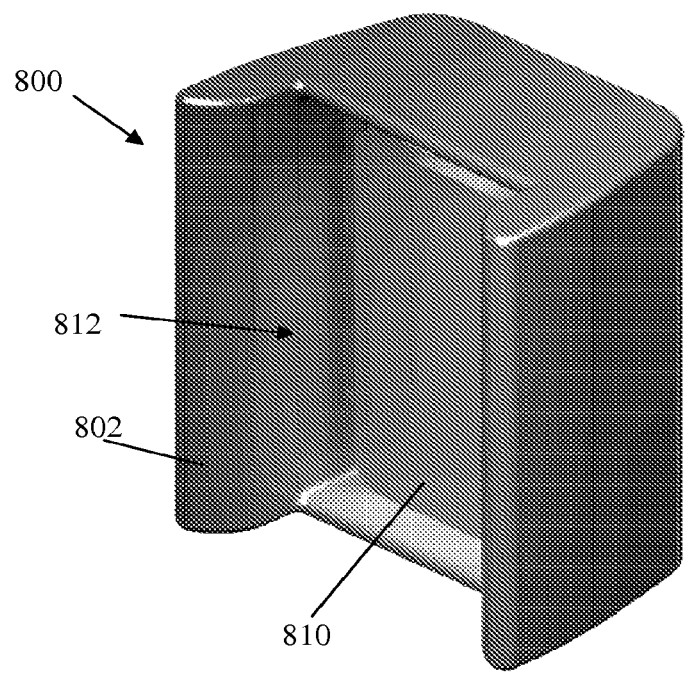
FIG. 19 is another perspective view of the wireless bridge of FIG. 18.
Figure 20:
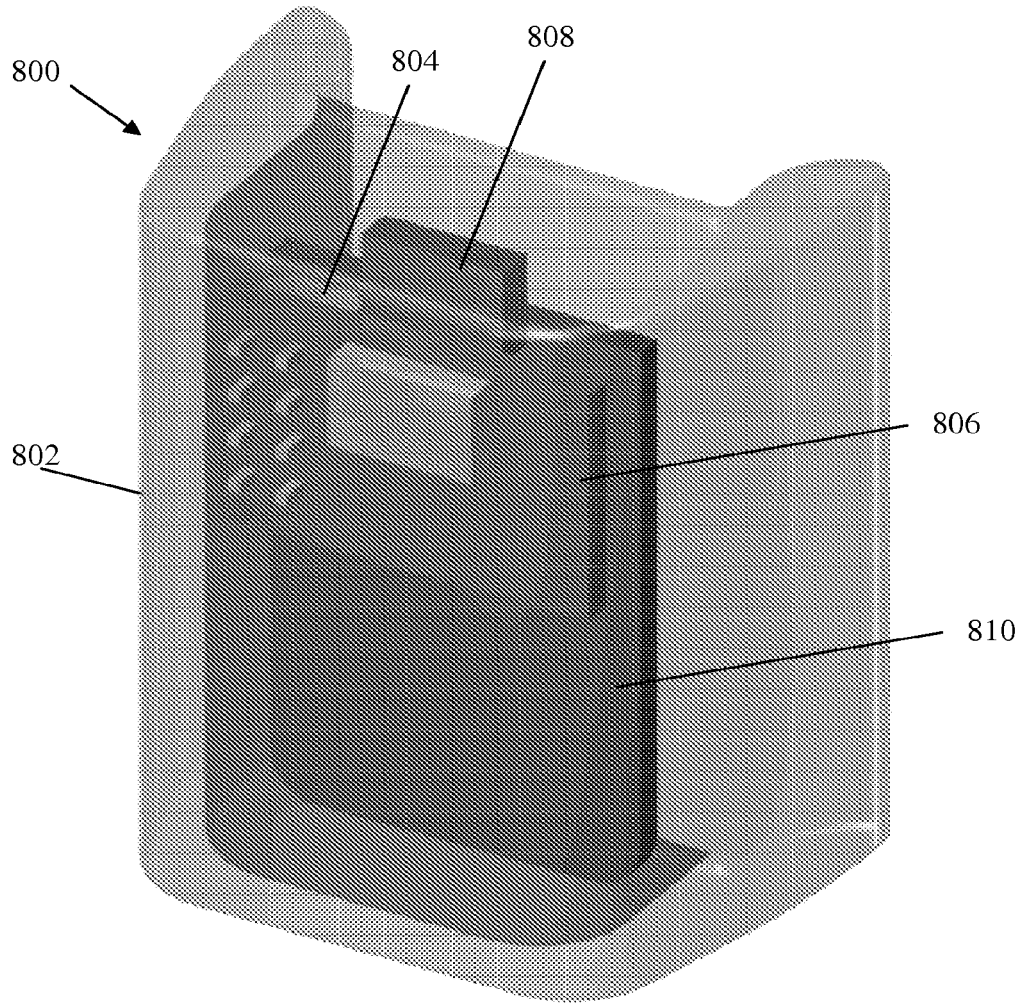
FIG. 20 is a perspective transparent view of the wireless bridge of FIG. 18.
Figure 21:
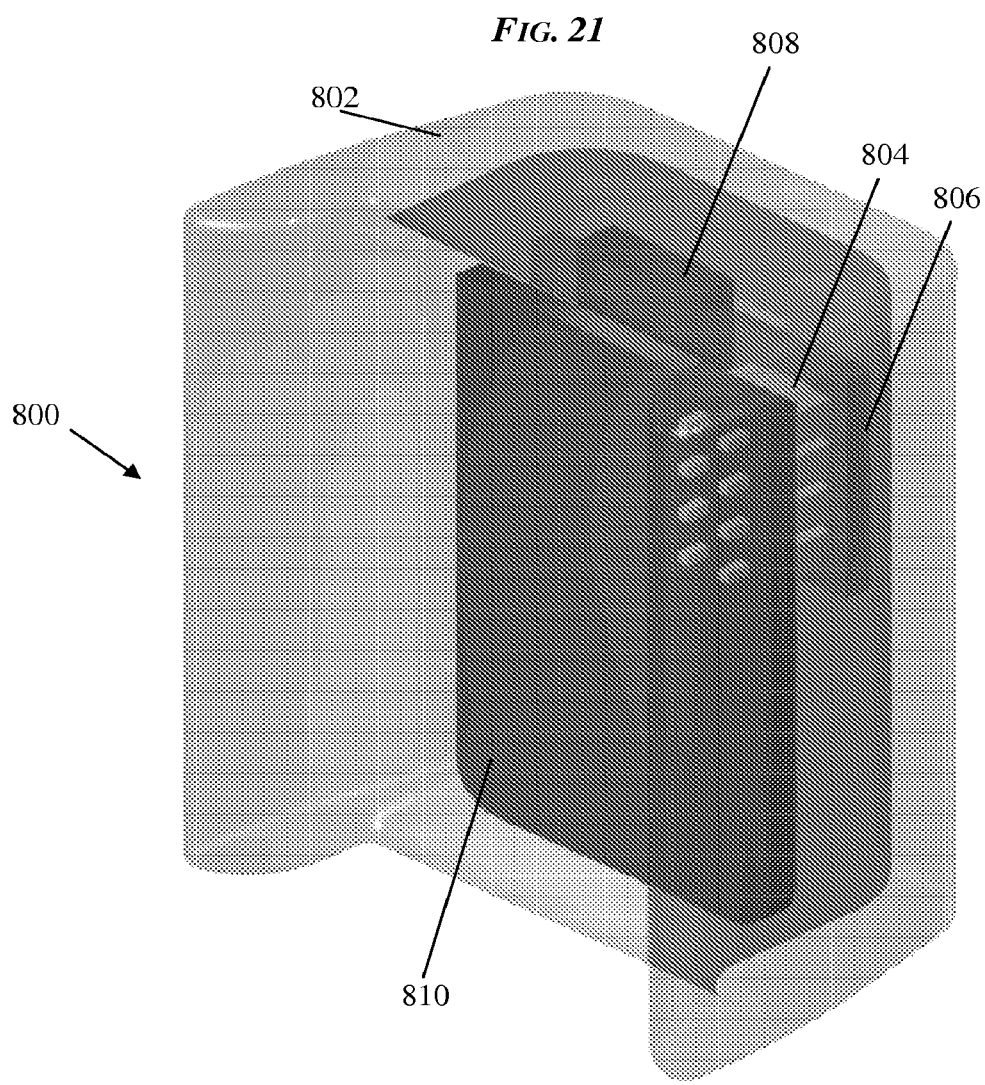
FIG. 21 is another perspective transparent view of the wireless bridge of FIG. 18.
Figure 22:
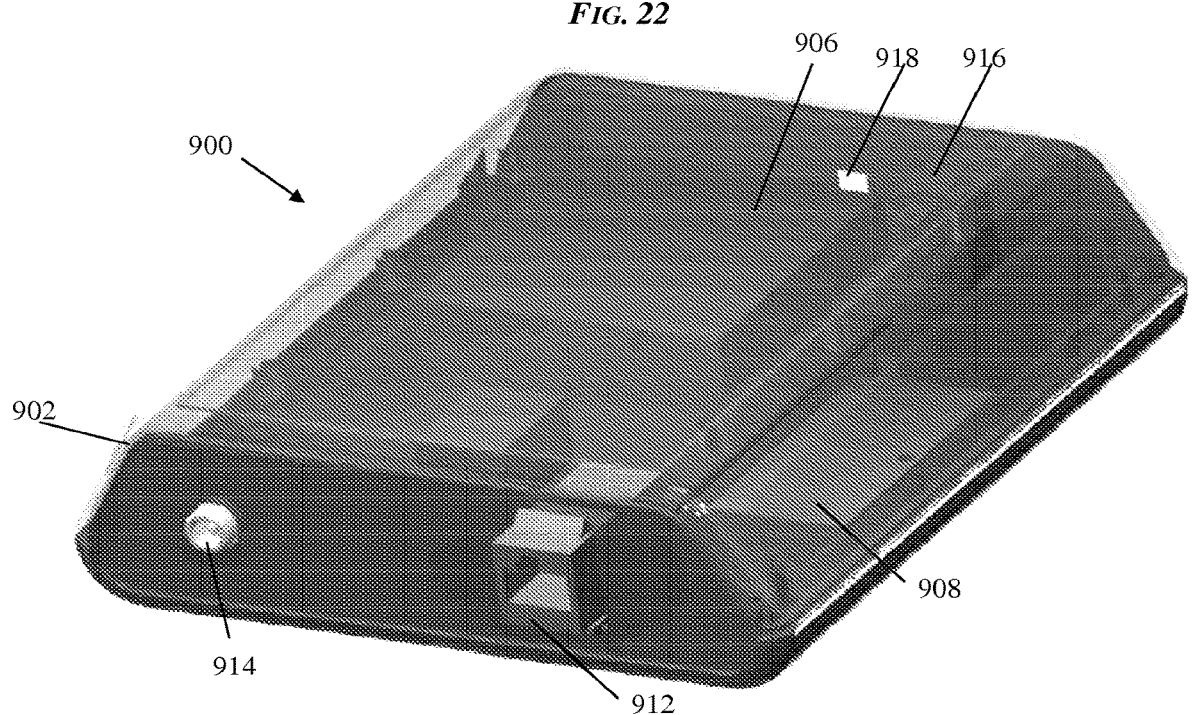
FIG. 22 is a perspective view of another embodiment of a wireless bridge.
Figure 23:
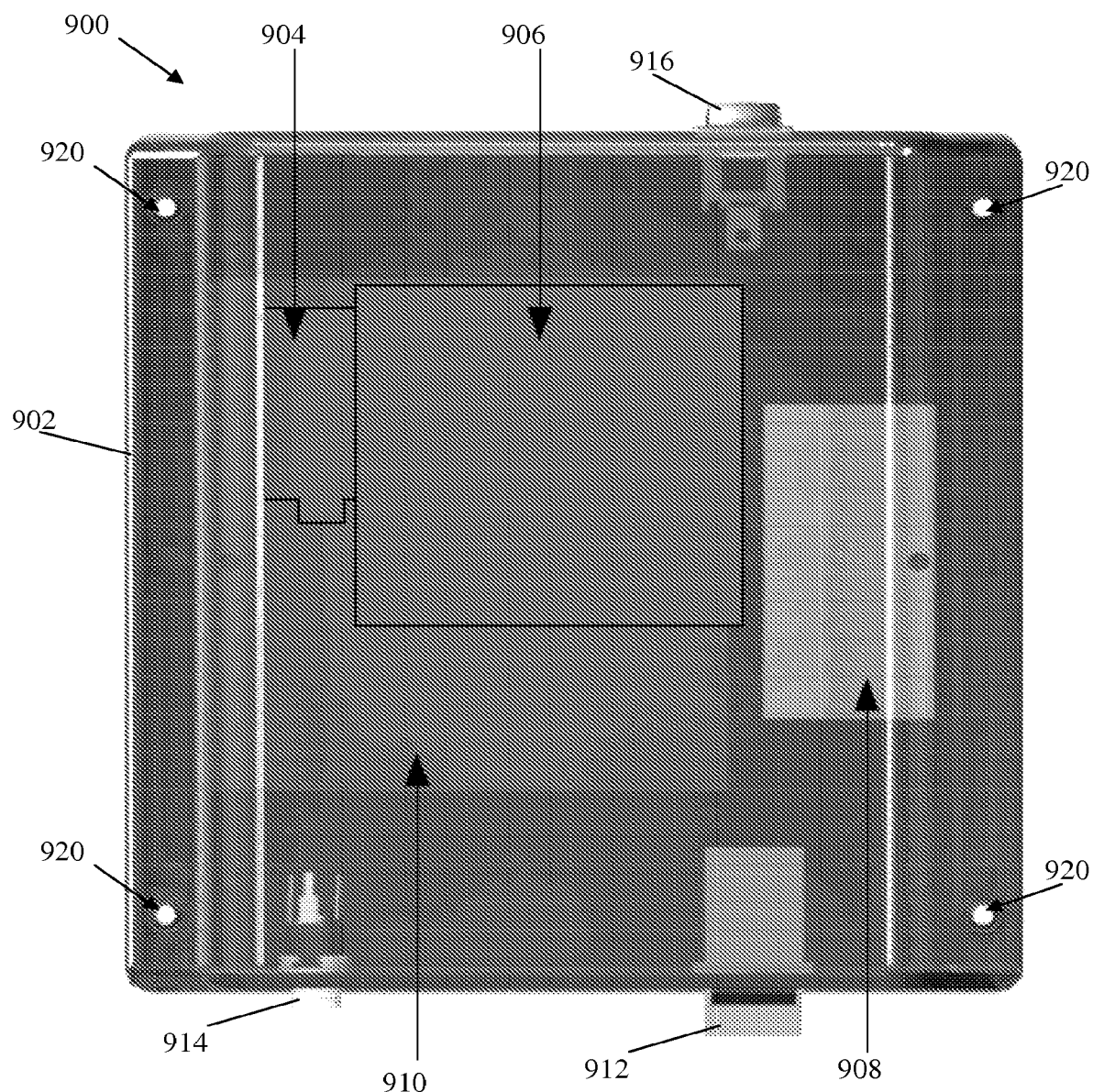
FIG. 23 is a bottom view of the wireless bridge of FIG. 22.
Figure 24:
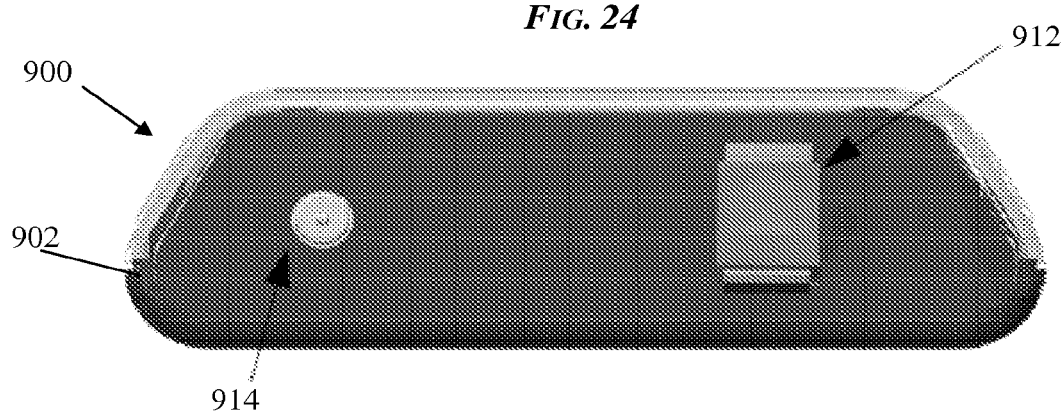
FIG. 24 is an end view of the wireless bridge of FIG. 22.
Figure 25:
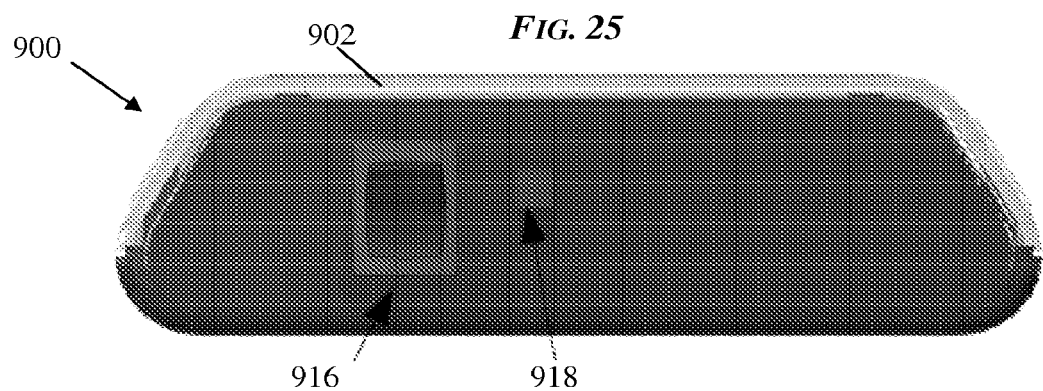
FIG. 25 is another end view of the wireless bridge of FIG. 22.

FIGS. 18-21 show another embodiment of a wireless bridge 800 configured to facilitate wireless communication. The wireless bridge 800 in this illustrated embodiment can be configured for use with another component of an accessory that includes at least an activation member. For example, the wireless bridge 800 can be used with a cap of an accessory, such as the cap 700 of FIGS. 14-17, as shown in the embodiment of FIG. 18. The wireless bridge 800 can be configured to be removably and replaceably attached to the same dispenser 724 as the cap 700. The wireless bridge 800 can be configured to be removably and replaceably attached to the same dispenser 724 independently of the cap 700 such that the cap 700 and the wireless bridge 800 can be selectively removed and replaced from the dispenser 724. In this way, if only one of the cap 700 and the wireless bridge 800 needs replacement, e.g., because of a drained power source, because of a broken part, etc., only the one of the cap 700 and the wireless bridge 800 needing replacement can be removed and replaced, which can help prevent waste. An accessory can therefore be configured to be removed and replaced from a medication dispenser in multiple parts, e.g., a cap of an accessory being removable separate from a wireless bridge of the accessory.

The wireless bridge 800 can include an attachment mechanism similar to that discussed above to facilitate removable and replaceable attachment of the dispenser 724. As in the illustrated embodiment, the wireless bridge 800 can include an attachment mechanism in the form of a cavity 812 formed therein to fit around a portion of the dispenser 724 in a press fit.

The wireless bridge 800 can include a housing 802, a wireless module 804, a CCS module 806, a power source 808 (in the form of a battery pack in this illustrated embodiment), and a power board 810. The housing 802 can, as in the illustrated embodiment, be configured to house the CCS module 806, the power source 808, and the power board 810 therein.

FIGS. 22-25 showing another embodiment of a wireless bridge 900 configured to facilitate wireless communication. The wireless bridge 900 can include a housing 902, a wireless module 904, a power source 906 (in the form of a battery pack in this illustrated embodiment), a power board 908, a CCS module 910, a connector port 912 (an Ethernet jack in the illustrated embodiment), a power jack 914, a power on/off element 916 (a switch in the illustrated embodiment), and a power indicator 918 (a light in the form of an LED in the illustrated embodiment). The wireless bridge 900 can include an attachment mechanism similar to that discussed above. As in the illustrated embodiment, the wireless bridge 900 can include an attachment mechanism in the form of screw holes 920 configured to each receive a screw (not shown) therein to be screwed into a housing of a medication dispenser.

The connector port 912 can allow the wireless bridge 900 to communicate via a wired connection, e.g., via an Ethernet cable, in addition to or in alternative to communicating wirelessly using the wireless module 904. Transmitting and receiving data via a wired connection can facilitate communication between the accessory and any external device and/or can facilitate on-demand transmission of data to the accessory and/or on-demand receipt of data from the accessory.

The power jack 914 can allow for external power to be provided to the wireless bridge 900, which can help conserve power of the on-board power source 906 and/or allow for communication of data from the wireless bridge 900 even if the power source 906 has been drained of power.

The power on/off element 916 can allow the power source 906 to be selectively turned on and off. This on/off capability can help conserve power, thereby prolonging the life of the power source 906 and hence of the wireless bridge 900. The power indicator 918 can be configured to visually indicate the on/off status, e.g., by illuminating when the element 916 is in the "on" position and by not being illuminated when the element 916 is in the "off" position.

As mentioned above, any of a variety of users can access, interact with, control, etc. a user interface, with the user interface optionally being customized for a category of a particular user, such as any one or more of a relationship of the user to the patient (e.g., the patient, a family member of the patient, a care provider for the patient, etc.), a gender of the user, and an age of the user. The user interface can provide data regarding any one or more aspects of a system including an accessory, medication associated with the accessory, and a patient associated with the medication. In addition to providing data to a user, the user interface can be configured to accept user input, e.g., via an I/O device, and data input by the user can be stored in any one or more memories. For example, the user interface can be configured to prompt a user to enter data in response to a question regarding medication administration that can help explain any anomalies, e.g., a question asking what the patient was doing or experiencing when emergency medication was administered (e.g., playing sports, sleeping, attending school class, suffering from allergies, etc.), etc., a question asking why a medication dosage was missed, etc. An accessory's processor and/or a processor located remotely from the accessory can be configured to analyze input answers so as to "learn" patient behavior and incorporate the "learned" behavior into, e.g., recommendations regarding the patient's treatment plan and predictions of the patient's future behavior.

The user interface can be configured to display an avatar for a user. The avatar can allow a user to be able to quickly and easily determine that they are viewing the correct page by seeing their avatar. The avatar can give the user interface a more personal feel, which can make the user interface more fun to use and thus more likely to be used, particularly by children. The avatar can be customizable by a user, as will be appreciated by a person skilled in the art.

Figure 26:
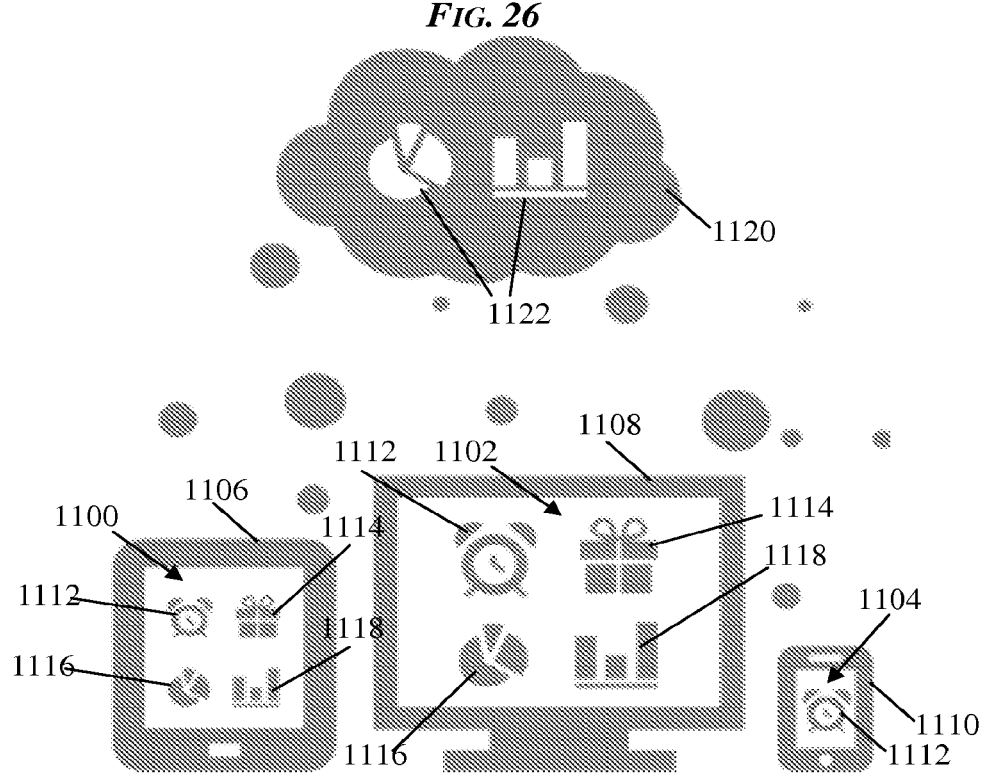
FIG. 26 is a schematic diagram showing embodiments of user interfaces and client terminals.

FIG. 26 shows general representations of embodiments of first, second, and third user interfaces 1100, 1102, 1104 on embodiments of first, second, and third client terminals 1106, 1108, 1110, respectively, that can provide information to various users (not shown). The first, second, and third client terminals 1106, 1108, 1110, are a tablet, a desktop computer, and a mobile phone, respectively, but as mentioned above, client terminals can have other forms.

Each of the user interfaces 1100, 1102, 1104 show symbolic representations of examples of different types of information that can be shown on a user interface. The embodiments of information types shown in the illustrated embodiment include medication dose notification data 1112 indicating that a medication dose is due for a patient according to the patient's predetermined medication schedule, incentive data 1114 indicating progress toward and/or achievement of one or more medication adherence goals, adherence data 1116 indicating adherence to one or more predetermined medication schedules, and patient treatment data 1118 indicating one or more patient treatment plans. Other examples of information types include accessory status data indicating status of an accessory, medication status data indicating status of medication in a medication dispenser, and prediction data indicating one or more predictions of a patient's future behavior based on the patient's historical adherence data. Any of the information types can be displayed using text and/or graphics. The information shown on the first, second, and third user interfaces 1100, 1102, 1104 can be provided over a network 1120, such as a cloud having access to information 1122, e.g., access to a database storing the information 1122, that can be provided to the client terminals 1106, 1108, 1110. Although certain types of information are shown on each of the user interfaces 1100, 1102, 1104, and in the cloud 1122, any type of information and any combination of information types can be shown on a user interface of any client terminal, subject to any user restrictions such as not allowing non-clinician users to view information regarding patients other than a specific patient authorized for a particular non-clinician user, and subject to any client terminal limitations such as a client terminal not being configured to show data having a certain file extension.

Figure 27:
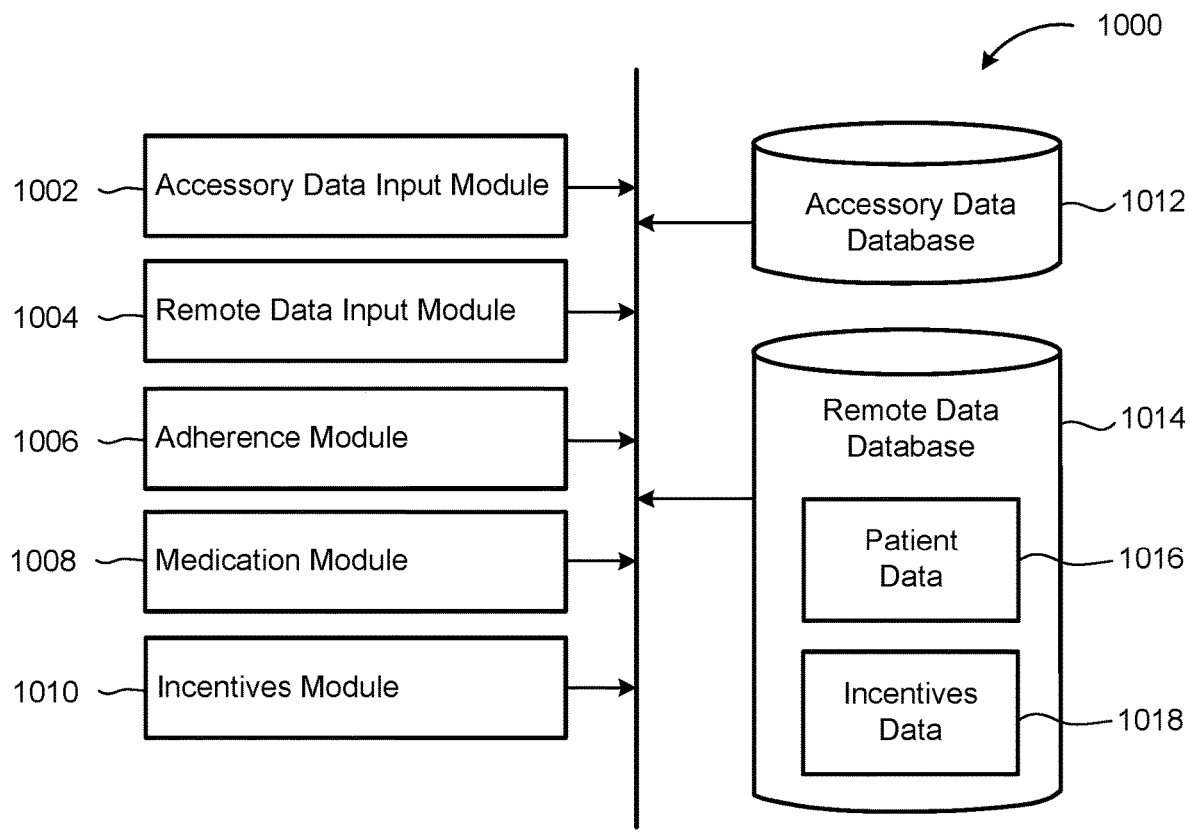
FIG. 27 is a schematic diagram of one embodiment of an adherence monitoring and patient interaction system.

FIG. 27 is a schematic block diagram of one exemplary embodiment of a medication analysis system 1000. The system 1000 can include a plurality of modules, discussed further below, which can each be implemented using one or more digital data processing systems of the type described above, and in particular using one or more web pages which can be viewed, manipulated, and/or interacted with using such digital data processing systems. The system 1000 can thus be implemented on a single computer system, or can be distributed across a plurality of computer systems. The system 1000 also includes at least one database, which can be stored on and accessed by computer systems. It will be appreciated by a person skilled in the art that any of the modules or databases disclosed herein can be subdivided or can be combined with other modules or databases.

The system 1000 can include an accessory data input module 1002, a remote data input module 1004, an adherence module 1006, and a medication module 1008, and an incentives module 1010. Any of the accessory data input module 1002, the remote data input module 1004, the adherence module 1006, and the medication module 1008, and the incentives module 1010 can be used independently from one another and can be used in combination with any one or more of the other modules 1002, 1004, 1006, 1008, 1010. Each of the modules 1002, 1004, 1006, 1008, 1010 is discussed further below in turn. Although each of the modules 2001002, 1004, 1006, 1008, 1010 is illustrated in FIG. 27 as a single-component module, each of the modules 1002, 1004, 1006, 1008, 1010 can include any number of component modules, e.g., one, two, three, etc., the same or different from any of the other modules 1002, 1004, 1006, 1008, 1010. Further, as mentioned above, it will be appreciated by a person skilled in the art that any of the modules 1002, 1004, 1006, 1008, 1010, and any of their various component modules, can be subdivided or can be combined with other modules, including modules illustrated in FIG. 27 as being in different ones of the modules 1002, 1004, 1006, 1008, 1010.

The system 1000 can also include an accessory data database 1012 and a remote data database 1014. The accessory data database 1012 can be configured to be accessible by the accessory data input module 1002 and to store data regarding a mechanical accessory. The remote data database 1014 can be configured to be accessible by the remote data input module 1004 and to store data regarding patients in a patient database 1016 and data regarding incentives in an incentives database 1018. Each of the databases 1012, 1014 is discussed further below in turn with respect to various modules 1002, 1004, 1006, 1008, 1010. Each of the databases 1012, 1014 can include any number of component databases, e.g., one, two, three, etc., the same or different from any of the other databases 1012, 1014. As mentioned above, a person skilled in the art will appreciate that any of the databases 1012, 1014, and any of their various component databases (if any), can be subdivided or can be combined with other databases, including databases illustrated in FIG. 26 as being in different ones of the databases 1012, 1014. Any portion of any of the databases 1012, 1014 can be configured to be accessed, e.g., read from and/or written to, by any one or more of the modules 1002, 1004, 1006, 1008, 1010 and any additional module(s) (if any). Although the system 1000 in the illustrated embodiment stores data in database(s), any of the systems disclosed herein can store data in database(s) and/or in other memor(y/ies).

Figure 28:
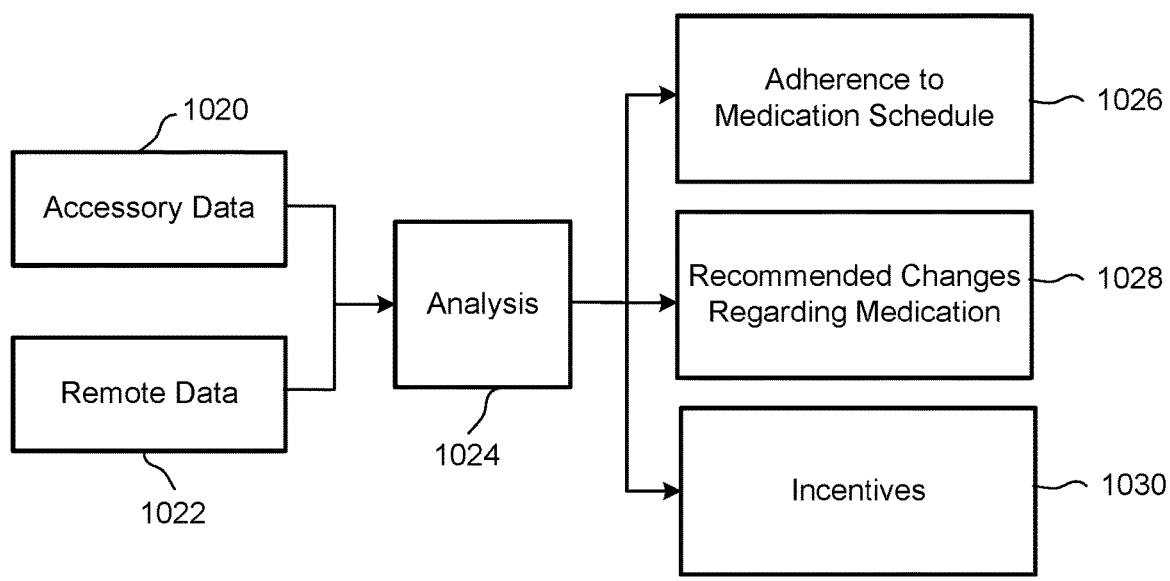
FIG. 28 is a schematic diagram of the adherence monitoring and patient interaction system of FIG. 27.

Generally, as illustrated in FIG. 28, and as discussed in further detail below, the system 1000 can be configured to allow patient data 1020 to be input via the accessory data input module 1002 and remote data 1022 to be input via the remote data input module 1004. The adherence module 1006 can be configured to analyze 1024 the input patient data 1020 and/or the input remote data 1022 so as to output 1026 an indication of at least one patient's adherence to a predetermined medication schedule. The medication module 1008 can be configured to analyze 1024 the input patient data 1020 and/or the input remote data 1022 so as to output 1028 one or more recommended changes to a patient's predetermined medication schedule, one or more recommended changes to how soon before a dose is due are medication dose notifications provided to the patient by an accessory attached to a medication dispenser, and/or one or more recommended changes to a patient's medication. The incentives module 1010 can be configured to analyze 1024 the input patient data 1020 and/or the input remote data 1022 so as to output 1030 incentives data for at least one patient.

The accessory data input module 1002 can generally allow an accessory to input data regarding the accessory to the system 1000. The submitted accessory data can then be used by the adherence module 1006, the medication module 1008, and/or the incentives module 1010 to perform various analyses 1024 that can result in output(s) to a user via the user interface, as discussed further below. The user interface configured to allow users to access data can have a variety of configurations. The user interface can be configured to be displayed on a client terminal.

As mentioned above, the accessory data input module 1002 can be configured to read information from and/or write information to the accessory data database 1012. Thus, the accessory data input module 1002 can be configured to write submitted accessory data to the accessory data database 1012. The accessory data can be organized in any way in the accessory data database 1012 and/or in one or more other memories accessible by the system 1000. In an exemplary embodiment, accessory data can be stored in a table in the accessory data database 1012 such that each accessory has his/her own row or column of data populated with data related to that accessory. However, as will be appreciated by a person skilled in the art, accessory data can be stored in any way.

The accessory data input module 1002 can be configured to automatically gather accessory data, e.g., according to a schedule programmed into a client terminal able to access the system 1000, and/or can be configured to passively receive accessory data as transmitted by an accessory, e.g., according to a schedule programmed into the accessory. In an exemplary embodiment, the accessory data input module 1002 can be configured to automatically gather data and to passively receive accessory data, thereby maximizing an amount of data that the system 1000 can consider in performing various analyses 1024.

The accessory data input module 1002 can be configured to receive a variety of different types of data regarding an accessory. The accessory data include any type of data configured to be gathered, sensed, and/or analyzed by an accessory, as discussed above. Examples of accessory data include data regarding medication that was dispensed from the accessory (e.g., a date the medication was dispensed, time the medication was dispensed, an amount of medication dispensed at a particular date/time, whether medication was dispensed at a date/time consistent with the patient's predetermined medication schedule, etc.), failure data regarding any of the accessory's components, low or depleted power source data, data regarding a dosage not dispensed as prescribed in a predetermined medication schedule, identification information (e.g., a serial number of the accessory, an identification code for the patient associated with the accessory, etc.), etc.

The remote data input module 1004 can generally allow patient data and incentives data to be input to the system 1000 and stored remotely from accessor(y/ies) associated therewith. The submitted patient data and/or the incentives data can then be used by the adherence module 1006, the medication module 1008, and/or the incentives module 1010 to perform various analyses 1024 that can result in output(s) to a user via the user interface, as discussed further below.

As mentioned above, the remote data input module 1004 can be configured to read information from and/or write information to the remote data database 1014. Thus, the remote data input module 1004 can be configured to write submitted data to the remote data database 1014. The data can be organized in any way in the remote data database 1012 and/or in one or more other memories accessible by the system 1000. In an exemplary embodiment, patient data can be stored in a table in the patient data database 1016 such that each patient has his/her own row or column of data populated with data related to that patient, and general incentives data can be stored in the incentives database 1018. However, as will be appreciated by a person skilled in the art, remote data can be stored in any way. The remote data input module 1004 can be configured to automatically gather and/or can be configured to passively receive data, similar to that discussed above regarding the accessory data input module 1002.

The remote data input module 1004 can be configured to receive a variety of different types of data, such as patient data and incentives data. Examples of patient data include identification information for the patient (e.g., medical record number, name, etc.), care provider data for the patient (e.g., the patient's primary care physician, any specialist(s) who have treated the patient, etc.), clinical trial data for a clinical trial involving the medication and the patient, medication data (e.g., types of medication prescribed to the patient, predetermined medication schedules for medication being taken by the patient, any patient allergies, etc.), and medical history data for the patient. Examples of incentives data include patient goal data (e.g., benchmarks to achieve rewards, etc.), goal progress data (e.g., progress toward the benchmarks, etc.), rewards data (e.g., available virtual and/or physical rewards for achieving a benchmark, etc.), and historical goal data (e.g., goals previously reaches, time periods needed to achieve benchmarks, etc.).

The adherence module 1006 can generally provide users of the system 1000 with a user interface for receiving one or more reports regarding one or more patients' adherence to the patients' individual predetermined medication schedules. The adherence module 1006 can be configured to provide a user of the system 1000 with at least one textual and/or graphic report indicating a selected patient's adherence to a predetermined medication schedule for a medication dispensable from a dispenser having an accessory attached thereto. The adherence report(s) can facilitate evaluation of the patient's use of the medication, of the patient's predetermined medication schedule, and/or of the patient's overall treatment plan.

The adherence module 1006 can be configured to provide a user of the system 1000 with textual and/or graphical adherence data indicating a plurality of patients' adherence to the patients' individual predetermined medication schedules for a certain type of medication. The adherence data can facilitate an overall evaluation of how easily or difficult patients find adhering to schedules for this medication and/or a comparison of a particular patient's adherence with other patients taking the same medication. The adherence data can thus help a care provider adjust one or more patients' treatment plans by, e.g., changing to a different medication and/or adjust the predetermined medication schedules.

The adherence data can be shown for a patient over a predetermined time period, e.g., a time period previously set as a default for a particular user or a single available time period. The predetermined period can be adjustable, such as by allowing a user to select a time period. Examples of time periods include time elapsed for the current date, 24 hours, one month, one week, two weeks, three days, etc. In general, the longer the time period, the easier it can be to determine a patient's pattern of adherence.

Each of the time periods can cause a different set of data to be displayed. For example, a time period of less than one week can show complete adherence data for each day in the time period, while a time period of one week or greater can show only selected adherence data in order to allow all the days in the time period to be simultaneously shown on a limited amount of screen space.

The adherence data can include information regarding a patient's compliance with the patient's predetermined medication schedule, such as whether the patient took a required medication dose at the required day/time. As will be appreciated by a person skilled in the art, a patient can be considered to have taken medication on schedule even if not precisely at the required date/time. An acceptable amount of time deviation from a required time for a medication dose can be preprogrammed into the system. The acceptable amount of deviation can vary based on, e.g., a type of the medication. Other information regarding the patient's compliance with the patient's predetermined medication schedule can include information regarding any off-schedule medication doses administered to the patient. Such off-schedule administration can indicate emergency use of the medication or of a different medication to treat immediate symptoms, such as a rescue use of an inhaler to treat an asthma attack.

In one embodiment, the user interface can show adherence data for a single medication being taken by a single patient. The user interface can thus provide focused information regarding the patient and the medication, which can help highlight any anomalies regarding this particular medication for this patient. In another embodiment, the user interface can show adherence data for a plurality of medications being taken by a single patient. The user interface can thus provide a medication overview for the patient, which can help in evaluating a patient's overall treatment plan. In yet another embodiment, the user interface can show adherence data for a single medication being taken by a plurality of patients. The user interface can thus help highlight any anomalies regarding this particular medication for a patient population. In another embodiment, the user interface can show adherence data for a plurality of medications each being taken by a plurality of patients. The user interface can thus facilitate evaluation of a treatment plan for a particular ailment that involves prescribing the plurality of medications.

The user interface can be configured to show different adherence data for different users, e.g., show only graphical adherence data to patients under a certain age; show different, more complicated graphics or icons to adults than to children; show prescription data only to clinicians; provide different tips for improving adherence to family members of a patient than to the patient; ask different questions regarding adherence to family members of a patient than to the patient (e.g., ask a family member if they were present or not for a scheduled but missed medication dose, ask a patient why a dose was missed, ask a patient if a dose that was taken was scheduled at an inconvenient day/time, etc.); etc.

The adherence module 1006 can be configured to determine predictions of a patient's future behavior based on the patient's historical adherence data. The adherence module 1006 can be configured to access the patient's historical adherence data, e.g., from the database 18, and analyze 1024 the patient's historical adherence data to make one or more predictions of future behavior. Examples of predicted future behavior include a prediction of changes in the patient's health based on the patient's compliance (e.g., the patient's condition being predicted to deteriorate at a certain rate if medication doses keep being missed at the rate detected for the previous month or other previous time period, the patient's condition being predicted to improve based on the patient's steadily decreasing number of emergency medication doses, etc.), a prediction of the patient's future adherence to the patient's predetermined medication schedule based on the patient's compliance (e.g., predicting the patient to comply less with the schedule in the following month than in the preceding month based on multiple previous consecutive months of continuously reduced compliance, etc.), and a comparison of the patient's compliance with a plurality of other patients' compliance with their respective predetermined medication schedules (e.g., the patient being below average compliance, the patient being above average compliance, etc.).

Figure 29:
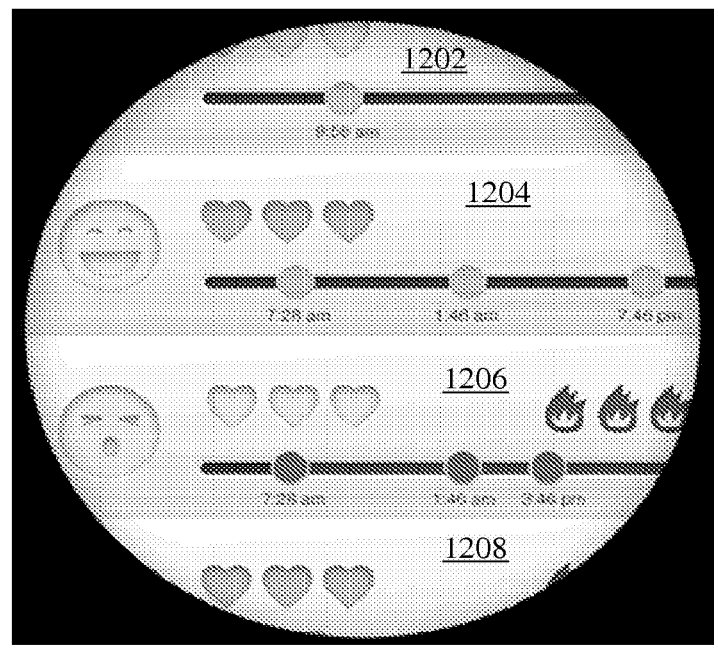
FIG. 29 is a schematic diagram of one embodiment of a user interface showing adherence information.

FIG. 29 illustrates one embodiment of a user interface 1200 configured to be displayed on a client terminal (not shown) and show adherence data. The user interface 1200 includes adherence information for a plurality of days 1202, 1204, 1206, 1208. The adherence information for each of the days 1202, 1204, 1206, 1208 can indicate a time, which can be shown by markers (e.g., circular dots) along a timeline, when medication was dispensed from a dispenser (e.g., as determined by an accessory attached to the dispenser). The markers can indicate, e.g., by color-coding, whether the medication was dispensed at a time corresponding to a regularly scheduled medication dose or whether the medication was dispensed at an unscheduled time. The user interface 1200 can indicate a total number of medication doses taken in a day by, e.g., showing an icon such as a heart for each taken regularly scheduled medication dose. The user interface can indicate a total number of unscheduled medication doses taken in a day by, e.g., showing an icon such as a flame for each taken unscheduled medication dose. The user interface 1200 can thus clearly show each day's medication usage and whether the medication was taken regularly or irregularly, thereby facilitating evaluation of the patient's health and treatment plan. The user interface 1200 can show any missed medication doses, e.g., doses not taken at a prescribed day/time, such as by providing a color-coded marker along the timeline at a missed medication time. The unscheduled medication dose(s) can be of the medication or can be a second, different medication. The user interface 1200 can thus be configured to display information for a plurality of medications being taken by a patient. The second medication can be contained within a second medication dispenser having a second accessory attached thereto. The second accessory can generally be configured and used similar to the accessory associated with the medication such that data regarding the second medication can be gathered and analyzed similar to that for the medication. For example, the scheduled medication can include a patient's asthma maintenance medication prescribed for regular use, and the second medication can include a patient's asthma rescue medication prescribed for emergency situations in which the patient needs immediate asthma treatment.

The user interface 1200 can provide an overall rating for each of the days 1202, 1204, 1206, 1208, such as by showing a success icon (only shown for two days 1204, 1206 in FIG. 29) for each of the days. The user interface 1200 can thus allow the user to quickly assess whether or not the patient has been adhering well by quickly scanning the overall ratings provided on the user interface 1200. The more unscheduled medication doses taken per day, the lower the day's success rating, and the more scheduled medication doses missed, the lower the day's success rating. The overall rating is shown in the illustrated embodiment using images of faces of varying expression (e.g., in order of most successful to least successful: large smile, small smile, no expression, small frown, large frown), but overall ratings can be provided in other ways (e.g., using text only or using a graphic other than smiling/frowning faces). The user interface 1200 can be configured to provide, in addition to or instead of a daily overall rating, an overall rating for a time period longer than one day, such as three days, one week, two weeks, etc. Providing such an extended rating can help provide, at a glimpse, a summary of the patient's medication usage.

Although not shown in FIG. 29, the user interface 1200 can include a key identifying the various symbols that can be shown on the user interface 1200, e.g., a heart icon indicating a taken scheduled dose, a flame icon indicating an unscheduled medication dose, a bomb icon indicating a missed scheduled dose, a textual explanation of each possible smiling/frowning face, etc.

Figure 30:
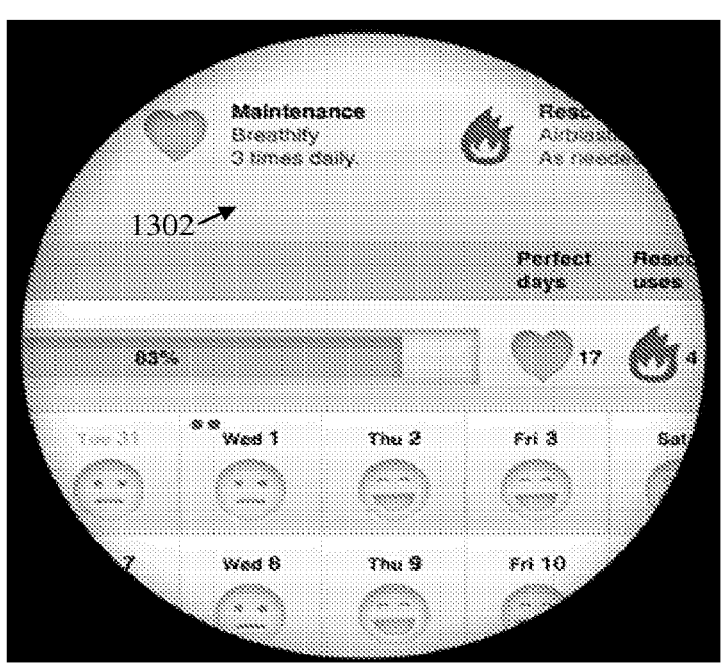
FIG. 30 is a schematic diagram of another embodiment of a user interface showing adherence information.

FIG. 30 illustrates another embodiment of a user interface 1300 configured to be displayed on a client terminal (not shown) and show adherence data. The user interface 1300 includes adherence information for a selected month. The user interface 1300 can be configured to allow the user to select which month to display. Similarly, the user interface 1300 can allow the user to switch between different views, e.g., between a month view such as FIG. 30's user interface 1200 and a multi-day view such as FIG. 29's user interface 1200. The adherence information in a multi-day view, such as this monthly view, can include an overall rating for each of the days in the month, thereby providing a quick summary of the patient's adherence over a month. The overall ratings in the illustrated embodiment include smiling/frowning faces provided for each day and an overall percentage for the month, but as indicated above, overall ratings can be provided in other ways.

FIG. 30 shows an embodiment in which a key 1302 for symbols is provided on the user interface 1300. The key 1302 is shown at a top of the user interface 1300 in the illustrated embodiment, but the key 1302 can be provided anywhere, and can be configured to be selectively shown and hidden by a user, such as by the user clicking on a "key" button (not shown) on the user interface 1300.

The adherence information in a multi-day view, such as this monthly view, can include one or more total counts for various adherence data. Examples of total counts include a total count of taken scheduled doses for the days in the current view, a total count of unscheduled medication doses for the days in the current view, a total count of missed scheduled dose for the days in the current view, a total count of days in the current view in which all scheduled medication doses were taken and no unscheduled doses were taken (so-called "perfect days"), a total count for each possible overall rating, etc.

Figure 31:
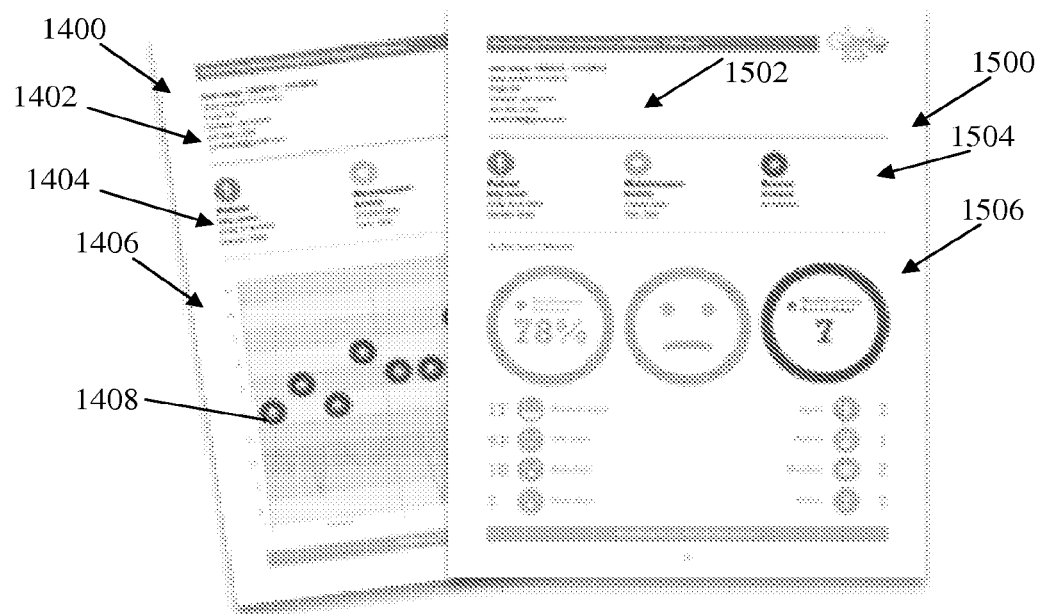
FIG. 31 is a schematic diagram of other embodiments of user interfaces showing adherence information.

FIG. 31 shows two other embodiments of user interfaces 1400, 1500 configured to be displayed on a client terminal (not shown) and show adherence data. The user interfaces 1400, 1500 each include patient identification information 1402, 1502 (e.g., patient name, patient address, and patient identification code), a key 1404, 1504 of symbols provided thereon, and a summary 1406, 1506 of adherence data for a selected time period, which for each of the user interfaces 1400, 1500 in these embodiments is one month.

One of the user interfaces 1400 shows a graphical summary 1406 of medication dosages taken during the month, each day of the month being plotted on the graph. The graphical summary 1406 also indicates, via alert symbol 1408, each day in which an unscheduled medication dose was dispensed. The other of the user interfaces 1500 shows a summary of medication dosages taken during the month in a different way than the user interface 1400. The user interface 1500 shows total counts for various activities in the month (e.g., 17 medication doses taken on schedule, 63 medication doses taken off but near schedule, 10 missed scheduled medication doses, 2 emergency medication doses, and 7 "perfect days"). The user interface 1500 also shows an overall rating for the month, in the form of a smiling/frowning face, and an overall percentage for the month. By showing both scheduled medication doses taken and unscheduled medication doses taken, the user interfaces 1400, 1500 can facilitate understanding by patients, patient family members, doctors, etc. that as adherence decreases, e.g., as patients miss more scheduled medication doses, unscheduled medication use increases.

The medication module 1008 can generally provide users of the system 1000 with a user interface for receiving one or more textual and/or graphic reports regarding one or more patients' medication. The medication report(s) can facilitate evaluation of the currently prescribed type and amount of medication as an effective treatment for the patient.

The medication report(s) can provide one or more recommended changes to a patient's predetermined medication schedule, such as a shift of all medication doses one hour earlier if the patient is consistently missing the last scheduled dose of the day, shifting days of medication being due to only weekdays since weekend medication doses are being consistently missed, etc. The report(s) can provide one or more recommended changes to how soon before a dose is due are medication dose notifications provided to the patient by an accessory attached to a medication dispenser, such as five minutes before a dose is due instead of one minute because doses are being consistently taken a few minutes late, providing multiple notifications for each scheduled dose (e.g., notifications being provided ten minutes before doses are due in addition to five minute reminders already being provided, etc.) because the patient is consistently missing doses, etc. The report(s) can provide one or more recommended changes to a patient's medication, e.g., recommending switch from a cream to a pill since an inadequate amount of cream is consistently being dispensed for each dose, recommending a stronger prescribed strength of medication because rescue doses are consistently being taken between regularly scheduled doses, etc.

The incentives module 1010 can generally provide users of the system 1000 with a user interface for receiving one or more reports regarding one or more patients' adherence goals and one or more incentives for reaching each of the goals. The incentives module 1010 can be configured to provide a user of the system 1000 with at least one textual and/or graphic report indicating a selected patient's adherence goal(s) for a predetermined medication schedule and the patient's progress toward the goal(s). The incentives report(s) can thus reflect a patient's adherence to the patient's predetermined medication schedule. The incentives report(s) can help encourage patient adherence to predetermined medication schedules by providing rewards (virtual and/or physical) for achievement of goals, and/or the incentives report(s) can facilitate evaluating success of the patient's medication use, the patient's predetermined medication schedule, and/or the patient's overall treatment plan.

At least one incentive available for a patient can be based on a patient's performance of a predetermined number of specific tasks within a certain time period. The predetermined number can be predetermined by the incentives module 1010 and can optionally be customizable by a user, e.g., be adjusted by a patient's care provider. The user interface can be configured to display a patient's progress toward each of the patient's goals, such as by showing a percentage of the patient's met medication doses, by showing a progress bar indicating how many more particular events must take place to reach the goal, etc. The patient's progress can be shown simultaneously for all the goals, or the user interface can be configured to allow the user to select which progress, if any, to show on the user interface.

One example of an incentive based on a patient's performance of a predetermined number of specific tasks within a certain time period include a patient taking their medication on schedule a certain number of times within a certain time period (e.g., 90% of the time over the course of a month, 100% of the time over the course of a day, 100% of the time over the course of a week, 75% of the time over the course of a month, etc.). In other words, the goal for the patient can be adhering to their predetermined medication schedule a set number of times over the course of a preset time period.

Another example of an incentive based on a patient's performance of a predetermined number of specific tasks within a certain time period include a patient taking zero off-schedule doses of the medication. In other words, the goal for the patient can thus be avoiding emergency use of the medication.

Yet another example of an incentive based on a patient's performance of a predetermined number of specific tasks within a certain time period include a patient dispensing medication within a predetermined amount of time after a dosage of medication is due as indicated by the patient's predetermined medication schedule. In other words, the goal for the patient can include the patient dispensing medication on time a certain number of times, taking into account that medication will almost never be dispensed at the exact moment a notification is provided.

In addition to or instead of incentive(s) based on performance of certain tasks within a certain period of time, at least one incentive for a patient can be based on a patient's performance of a single specific task. One example of such an incentive includes the patient taking a dose of medication when scheduled to do so per the patient's predetermined medication schedule. In other words, the goal for the patient can be taking each prescribed medication dose. Another example of such an incentive includes the patient removing an accessory from one medication dispenser (e.g., a dispenser low on or empty of medication) and attaching the accessory to another medication dispenser (e.g., a dispenser full of medication). In other words, the goal for the patient can be ensuring that medication is always available for a required dose. Another example of such an incentive includes the patient inputting an answer to a pop-up question provided on the user interface. In other words, the goal for the patient can be providing requested input data.

In addition to or instead of incentive(s) based on performance of certain tasks within a certain period of time and/or being based on a patient's performance of a single specific task, at least one incentive for a patient can be based on a user other than the patient performing one or more certain tasks. The other user(s) performance of the task(s) can contribute to the patient's progress toward his/her goal(s), or the other user(s) performance of the task(s) can contribute to the other user's own goal(s) having reward(s) associated therewith. One example of such an incentive includes inputting an answer to a pop-up question provided on the user interface. In other words, the goal can be providing requested input data. Another example of such an incentive includes multiple users providing an answer to the same pop-up question, e.g., the patient and the patient's parent each provide an answer to the same pop-up question (e.g., "Why was emergency medication taken?"). If the patient and the other user(s) independently input the same answer to the same pop-op question, the contribution to the patient's progress toward his/her goal(s) can be accelerated. Communication between parties interested in the patient's health can therefore be facilitated. If the patient and the other user(s) input different answers to the same question, at least one of the patient and the other user(s) can be notified of the discrepancy, which can help facilitate open communication. For example, if a youth patient provides a different answer to a pop-question than the patient's parent, the parent can be notified (e.g., by interface icon, email, text message, etc.) so as to allow the parent to talk to their child about their medication usage even if the child does not independently approach their parent to discuss their medication.

Each goal can have at least one virtual reward and/or at least one physical reward associated therewith. Examples of virtual rewards include accessories for a user avatar shown on a user interface; achievement badge icons such as stars, shields, ribbons, smiley faces, animals, cartoon characters, etc. that can be displayed on a user interface; expanded choices of user avatars; points cumulatively tallied upon goal achievements to trigger other virtual and/or physical rewards based on point total; etc. Examples of physical rewards include a gift card for an online store and/or an actual stores; a coupon for a product, online store, and/or actual store; a free pass from a certain household chore; a printable certificate of achievement; a printable sticker; an IOU for a special treat (e.g., a trip to the zoo, seeing a movie of the patient's choice, a meal of the patient's choice prepared by someone in the patient's household; extra time for the patient to play with a certain toy; etc.); etc.

A goal can be known to a patient, which can allow the patient to actively be aware of and work toward the goal. However, a goal can be unknown to the patient such that achievement of the goal can result in a surprise reward. For example, an unknown goal can include a determination made by a patient's parent that the patient has been doing a good job keeping up with their medication and therefore deserves a reward, such as a virtual badge awarded by the parent to the patient that will appear on the patient's user interface the next time the user accesses the system. For example, an unknown goal can include a patient taking zero off-schedule doses of medication while otherwise taking a predetermined number or percentage of scheduled medication doses, which can help reward patients for adherence without discouraging patients from taking emergency medication when needed. For yet another example, an unknown goal can include a patient answering a certain number of pop-up questions provided on the user interface. After inputting answers to a predetermined number of questions, the patient can receive access to a set of previously locked accessories for their avatar. The patient can therefore learn that answering questions can result in rewards, thereby encouraging input of helpful data to the system.

The reward(s) associated with each goal can be predetermined by the system (e.g., a certain virtual reward for a certain achieved goal, a gift card of a certain monetary value for a certain web store if a certain number of daily goals are achieved a certain number of days in a row, etc.), or at least some goals can have user-customizable rewards (e.g., a monetary value amount of a gift card for a certain goal being able to be set by a parent of a youth patient; a congratulations message for a certain goal being customizable by the patient's care provider; a patient being able to select an avatar theme among a plurality of predetermined avatar themes, with each theme having a predetermined set of locked avatar accessories only unlocked so as to be accessible to the patient upon achievement of certain goals; a parent of a patient being able to select which of a plurality of web stores are acceptable stores for gift card rewards for the patient; a family member of a patient being able to identify how many points acquired through goal achievement are needed to excuse the patient from a certain household chore; a family member of a patient being able to identify a certain household chore that the patient can be excused from if a certain goal is met; etc.). Allowing at least some virtual and/or physical rewards to be customizable can help encourage adherence by allowing rewards to be chosen based on tastes of a particular patient so as to help maximize the patient's interest in adhering to their medication schedule; can allow the system to "grow" with a patient by allowing rewards to be changed to more appropriate rewards as the patient ages (e.g., increasing gift card values for older patients, changing excused chores, etc.); can allow the rewards to reflect time of year (e.g., having rewards reflect seasonal activities such as increased pool time in Summer for an achieved goal, a coupon for a discounted golf outing in Spring, a free pass from one day of snow shoveling in Winter, etc.), and/or can allow a reward for a goal to be changed to something bigger (e.g., a higher monetary value gift card, two avatar accessories instead of one, being excused from a chore for two weeks instead of one week, etc.) to help further encourage achievement of the goal; etc.

A patient, particularly a youth patient, may not even realize that adhering to their medication schedule is a necessary "chore," or may not mind the "chore" at all or as much, because the incentives system can help turn adherence into a game, e.g., by providing fun graphics, by providing real world rewards that patients can use and/or see in real life, etc. Providing incentives can thus help encourage adherence in a fun, non-clinical way. Because the incentives system can be provided for individual use and can be used by patients of nearly any age (e.g., any patient old enough to be responsible for at least some of their own medication administration), the incentives system can make the patients feel more independent and/or can make adherence feel less stressful to a patient than if one or more people, e.g., the patient's care provider, parent or other family member, etc., are directly reminding the patient verbally and/or in writing to take their medication on schedule and/or are repeatedly asking the patient whether and when they took their medication.

The user interface can be configured to show a patient's incentives data for the patient as the user and to show a patient's incentives data for someone other than the patient. The incentives module 1010 can thus allow a patient to access their own incentives data, which can help motivate the patient toward achieving their goals. The incentives module 1010 allowing someone associated with the patient (e.g., a family member, a doctor, etc.) to access the incentives data can help involve parties concerned about the patient in the patient's treatment and/or can help allow goals and/or rewards to be adjusted as needed by a third party to help the patient adhere to their medication schedule.

Figure 32:
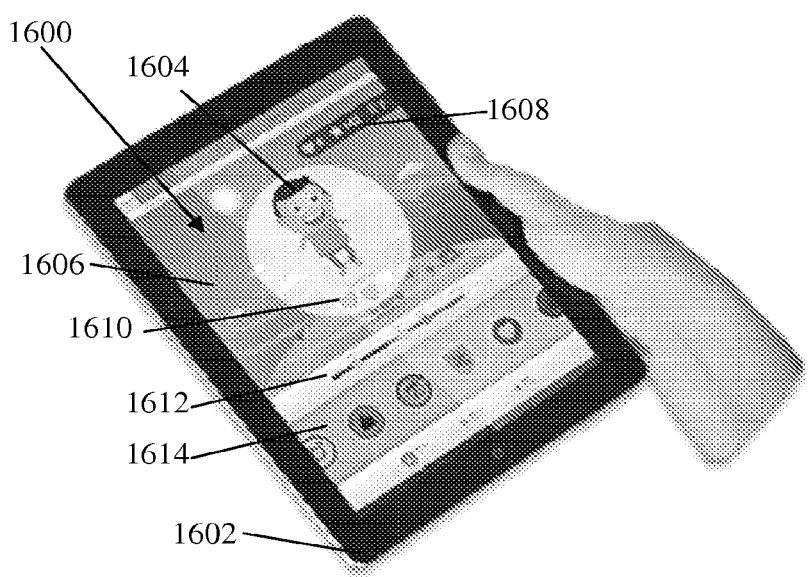
FIG. 32 is a perspective view of an embodiment of a client terminal displaying one embodiment of a user interface showing incentives information.

FIG. 32 illustrates one embodiment of a user interface 1600 configured to be displayed on a client terminal 1602 and show incentives data. The client terminal 1602 is shown as a tablet in the illustrated embodiment, but as mentioned above, any client terminal can be used to show the user interface 1600. The user interface 1600 shows incentives information for a single patient. The user interface 1600 shows incentives information including an avatar 1604 for the user (who may or may not the patient), a themed background 1606 for the avatar 1604, earned goal achievement badges 1608 (e.g., six heart badges for six days of 100% scheduled medication doses taken in the current week, 142 star badges for 142 total scheduled medication doses taken, and seven ribbon badges for seven weeks of 100% scheduled medication doses taken), a progress indicator 1610 that indicates progress toward a particular goal (e.g., two scheduled medication doses for the day have been taken on schedule with one scheduled dose remaining for the day), a medication timeline 1612 for the day indicating scheduled and taken medication doses, and a menu 1614 allowing selection of other information (e.g., adherence information, earned rewards, the patient's predetermined medication schedule, contact information for the patient's care provider, etc.) to be displayed to the user.

Figure 33:
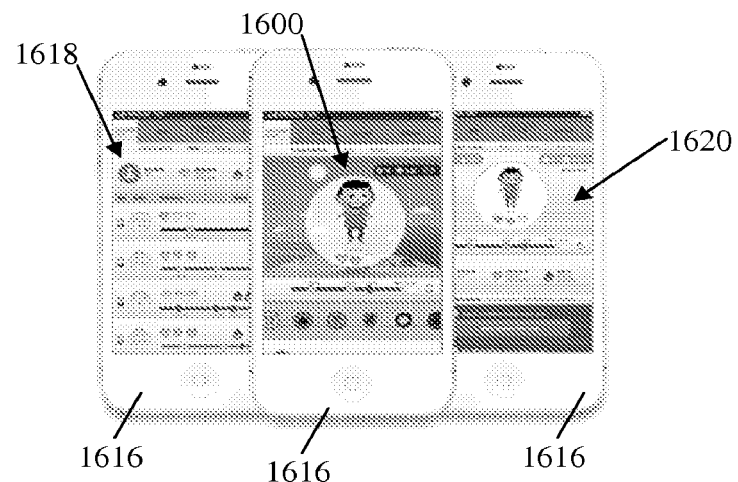
FIG. 33 is a perspective view of another embodiment of a client terminal displaying the user interface of FIG. 32 and the client terminal showing other embodiments of user interfaces showing incentives information.

FIG. 33 shows the user interface 1600 of FIG. 32 on a client terminal 1616 in the form of a mobile phone. FIG. 33 also shows the user interface 1600 on a second view 1618 of the user interface 1600 after user selection in the menu 1614 of adherence information, and shows the user interface 1600 on a third view 1620 of the user interface 1600 after user selection in the menu 1614 of a key for patient data.

Figure 34:
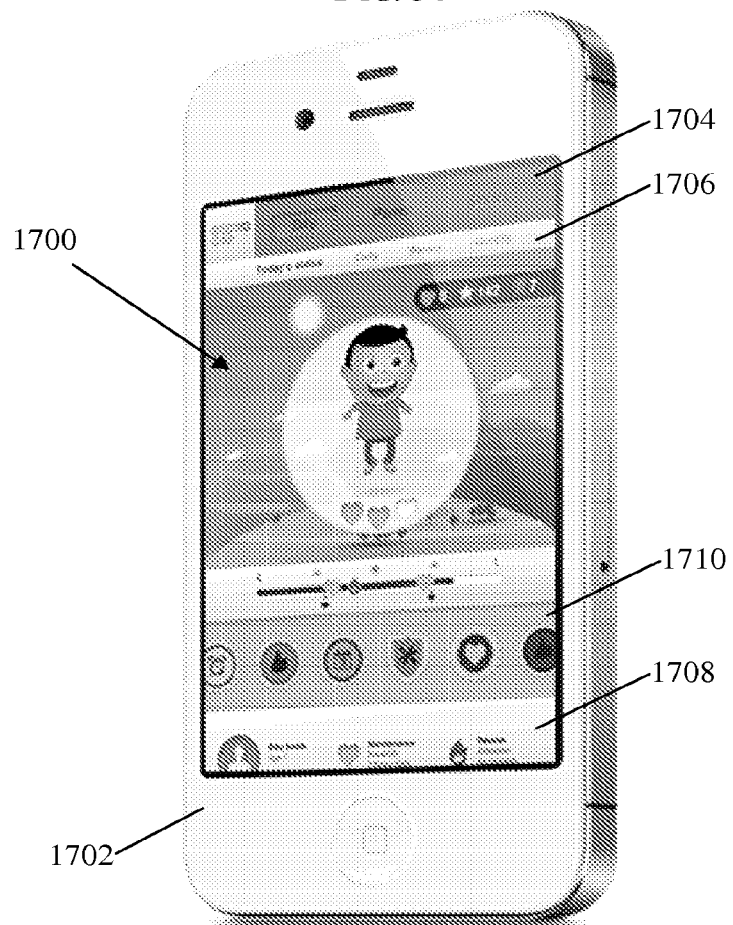
FIG. 34 is a perspective view of another embodiment of a client terminal displaying another embodiment of a user interface showing incentives information.

FIG. 34 shows another embodiment of a user interface 1700 showing incentives data on a client terminal 1702. The client terminal 1702 is shown as a mobile phone in the illustrated embodiment, but as mentioned above, any client terminal can be used to show the user interface 1700.

The user interface 1700 can provide user identity information 1704 that identifies a current user. The user identity 1704 information can be helpful since the user interface 1700 can be customized for different users, such as show different avatars for different users, show clinical data to care providers, provide different user input fields to different users (e.g., allow a parent to change rewards, allow a patient to input a reason why a scheduled medication dose was missed, provide incentives data to a care provider for multiple patients at once, etc.), etc. In the illustrated embodiment, the user identity is "Billy," a patient, with other possible user identities identified as "Parent" and "Doctor."

The user interface 1700 can provide view options 1706 configured to allow the user to selectively view incentives data for different time periods. The view options 1706 in the illustrated embodiment include "Today's status," "Daily," "Weekly," and "Monthly," with "Today's status" being the currently selected view.

The user interface 1700 can provide patient data 1708, e.g., below a menu 1710 allowing selection of other information similar to the menu 1614 of FIG. 32. The patient data 1708 can include any one or more of patient identity (e.g., name, age, etc.), maintenance data (e.g., name of prescribed medication, number of prescribed daily doses, etc.), rescue information (e.g., name of prescribed emergency medication, number of doses taken by the patient of the emergency medication, etc.).

Although the invention has been described by reference to specific embodiments, a person skilled in the art will understand that numerous changes may be made within the spirit and scope of the inventive concepts described. A person skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An accessory for use with an inhaler, the inhaler comprising a housing and medication disposed within the housing, the accessory comprising:
   a wireless communication mechanism configured to wirelessly receive a signal indicative of a predetermined medication schedule from an external device;
   a speaker;
   a sensor configured to sense a condition indicative of the medication being dispensed;
   a memory configured to store data regarding the sensed condition; and
   a processor configured to:
      output an audible sound via the speaker when a dosage of the medication is due according to the signal indicative of the predetermined medication schedule;
      receive a signal from the sensor;
      determine that medication was dispensed based on the signal received from the sensor; and
      send, via the wireless communication mechanism, the data indicating that the medication was dispensed to the external device.

2. The accessory of claim 1, further comprising:
   a housing configured to be removably and replaceably attached to the inhaler.

3. The accessory of claim 1, wherein the housing is configured to be removably and replaceably attached to a medication canister of the inhaler, and wherein the housing is configured to be movable with the medication canister relative to a housing of the inhaler to cause a dose of medication to be dispensed by the medication canister.

4. The accessory of claim 1, wherein the processor is configured to store the predetermined medication schedule in the memory, and output the audible sound via the speaker when the dosage of the medication is due according to the predetermined medication schedule stored in the memory.

5. The accessory of claim 1, wherein the sensor comprises an audio sensor; and
   wherein the processor is further configured to:
   compare feedback from the audio sensor to a stored profile indicative of the medication being dispensed;
   determine that the medication was dispensed when the feedback from the audio sensor exceeds a predetermined threshold; and
   store, in memory, the data, wherein the data indicates a time associated with the medication being dispensed.

6. The accessory of claim 1, further comprising:
   a button configured to be manually depressed;
   wherein the sensor comprises an audio sensor, and wherein the processor configured to receive an audio signal from the audio sensor and a signal from the button, and wherein the processor is configured to determine that medication was dispensed based on both the audio signal from the audio sensor and the signal from the button.

7. The accessory of claim 1, further comprising:
a button configured to be manually depressed to release medication, wherein the accessory is configured to change power states in response to the button being manually depressed.

8. The accessory of claim 7, wherein the sensor comprises an audio sensor, and wherein the processor configured to receive an audio signal from the audio sensor and a signal from the button, and wherein the processor is configured to determine that medication was dispensed based on both the audio signal from the audio sensor and the signal from the button.

9. The accessory of claim 4, wherein the processor is configured to receive an update to the predetermined medication schedule from the external device, store the updated medication schedule in the memory, and output the audible sound via the speaker when the dosage of the medication is due according to the updated medication schedule.

10. The accessory of claim 1, further comprising a motion sensor;
wherein the processor is configured to determine an orientation of the inhaler when the medication is dispensed.

11. The accessory of claim 10, wherein the processor is configured to determine whether the sensed orientation matches a predetermined orientation indicative of a medication-dispensing position.

12. The accessory of claim 1, wherein when the medication is not dispensed within a predetermined period of time after the audible sound is output from the speaker, the processor is configured to cause a missed dosage notation to be saved in the memory, the wireless communication mechanism being configured to wirelessly transmit the stored missed dosage notation to the external device.

13. The accessory of claim 1, wherein when the medication is not dispensed within a predetermined period of time after the audible sound is output from the speaker, the processor is configured to cause the speaker to output a second audible sound.

14. An accessory for use with an inhaler, the inhaler comprising a housing and medication disposed within the housing, the accessory comprising:
a housing configured to be removably and replaceably attached to the housing of the inhaler;
an audio sensor configured to sense a condition indicative of the medication being dispensed;
a motion sensor configured to sense orientation; and
a processor configured to:
compare feedback from the audio sensor to a stored profile indicative of the medication being dispensed;
determine that the medication was dispensed when the feedback from the audio sensor exceeds a predetermined threshold; and
store, in memory, data that indicates a time associated with the medication being dispensed and whether the sensed orientation matches a predetermined orientation indicative of a medication-dispensing position.

15. The accessory of claim 14, further comprising:
a wireless communication mechanism configured to wirelessly receive a predetermined medication schedule from an external device; and
a speaker;
wherein the processor is configured to output an audible sound via the speaker when a dosage of the medication is due according to the predetermined medication schedule.

16. An accessory for use with an inhaler, the inhaler comprising a housing and medication disposed within the housing, the accessory comprising:
an audio sensor and a pressure sensor, wherein the audio and pressure sensors are each configured to sense a respective condition indicative of the medication being dispensed;
a memory configured to store data regarding the sensed condition;
a wireless communication mechanism configured to wirelessly communicate with an external device; and
a processor configured to send, via the wireless communication mechanism, the data indicating that the medication was dispensed to the external device.

17. The accessory of claim 16, wherein the housing is configured to be removably and replaceably attached to a medication canister of the inhaler, and wherein the housing is configured to be movable with the medication canister relative to a housing of the inhaler to cause a dose of medication to be dispensed by the medication canister.

18. The accessory of claim 16, further comprising:
a speaker;
wherein the wireless communication mechanism is configured to receive a predetermined medication schedule from an external device; and
wherein the processor is configured to output an audible sound via the speaker when a dosage of the medication is due according to the predetermined medication schedule.

19. The accessory of claim 16, wherein the pressure sensor is configured to be manually depressed; and
wherein the processor configured to receive an audio signal from the audio sensor and a signal from the pressure sensor, and wherein the processor is configured to determine that medication was dispensed based on both the audio signal from the audio sensor and the signal from the pressure sensor.

20. The accessory of claim 16, further comprising:
a motion sensor; and
wherein the processor is configured to determine an orientation of the inhaler when the medication is dispensed.

* * * * *